(12) United States Patent
Gramer et al.

(10) Patent No.: US 8,084,594 B2
(45) Date of Patent: Dec. 27, 2011

(54) H2N3 INFLUENZA A VIRUSES AND METHODS OF USE

(75) Inventors: Marie Rene Gramer, Shoreview, MN (US); Kelly Lager, Colo, IA (US); Wenjun Ma, Ames, IA (US); Juergen Richt, Manhattan, KS (US); Amy Vincent, Nevada, IA (US)

(73) Assignees: The United States of America as represented by the Secretary of Agriculture, Washington, DC (US); Iowa State University Research Foundation, Inc., Ames, IA (US); Regents of the University of Minnesota, St. Paul, MN (US)

( * ) Notice: Subject to any disclaimer, the term of this patent is extended or adjusted under 35 U.S.C. 154(b) by 510 days.

(21) Appl. No.: 12/171,992

(22) Filed: Jul. 11, 2008

(65) Prior Publication Data

US 2009/0047286 A1 Feb. 19, 2009

Related U.S. Application Data

(60) Provisional application No. 61/002,242, filed on Nov. 7, 2007, provisional application No. 60/961,930, filed on Jul. 25, 2007, provisional application No. 60/961,072, filed on Jul. 18, 2007, provisional application No. 60/959,333, filed on Jul. 13, 2007.

(51) Int. Cl.
*C07H 21/02* (2006.01)
*C12N 15/00* (2006.01)
(52) U.S. Cl. .................................. 536/23.1; 435/320.1
(58) Field of Classification Search ....................... None
See application file for complete search history.

(56) References Cited

OTHER PUBLICATIONS

Naeve "Fatty acids on the A/Japan/305/57 influenza virus hemagglutinin have a role in membrane fusion" EMBO J. 3857-3866;1990.*
Obenauer, J. C. et al. "Large-Scale Sequence Analysis of Avian Influenza Isolates" Science 311:1576-1580; 2006.*
Obenauer, J.C. et al. "Supporting Online Material for Large-Scale Sequence Analysis of Avian Influenza Isolates" Published Jan. 26, 2006 on Science Express. Page numbers are not identified.*

* cited by examiner

*Primary Examiner* — Bo Peng
(74) *Attorney, Agent, or Firm* — John Fado; Randall E. Deck; Lesley Shaw

(57) ABSTRACT

The present invention provides influenza A viruses that include a hemagglutinin subtype H2, a neuraminidase subtype N3, or the combination thereof. Included in the present invention are H2 hemagglutinins and N3 neuraminidases, and the polynucleotides encoding the polypeptides. Antibody to the polypeptides, and methods of using the viruses, polypeptides, polynucleotides, and antibodies are also provided.

6 Claims, 27 Drawing Sheets

Fig. 1
a)
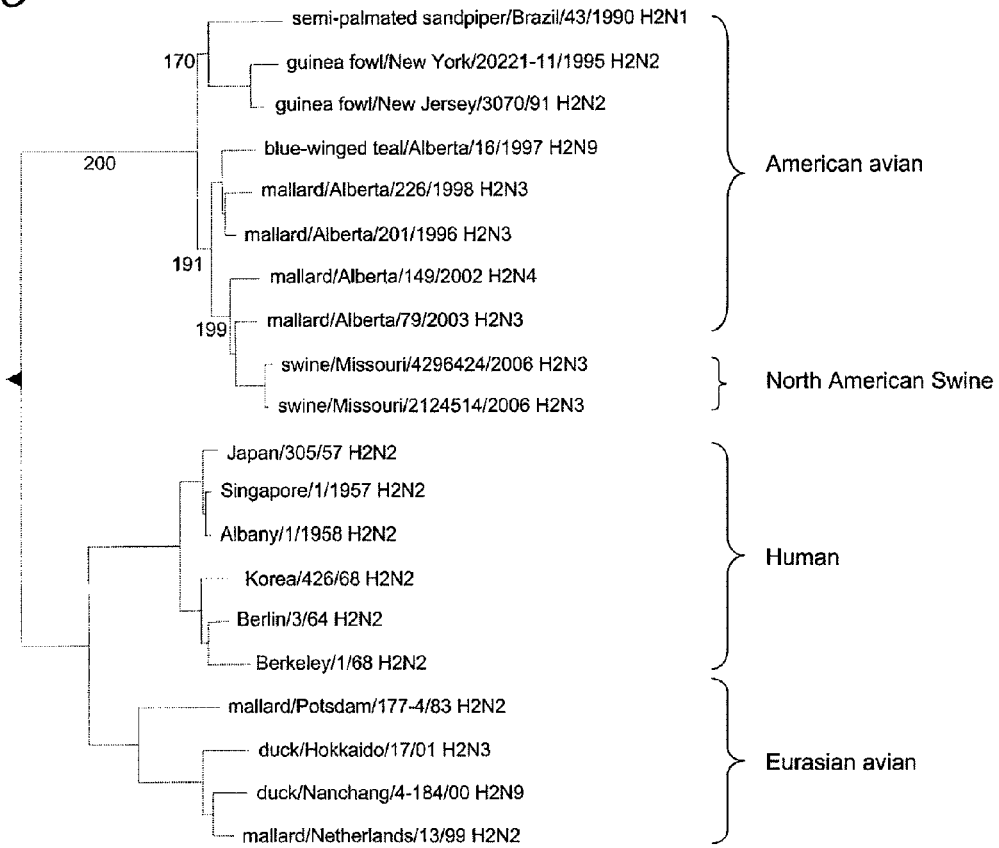
b)
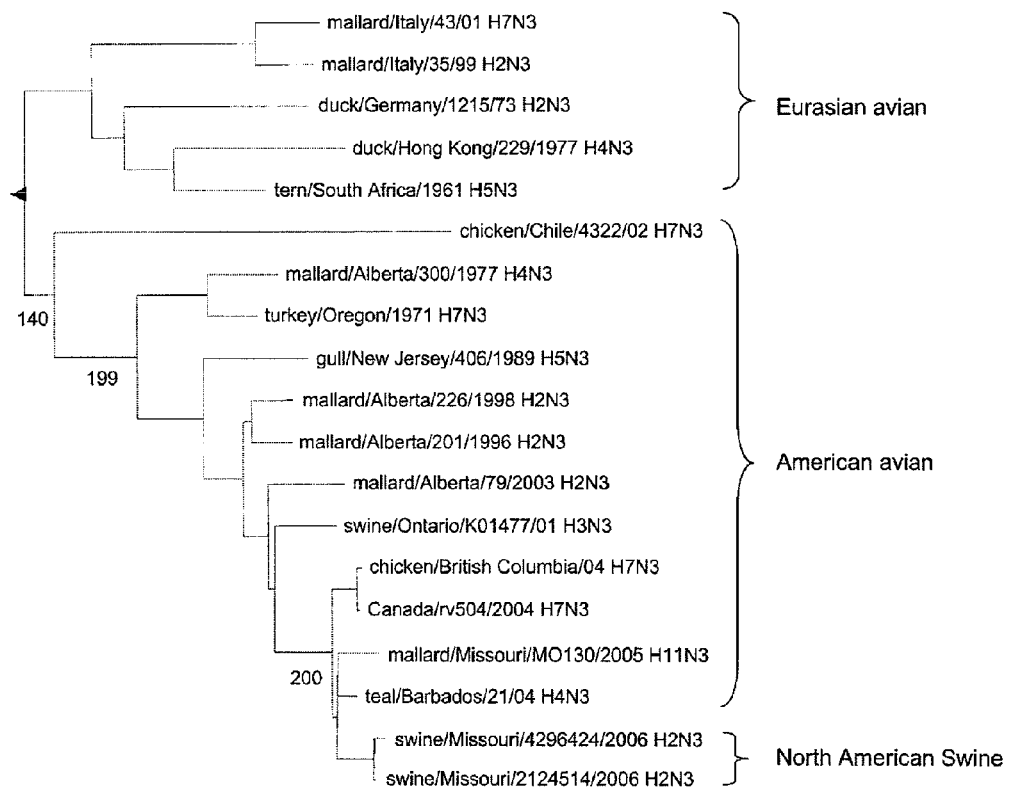

Fig. 2
a)
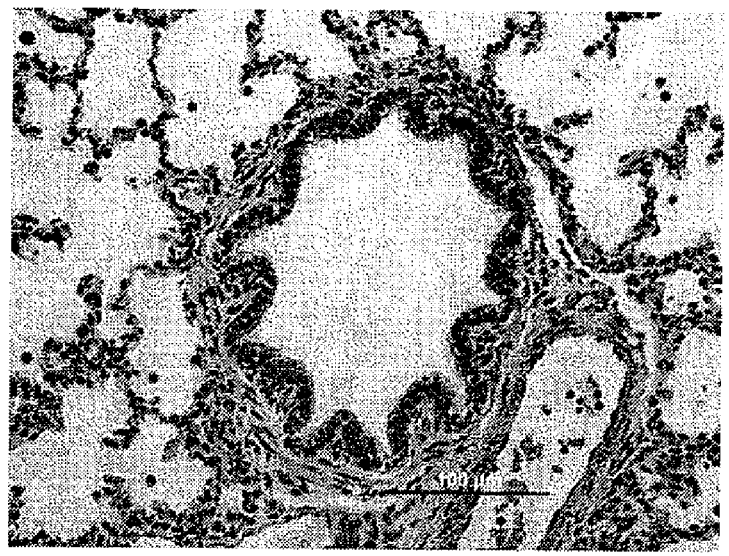
b)
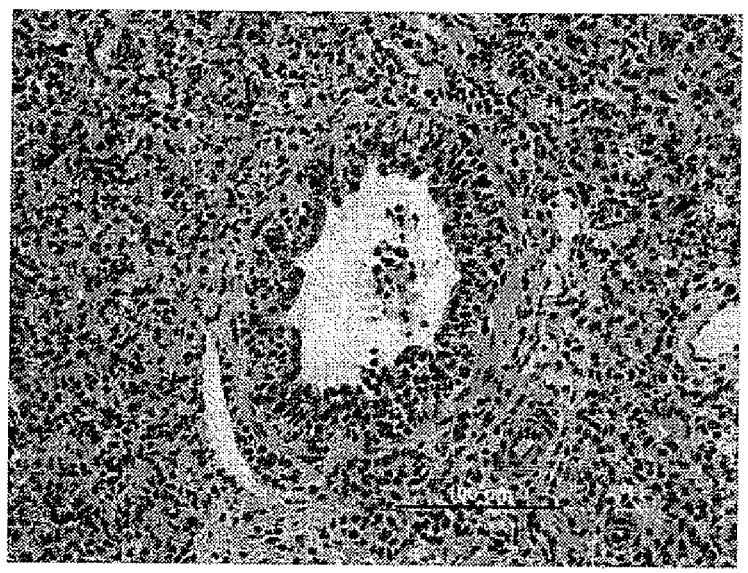

Fig. 3
a)
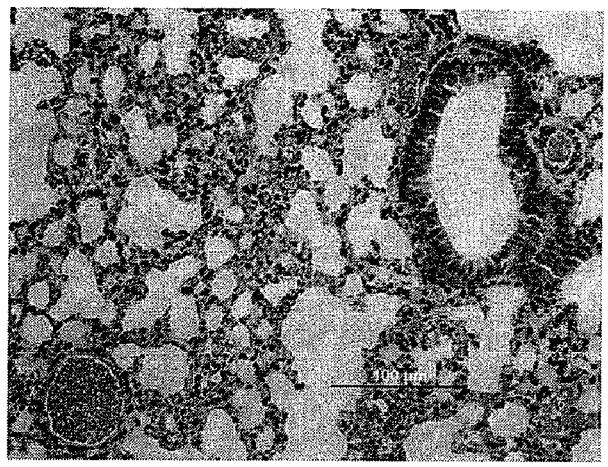
b)
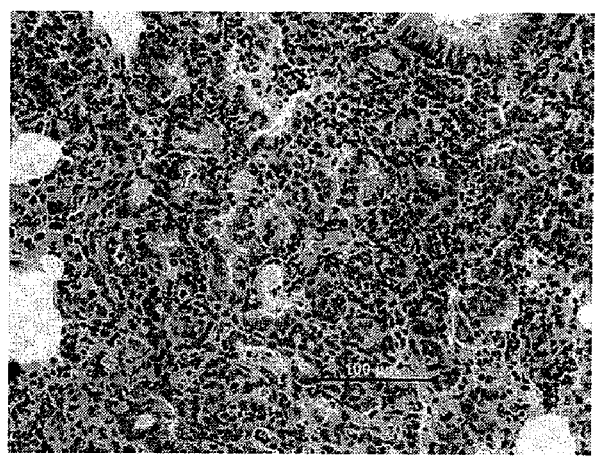
c)
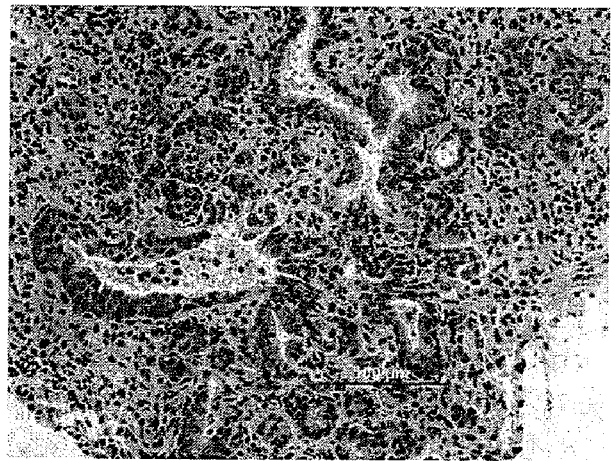

Figure 4

SEQ ID NO:1

```
   1 ttattcgtct tcagggagca aaagcagggg ttataccata gacaaccgaa caaagacaat
  61 gaccatcact tttctcatcc tcctgttcac agtagtgaaa ggggaccaaa tatgcatcgg
 121 ataccatgcc aacaattcca cagaaaaagt tgacacaatc ttggaacgaa acgtcaccgt
 181 gactcatgcc aagaacattc ttgaaaagac gcataatgga aagttgtgca gattgagcgg
 241 gatccctcca ttggaactgg gggattgcag cattgcaggt tggctccttg gaaatccgga
 301 atgtgaccgg ctcttaagtg tacctgaatg gtcctatata gtggaaaagg aaaacccggt
 361 gaatggtctg tgctatccag gcagtttcaa tgattatgag gaattgaaac atcttctcac
 421 cagtgtgaca cactttgaga aagttaagat tctgcccaga gatcaatgga cccagcacac
 481 aacaactggt ggttctcggg cctgtgcagt atctggaaac ccgtcattct ttaggaacat
 541 ggtttggctt acaaagaaag ggtcaaacta cccaattgct aaaaggtcat acaacaacac
 601 aagtggggag caaatgctgg taatatgggg gatacatcac cccaatgacg atgcggaaca
 661 gaggacactg taccagaatg tgggaacata tgtttccgtt ggaacatcaa cactaaataa
 721 gaggtcaatc cctgaaatag caacaaggcc aaagtcaatg gactgggagg aagaatggga
 781 attctcttgg actctattgg agacatggga tgtcataaat tttgagagca ctggtaattt
 841 aattgcacca gaatacggat tcaaaatatc aagagagga agctcaggaa ttatgaagac
 901 agagaaaata cttgaaaatt gtgaaaccaa atgtcagacc cccttggggg caataaatac
 961 aacattgccc tttcacaaca ttcacccatt gacaataggt gagtgcccca gtatgtaaa
1021 gtcagataga ctgattttgg cgacaggact aagaaatgtc ccccagattg aatcaagggg
1081 attgtttgga gcaatagctg ggtttataga aggcggatgg caagggatgg ttgatggctg
1141 gtatgggtac catcacagca tgatcaagg atcaggatat gcagcagaca agaatccac
1201 tcaaaaggca attgatggaa taactaacaa agtaaattct gtgattgaaa agatgaacac
1261 tcagtttgag gctgttggga agagttcaa caacctagag agaagactgg aaaacttaaa
1321 taaaaagatg gaagatggat tattgatgt atggacatat aatgccgaac tcctagttct
1381 aatggaaaat gagaggacac ttgatttcca tgattctaat gtgaagaatc tgtacgataa
1441 ggtcagaatg caattgagag acaatgctaa ggaaataggg aacggatgct ttgagtttta
1501 tcataaatgt gatgatgaat gcatgaatag tgtcaggaat gggacatatg attatatcaa
1561 atatgaggaa gagtccaagc tgaacaggaa cgaaatcaaa ggagtgaaat tgagcaatat
1621 ggggtttat caaatacttg ctatatacgc tacagttgca ggctctttgt cactggcaat
1681 catgatagct gggatttctt tctggatgtg ttctaatggg tctctgcaat gcagaatttg
1741 catatgactg taagtcaatt tgtaattaaa aacacccttg tttctactaa tacgagacga
1801 tataa
```

SEQ ID NO:9

```
  1 mtitflillf tvvkgdqici gyhannstek vdtilernvt vthaknilek thngklcrls
 61 gipplelgdc siagwllgnp ecdrllsvpe wsyivekenp vnglcypgsf ndyeelkhll
121 tsvthfekvk ilprdqwtqh tttggsraca vsgnpsffrn mvwltkkgsn ypiakrsynn
181 tsgeqmlviw gihhpnddae qrtlyqnvgt yvsvgtstln krsipeiatr pkvnglggrm
241 efswtlletw dvinfestgn liapeygfki skrgssgimk tekilencet kcqtplgain
301 ttlpfhnihp ltigecpkyv ksdrlilatg lrnvpqiesr glfgaiagfi eggwqgmvdg
361 wygyhhsndq gsgyaadkes tqkaidgitn kvnsviekmn tqfeavgkef nnlerrlenl
421 nkkmedgfid vwtynaellv lmenertldf hdsnvknlyd kvrmqlrdna keigngcfef
481 yhkcddecmn svrngtydyi kyeeesklnr neikgvklsn mgvyqilaiy atvagslsla
541 imiagisfwm csngslqcri ci
```

Figure 5

SEQ ID NO:2

```
  1 ttaaagatga gtcttctaac cgaggtcgaa acgtatgttc tctctatcgt cccgtcaggc
 61 cccctcaaag ccgagatagc acagagactc gaagacgttt ttgcagggaa aaacaccgat
121 cttgaggctc tcatggaatg gctaaagaca agaccaatcc tgtcacctct gactaagggg
181 attttagggt tgtgttcac gctcaccgtg cccagtgagc gaggactgca gcgtagacgt
241 tttgttcaga atgccctcaa tgggaatggt gacccgaaca acatggacaa ggcggtcaaa
301 ctttacagga aactaaaaag ggaaataaca ttccatgggg ccaaagaagt agcgctcagt
361 tactctgctg gtgcacttgc cagttgcatg ggctcatat acaacagaat gggaactgtc
421 accactgagg ttgcctttgg tctggtatgc gcaacctgtg aacagattgc tgattctcag
481 catcgatccc atagacaaat ggtgacaaca accaatccac taatcaggca cgagaacaga
541 atggtgatag ccagcacaac agctaaagca atggaacaaa tggctggatc aagcgaacaa
601 gcagcagagg ctatggaggt tgccagccag gctagacaaa tggtacaggc aatgagaaca
661 attgggactc accctagttc cagcactggt ctaaaagatg atcttcttga aaatttacag
721 gcctatcaga agcggatggg agtgcaaatg caacgattca atgatcctc tcattgatgc
781 tgcaagcatc attggatttt gcacctgat attgtggatt cttgatcgtc ttttttcaa
841 atgcatttac cgtcgcttta aatacggtct gcaaagaggg ccttctacgg aaggagtgcc
901 ggagtccatg agggaagaat atcgacagaa acagcagagt gctgtggatg ttgacgatgg
961 tcattttgtc aacatagtgc tagagtaaa
```

SEQ ID NO:10

```
  1 mslltevety vlsivpsgpl kaeiaqrled vfagkntdle almewlktrp ilspltkgil
 61 gfvftltvps erglqrrrfv qnalngngdp nnmdkavkly rklkreitfh gakevalsys
121 agalascmgl iynrmgtvtt evafglvcat ceqiadsqhr shrqmvtttn plirhenrmv
181 iasttakame qmagsseqaa eamevasqar qmvqamrtig thpssstglk ddllenlqay
241 qkrmgvqmqr fk
```

SEQ ID NO:45

```
  1 mslltevetp irsgweckcn dsndplidaa siigilhlil wildrlffkc iyrrfkyglq
 61 rgpstegvpe smreeyrqkq qsavdvddgh fvnivle
```

Figure 6

SEQ ID NO:3

```
   1 cgagatgaat ccgaatcaga agataataac aatcggggta gtgaatacca ctctgtcaac
  61 aatagccctt ctcattggag tgggaaactt agttttcaac acagtcatac atgagaaaat
 121 aggagaccat caaatagtga cctatccaat aataacgacc cctgcagtac cgaactgcag
 181 tgacactata ataacataca ataacactgt gataaacaac ataacaacaa caataataac
 241 tgaagaagaa aggcctttca agtctccact accgctgtgc cccttcagag gattcttccc
 301 ttttcacaag gacaatgcaa tacgactggg tgaaaacaaa gacgtcatag tcacaagaga
 361 gccttatgtt agctgcgata atgacaactg ctggtccttt gctctcgcac aaggagcatt
 421 gctagggacc aaacatagca atgggaccat taagacagg acaccatata ggtctctaat
 481 tcgtttccca ataggaacag ctccagtact aggaaattat aaagagatat gcattgcttg
 541 gtcgagcagc agttgctttg acgggaaaga gtggatgcat gtgtgcatga cagggaacga
 601 taatgatgca agtgcccaga taatatatgg agggagaatg acagactcca ttaaatcatg
 661 gagaaaggac atactaagaa ctcaggagtc tgaatgccaa tgcattgacg ggacttgtgt
 721 tgttgctgtc acagatggcc ctgctgctaa tagtgcagat tacagggttt actggatacg
 781 ggagggaaaa ataataaagt atgaaaatgt tcccaaaaca aagatacaac acttagaaga
 841 atgttcctgc tatgtggaca ttgatgttta ctgtatatgt agggacaatt ggaagggctc
 901 taacagacct tggatgagaa tcaacaacga gactatactg gaaacagggt atgtatgtag
 961 taaattccac tcagacaccc caggccagc tgacccttca acaatgtcat gtgactcccc
1021 aagcaatgtc aatggaggac cggagtgaa ggggtttggt tcaaagctg cgatgatgt
1081 atggttaggt agaacagtgt cgactagtgg tagatcgggc tttgaaatta tcaaagttac
1141 agaagggtgg atcaactctc ctaaccatgt caaatcaatt acacaaacac tagtgtccaa
1201 caatgactgg tcaggctatt ccggtagctt cattgtcaaa gccaaggact gttttcagcc
1261 ctgtttttat gttgagctta tacgagggag gcccaacaag aatgatgacg tctcttggac
1321 aagtaatagt atagttactt tctgtggact agacaatgaa cctggatcgg gaaattggcc
1381 agatggttct aacattgggt ttatgcccaa gtaatagaaa aaagcacctt gtttctacta
```

SEQ ID NO:11

```
   1 mnpnqkiiti gvvnttlsti alligvgnlv fntvihekig dhqivtypii ttpavpncsd
  61 tiitynntvi nnitttiite eerpfksplp lcpfrgffpf hkdnairlge nkdvivtrep
 121 yvscdndncw sfalaqgall gtkhsngtik drtpyrslir fpigtapvlg nykeiciaws
 181 ssscfdgkew mhvcmtgndn dasaqiiygg rmtdsikswr kdilrtqese cqcidgtcvv
 241 avtdgpaans adyrvywire gkiikyenvp ktkiqhleec scyvdidvyc icrdnwkgsn
 301 rpwmrinnet iletgyvcsk fhsdtprpad pstmscdsps nvnggpgvkg fgfkagddvw
 361 lgrtvstsgr sgfeiikvte gwinspnhvk sitqtlvsnn dwsgysgsfi vkakdcfqpc
 421 fyvelirgrp nknddvswts nsivtfcgld nepgsgnwpd gsnigfmpk
```

Figure 7

SEQ ID NO:4

```
   1 acccatcaat gagtgacatc gaagccatgg cgtctcaagg caccaaacga tcatatgaac
  61 aaatggagac tggtggggaa cgccaggatg ccacagaaat cagagcatct gtcggaagaa
 121 tgattggtgg aatcgggaaa ttctacatcc aaatgtgcac tgaactcaaa ctcagtgact
 181 atgagggacg actaatccaa aatagcatga aatagagag aatggtgctc tctgcttttg
 241 atgagagaag aaataaatac ctagaagagc atcccagtgc agggaaggat cctaagaaaa
 301 ctggaggacc catatataga agagtagacg gaaagtggat gagagaactc attctttatg
 361 acaaagaaga aataaggaga gtttggcgcc aagcaaacaa tggtgaagat gcaacagctg
 421 gtcttgctca tatcatgatt tggcactcca atctgaatga tgccacgtac cagagaacaa
 481 gagcgcttgt tcgcaccgga atggatccca gaatgtgctc tctaatgcaa ggttcaacac
 541 ttcccagaag gtctggggcc gcaggtgctg cagtgaaagg agttggaaca atagcaatgg
 601 aattaatcag aatgatcaaa cgtgggatca atgaccgaaa cttctggaga ggtgaaaatg
 661 gacgaaagac aaggattgca tatgaaagaa tgtgcaatat tctcaaggga aaatttcaga
 721 cagctgccca gagggcaatg atggatcaag tgagagaaag tcggaacccc ggaaacgctg
 781 agattgaaga tctcattttc ctggcacggt cagcacttat tctaagggga tcagttgcac
 841 ataagtcttg cctgcctgct tgtgtgtatg ggcttgcagt ggcaagtggg catgactttg
 901 aaagggaagg gtattcactg gtcgggatag acccatttaa attactccaa aacagtcaag
 961 tgttcagctt gataagacca atgaaaaccc agctcacaa gagtcaatta gtgtggatgg
1021 catgccactc tgctgcattt gaggatctga gggtatcaag tttcatcaga gggaagaaag
1081 tgattccaag aggaaggctc tccacaagag gggttcagat tgcttcaaat gagaatgtgg
1141 aagccatgga ttccaatacc ttagagctga aagcagata ctgggccata aggaccagaa
1201 gtggaggaaa taccaatcaa cagaaggcat ccgcgggcca gatcagtgtg caacccacat
1261 tctcagtgca acggaatctc ccttttgaaa gagcaaccgt tatggcagct ttcagcggga
1321 acaatgaagg acggacatcc gatatgcgaa cagaagttat aaggatgatg gaaaatgcaa
1381 agccagaaga tttgtccttc caggggcggg gagtcttcga gctctcggac gaaaaagcaa
1441 cgagcccgat cgtgccttcc tttgacatga gtaatgaagg atcttatttc ttcggagaca
1501 atgcagagga gtatgacagt tgaggaaaaa ta
```

SEQ ID NO:12

```
  1 masqgtkrsy eqmetggerq dateirasvg rmiggigkfy iqmctelkls dyegrliqns
 61 mtiermvlsa fderrnkyle ehpsagkdpk ktggpiyrrv dgkwmrelil ydkeeirrvw
121 rqanngedat aglahimiwh snlndatyqr tralvrtgmd prmcslmqgs tlprrsgaag
181 aavkgvgtia melirmikrg indrnfwrge ngrktriaye rmcnilkgkf qtaaqrammd
241 qvresrnpgn aeiedlifla rsalilrgsv ahksclpacv yglavasghd feregyslvg
301 idpfkllqns qvfslirpne npahksqlvw machsaafed lrvssfirgk kviprgrlst
361 rgvqiasnen veamdsntle lrsrywairt rsggntnqqk asagqisvqp tfsvqrnlpf
421 eratvmaafs gnnegrtsdm rtevirmmen akpedlsfqg rgvfelsdek atspivpsfd
481 msnegsyffg dnaeeyds
```

Figure 8

SEQ ID NO:5

```
  1 caaaaagaca taatggactc cacaactgtg tcaagctttc aggtagactg tttcctttgg
 61 cacatccgca aacggtttgc agacaatgga ttgggtgatg ccccattcct tgatcggctc
121 cgccgagatc aaaagtctct aaaaggaaga ggcaacaccc ttggcctcga cattgaaaca
181 gccactcttg ttgggaaaca aattgtggag tggattttga agaagaatc cagcgataca
241 cttaagatga ctattgcatc tgtacctact tcgcgctatt tagctgacat gaccctcgag
301 gaaatgtcac gagactggtt aatgctcatg cctaggcaaa agataatagg ccctctttgt
361 gtgcgaatgg accaggcgat catggaaaag aacatcatac tgaaagcgaa cttcagtgtg
421 atctttaacc gattagagac tttgatacta ctaagggctt tcacagagga gggaacaatc
481 gttggagaaa tttcacaatt accttctctt ccaggacata ctaatgagga tgtcaaaaat
541 gcaattgggg tcctcatcgg aggacttgaa tggaatggta cacggttcg aggctctgaa
601 aatctacaga gattcgcttg gagaaaccgt aatgaggatg ggagaccttc actacctcca
661 gagaagaaat gaaaagtggc gagagcaatt gggacaaaaa tttgaggaaa taaggtggtt
721 aattgaagaa gtgcggcaca gattgaaaac gacagagaat agttttgaac aaataacatt
781 catgcaagcc ttacaactac tgcttgaagt agaacaagag ataaggactt tctcgtttca
841 gcttatttaa t
```

SEQ ID NO:13

```
  1 mdsttvssfq vdcflwhirk rfadnglgda pfldrlrrdq kslkgrgntl gldietatlv
 61 gkqivewilk eessdtlkmt iasvptsryl admtleemsr dwlmlmprqk iigplcvrmd
121 qaimekniil kanfsvifnr letlillraf teegtivgei sqlpslpght nedvknaigv
181 ligglewngn tvrgsenlqr fawrnrnedg rpslppekk
```

SEQ ID NO:46

```
  1 mdsttvssfq dilmrmskmq lgsssedlng mvtrfealki yrdslgetvm rmgdlhylqr
 61 rnekwreqlg qkfeeirwli eevrhlktt ensfeqitfm qalqllleve qeirtfsfql
121 i
```

Figure 9

SEQ ID NO:6

```
   1 ccaaaatgga agactttgtg cgacaatgct tcaatccaat gatcgtcgag cttgcggaaa
  61 aggcaatgaa ggaatatggg gaagatccaa aaatcgaaac taacaaattc gcagcaatat
 121 gcactcactt ggaagtatgt ttcatgtatt cggatttcca cttcattgat gagcggggcg
 181 aatcaataat tgtggaatct ggtgatccaa atgcattact gaagcaccga tttgaaataa
 241 ttgaaggaag agaccgaaca atggcctgga cagtggtgaa tagcatctgc aacaccacag
 301 gggtcgagaa gcctaaattt cttccggatc tgtatgatta caggagaac cgattcattg
 361 aaattggagt aacacggaga gaggttcata tatactacct agagaaagcc aacaagataa
 421 aatctgagaa gacacacatt cacatctttt catttactgg agaagaaatg gccaccaaag
 481 cagactacac tcttgatgaa gaaagcaggg caagaatcaa aaccaggcta ttcactataa
 541 gacaagaaat ggccagcagg ggtctatggg attcctttcg tcagtctgaa agaggcgaag
 601 agacaattga ggaaagattt gaaatcacag gaaccatgcg taggcttgcc gaccaaagtc
 661 tcccaccgaa cttctccagc cttgaaaact ttagagccta tgtggatgga ttcgaaccga
 721 acggctgcat tgagggcaag ctttctcaaa tgtcaaaaga agtgaatgcc aggattgagc
 781 cattcctgaa gacaacacca cgccctctca aattacctga tgggcccect tgctctcagc
 841 ggtcaaaatt cttgctgatg gatgccttga aactaagcat cgaagacccg agtcacgagg
 901 gagagggtat accactatac gatgcaatca aatgcatgaa gacattttc ggctggaaag
 961 agcccaacat aatcaaacca catgagaaag cataaatcc caattacttt ctggcttgga
1021 agcaagtgct agcagagctc caggaccttg aaaatgaaga aagatccca aagacaaaga
1081 acatgaagaa aacaagccaa ttgaagtggg cgcttggtga gaatatggca ccagaaaaag
1141 tggactttga ggattgcaag gacattggcg atctaaagca gtatgatagt gatgagccag
1201 agcctagatc gctggcaagc tggatccaga gtgaattcaa taaggcatgt gaattgaccg
1261 actcgagctg gatagaactt gatgaaatag agaagatgt tgctccgatt gaacacattg
1321 caagtatgag gaggaactat tttacagcag aagtgtccca ctgcagggcc actgaataca
1381 taatgaaagg agtctacata aatacagctc tgctcaatgc atcttgtgca gccatggatg
1441 acttccagct gattccaatg ataagcaaat gtagaacaaa ggaaggaaga cggaaaacaa
1501 acctgtatgg gttcatcata aaaggaagat ctcatttgag gaatgatact gatgtggtaa
1561 actttgtgag catggaattt tctctcactg acccgaggct agaaccacac aaatgggaga
1621 agtattgtgt tcttgaaata ggagatatgc tcctgaggac tgcaataggc caagtgtcaa
1681 ggcccatgtt cctgtacatt agaaccaatg ggacctccaa gatcaagatg aaatggggta
1741 tggaaatgag gcgctgcctc cttcaatctc ttcaacagat tgagagcatg attgaggctg
1801 agtcttctgt caaagaaaag gacatgacta aggaattctt tgaaaacaag tcggaaacgt
1861 ggccaattgg agaatccccc agaggagtag aggaaggctc tattgggaaa gtatgcagaa
1921 ccttactggc aaagtctgta ttcaacagtc tgtacgcatc ccacaacatt gaggggtttt
1981 cagctgaatc gagaaaattg cttctcattg ttcaggcact tagggacaac ctggaacctg
2041 ggaccttcga tcttgggggg ctatacgaag caattgagga gtgcctgatt aatgatcct
2101 gggttttgct taatgcatct tggttcaact ccttcctcac acatgcactg aaatagttgt
2161 ggcaatgcta ctatttgcta tccatactgt ccaaaaagt accttgtttc tactaataga
2221 agagcgatga
```

SEQ ID NO:14

```
  1 medfvrqcfn pmivelaeka mkeygedpki etnkfaaict hlevcfmysd fhfiderges
 61 iivesgdpna llkhrfeiie grdrtmawtv vnsicnttgv ekpkflpdly dykenrfiei
121 gvtrrevhiy ylekankiks ekthihifsf tgeematkad ytldeesrar iktrlftirq
181 emasrglwds frqsergeet ieerfeitgt mrrladqslp pnfsslenfr ayvdgfepng
241 ciegklsqms kevnariepf lkttprplkl pdgppcsqrs kfllmdalkl siedpshege
301 giplydaikc mktffgwkep niikphekgi npnyflawkq vlaelqdlen eekipktknm
361 kktsqlkwal genmapekvd fedckdigdl kqydsdepep rslaswiqse fnkaceltds
421 swieldeige dvapiehias mrrnyftaev shcrateyim kgvyintall nascaamddf
481 qlipmiskcr tkegrrktnl ygfiikgrsh lrndtdvvnf vsmefsltdp rlephkweky
541 cvleigdmll rtaigqvsrp mflyirtngt skikmkwgme mrrcllqslq qiesmieaes
```

Figure 9 (continued)

```
601 svkekdmtke ffenksetwp igesprgvee gsigkvcrtl laksvfnsly aspqlegfsa
661 esrklllivq alrdnlepgt fdlgglyeai eeclindpwv llnaswfnsf lthalk
```

Figure 10

SEQ ID NO:7

```
   1 ttgaatggat gtcaatccga ccctactttt cctaaaagtt ccagcgcaaa atgccataag
  61 caccacattc ccttatactg gagatcctcc atacagccat ggaacaggaa caggatacac
 121 catggacaca gtcaacagaa cacatcaata ttcagaaaaa gggaagtgga cgacaaacac
 181 tgagactggg gcaccccaac tcaatccaat tgatggacca ctacctgagg ataatgaacc
 241 aagtgggtat gcacagacag actgtgttct agaggccatg gctttccttg aagaatccca
 301 cccagggata tttgagaatt catgccttga acaatggaa gttgttcaac aaacaagggt
 361 ggataaaacta actcaaggtc gccagactta tgattggaca ttaaacagaa atcaaccagc
 421 agcaactgca ttggccaaca ccatagaagt ttttaggtcg aatagtctaa cagccaatga
 481 gtcaggaaga ctaataaatt tcctaaagga tgtaatggaa tcaatggata gagaagaagt
 541 ggagataaca acacactttc gaagaaaaag gagagtgaga gacaacatga ccaagaagat
 601 ggtcacacaa gaacaatag gaaagaaaaa acaaagattg agtaagagaa gttatctaat
 661 aagagcactt acattgaata cgatgaccaa agatgcagag agaggcaaat aaaaagaag
 721 ggctatcgca cacccggga tgcaattag agggttcgtg tactttgttg agactttagc
 781 taggagcatt tgcgaaaagc ttgaacagtc tggactccca gtaggggaa atgaaagaa
 841 ggccaaattg gcaaatgttg tgagaaaaat gatgactaat tcacaagaca cagagctttc
 901 tttcacaatc actggggaca atactaagtg gaatgaaaat caaaatcctc gaatgttcct
 961 ggcgatgatt acatatatca cccgaaatca acccgagtgg ttcagaaaca tcctgagcat
1021 ggcacccata atgttttcaa acaaaatggc aagactagga aagggtaca tgttcgagag
1081 taaaaggatg aagctccgaa cacaaatacc agcagaaatg ctagcaagca ttgatctgaa
1141 gtatttcaat gaatcaacaa ggaagaaaat tgagaaaata aggcctcttc taatagatgg
1201 cacagcatca ttgagccctg gaatgatgat gggcatgttc aacatgctaa gtacggtttt
1261 gggagtctcg atactgaatc ttggacaaaa gaaatacacc aggacaacat actggtggga
1321 tgggctccaa tcctccgacg attttgccct cattgtgaat gcaccaaatt atgagggaat
1381 acaagcagga gtgaatagat tctacaggac ctgcaagtta gtaggaataa acatgagcaa
1441 aaagaagtcc tatataaata aacagggac atttgaattc acaagctttt tttatcgcta
1501 tgggtttgtg gctaattta gcatggagct gcccagtttt ggagtgtctg aataaatga
1561 atcagctgat atgagtattg gagtaacagt gataaagaac aatatgataa acaatgatct
1621 tggacctgca acagcccaga tggcccttca attgttcatc aaagactaca gatacacata
1681 taggtgccac agaggagaca cacaaattca gacgagaaga tcattcgagc taaagaagct
1741 atgggatcaa acccgatcaa atgcaggact attagtatct gatggaggac aaacttata
1801 caatatcagg aatcttcaca ttcctgaagt ctgcttaaaa tgggagctaa tggatgagga
1861 ttatcgggga aggctttgta atccctgaa tccttttgtc agccataaag agattgattc
1921 tgtaaacaat gctgtggtga tgccagccca tggcccagcc aaaagcatgg aatatgatgc
1981 cgttgcaact acacactcct ggatccccaa gaggaatcgc tctattctca acacaagcca
2041 aaggggaatt cttgaggatg aacagatgta ccagaagtgc tgcaacctgt tcgagaaatt
2101 tttccctagt agttcataca ggagaccggt tggaatttct agcatggtgg aggccatggt
2161 gtctagggcc cggattgatg ccagaatcga cttcgagtct ggacggatta agaagaaga
2221 gttctctgag atcataagga tctgttccac cattgaagaa ctcagacggc aaacatgatg
2281 aatttggctt gtccttcatg aaaaaatgcc ttgtttctac taatacgaga cgatataaa
```

SEQ ID NO:15

```
  1 mdvnptllfl kvpaqnaist tfpytgdppy shgtgtgytm dtvnrthqys ekgkwttnte
 61 tgapqlnpid gplpednepd gyaqtdcvle amafleeshp gifensclet mevvqqtrvd
121 kltqgrqtyd wtlnrnqpaa talantievf rsnsltanes grlinflkdv mesmdreeve
181 itthfrrkrr vrdnmtkkmv tqrtigkkkq rlskrsylir altlntmtkd aergklkrra
241 iatpgmqirg fvyfvetlar sicekleqsg lpvggnekka klanvvrkmm tnsqdtelsf
301 titgdntkwn enqnprmfla mityitrnqp ewfrnilsma pimfsnkmar lgkgymfesk
361 rmklrtqipa emlasidlky fnestrkkie kirpllidgt aslspgmmmg mfnmlstvlg
421 vsilnlgqkk ytrttywwdg lqssddfali vnapnyegiq agvnrfyrtc klvginmskk
481 ksyinktgtf eftsffyryg fvanfsmelp sfgvsgines admsigvtvi knnminndlg
```

Figure 10 (continued)

```
541 pataqmalql fikdyrytyr chrgdtqiqt rrsfelkklw dqtrsnagll vsdggpnlyn
601 irnlhipevc lkwelmdedy rgrlcnplnp fvshkeidsv nnavvmpahg paksmeydav
661 atthswipkr nrsilntsqr giledeqmyq kccnlfekff psssyrrpvg issmveamvs
721 raridaridf esgrikkeef seiiricsti eelrrqt
```

Figure 11

SEQ ID NO:8

```
   1 tatattcaat atggagagaa taaaagaact aagagaccta atgtcgcagt cccgcactcg
  61 cgaaatactc accaagacca ctgtggacca tatggccata atcaaaaagt acacatcggg
 121 aaggcaagag aagaaccctg cactcagaat gaagtggatg atggcaatga agtacccaat
 181 cacagcagac aagagaataa tggacatgat tccagagaga aatgaacaag acaaaccct
 241 ctggagcaaa acaaacgatg ctggatcgga ccgcgtgatg gtatcacccc tggctgtaac
 301 atggtggaat aggaatggcc aacagcaag cacagttcac tacccaagg tatataaaac
 361 ttatttcgaa aaagtcgaaa ggttaaaaca tggtaccttt ggccctgtcc acttcaggaa
 421 tcaagttaaa ataagaagga gagttgacac aaaccctggt cacgcagatc tcagagccaa
 481 ggaggcacag gatgtgatca tggaagttgt tttcccaaat gaagtggggg caagaatact
 541 gacatcagag tcacagctga caataacaaa agagaagaaa gaagagctcc aggattgtaa
 601 aattgctccc ttaatggtgg catacatgct agaaaaagag ttggtccgta aaacgaggtt
 661 tctcccggtg gctggtggaa caggcagtgt ttatattgaa gtgctgcatt taactcaggg
 721 gacatgctgg gagcaaatgt acactccagg aggagaagtg agaaatgatg atgttgacca
 781 aagtttgatt attgctgcta gaaacatagt aagaagagca gcagtgtcag cagacccatt
 841 agcatctctt ttggaaatgt gccacagcac acagattgga ggaataagga tggtggacat
 901 ccttagacag aatccaacgg aggaacaagc cgtagacata tgcaaggcag caatggggct
 961 gaggattagc tcctctttca gctttggtgg gttcactttc aaaagaacaa gtgggtcatc
1021 agttaagaga gaagaagaag tgctcacggg caaccttcaa acactgaaaa taagagtaca
1081 tgaaggatat gaagaattca atggtcgg gagaagagca acagctattc tcagaaaagc
1141 aaccaggaga ttgatccagt tgatagtaag tgggagagac gagcagtcaa ttgctgaggc
1201 aataattgtg gccatggtat tttcacaaga ggactgcatg atcaaggcag ttaggggcga
1261 tctgaacttt gtcaataggg caaaccagcg actgaatccc atgcatcaac tcttgaggca
1321 tttccaaaaa gatgcaaaag tgcttttcca gaattgggga attgaaccca tcgacaatgt
1381 gatgggaatg atcgggatat gcccgatat gaccccaagc acggagatgt cgctgagagg
1441 gataagagtc agcaaaatgg gagtagatga atactccagc acggagagag tggtagtgag
1501 cattgacaga ttttgaggg ttcgggatca acgagggaac gtactattgt ctcctgaaga
1561 ggtcagtgag acacaaggga cggagaaatt ggcaataact tattcgtcat cgatgatgtg
1621 ggagatcagt ggccctgagt cagtgctggt caacacttat caatggatca taaggaattg
1681 ggaaagtttg aaaattcaat ggtcacaaga tcccacgatg ttatacaaca aaatggaatt
1741 tgaaccattt cagtctcttg tccctaaagc aaccagaagt cgttacagtg ggttcgtgag
1801 gacactgttc cagcaaatgc gggatgtgat tggaacattt gacactgtcc aaataataaa
1861 acttctcccc tttgctgctg ctccaccaga acagagtagg atgcagtttt cctcactgac
1921 tgtgaatgtg agaggatcag ggttgaggat actggtaaga ggcaattctc cagtattcaa
1981 ttacaataaa gcaaccaaaa ggcttacagt tcttggaaag gatgcaggtg aattgaccga
2041 agacccagat gaaggcacag ctggagtgga gtctgctgtc ctgaggggat ttctcatttt
2101 gggcaaagaa gacaagagat atggtccagc attaagcatc aatgaactga gcaatcttgc
2161 aaaaggagag aaagctaatg tgctaattgg caaggagac gtagtgttgg taatgaaacg
2221 gaaacgggac tctagcatac ttactgacag ccagacagcg accaaaagaa ttcggatggc
2281 catcaattag tgtcgaatt
```

SEQ ID NO:16

```
  1 merikelrdl msqsrtreil tkttvdhmai ikkytsgrqe knpalrmkwm mamkypitad
 61 krimdmiper neqgqtlwsk tndagsdrvm vsplavtwwn rngptastvh ypkvyktyfe
121 kverlkhgtf gpvhfrnqvk irrrvdtnpg hadlrakeaq dvimevvfpn evgariltse
181 sqltitkekk eelqdckiap lmvaymleke lvrktrflpv aggtgsvyie vlhltqgtcw
241 eqmytpggev rnddvdqsli iaarnivrra avsadplasl lemchstqig girmvdilrq
301 npteeqavdi ckaamglris ssfsfggftf krtsgssvkr eeevltgnlq tlkirvhegy
361 eeftmvgrra tailrkatrr liqlivsgrd eqsiaeaiiv amvfsqedcm ikavrgdlnf
421 vnranqrlnp mhqllrhfqk dakvlfqnwg iepidnvmgm igilpdmtps temslrgirv
481 skmgvdeyss tervvvsidr flrvdqrgn vllspeevse tqgteklait ysssmmweis
```

Figure 11 (continued)

```
541 gpesvlvnty qwiirnwesl kiqwsqdptm lynkmefepf qslvpkatrs rysgfvrtlf
601 qqmrdvigtf dtvqiikllp faaappeqsr mqfssltvnv rgsglrilvr gnspvfnynk
661 atkrltvlgk dageltedpd egtagvesav lrgflilgke dkrygpalsi nelsnlakge
721 kanvligqgd vvlvmkrkrd ssiltdsqta tkrirmain
```

Figure 12

SEQ ID NO:17

```
   1 ttattcgtct tcaaggagca aaagcagggg ttataccata gacaaccgaa caaagacaat
  61 gaccatcact tttctcatcc tcctgttcac agtagtgaaa ggggaccaaa tatgcatcgg
 121 ataccatgcc aacaattcca cagaaaaagt tgacacaatc ttggaacgaa acgtcaccgt
 181 gactcatgcc aagaacattc ttgaaaagac gcataatgga aagttgtgca gattgagtgg
 241 aatccctcca ttggaactgg gggattgcag cattgcaggt tggctccttg gaaatccgga
 301 atgtgaccgg ctcttaagtg tacctgaatg gtcctatata gtggaaaagg aaaacccggt
 361 gaatggtctg tgctatccag gcagtttcaa tgattatgag gaattgaaac atcttctcac
 421 cagtgtgaca cactttgaga agttaagat tctgcccaga gatcaatgga cccagcacac
 481 aacaactggt ggttctcggg cctgtgcagt atctggaaac ccgtcattct ttaggaacat
 541 ggtttggctt acaaagaaag ggtcaaacta ctcaattgct aaaaggtcat acaacaacac
 601 aagtggggag caaatgctgg taatatgggg gatacatcac cccaatgacg atgcggaaca
 661 gaggacactg taccagaatg tgggaacata tgtttccgtt ggaacatcaa cactaaataa
 721 gaggtcaatc cctgaaatag caacaaggcc caagtcaat ggactgggag gaagaatgga
 781 attctcttgg actctattgg agacatggga tgtcataaat tttgagagca ctggtaattt
 841 aattgcacca gaatacggat tcaaaatatc aagagagga agctcaggaa ttatgaagac
 901 agagaaaata cttgaaaatt gtgaaaccaa atgtcagacc cccttggggg caataaatac
 961 aacattgccc tttcacaaca ttcacccatt gacaataggt gagtgcccca agtatgtaaa
1021 gtcagataga ctgattttgg cgacaggagt aagaaatgtc ccccagatta atcaagggg
1081 attgtttgga gcaatagctg gtttatagaa ggcggatgg caagggatgg ttgatggctg
1141 gtatgggtac catcacagca atgatcaagg atcaggatat gcagcagaca aagaatccac
1201 tcaaaaggca attgatggaa taactaacaa agtaaattct gtgattgaaa agatgaacac
1261 tcagtttgag gctgttggga aagagttcaa caacctagag agaaggctgg aaaacttaaa
1321 taaaaagatg gaagatggat ttattgatgt atggacatat aatgccgaac tcctagttct
1381 aatggaaaat gagaggacac ttgatttcca tgattctaat gtgaagaatc tgtacgataa
1441 ggtcagaatg caattgagag acaatgctaa ggaaataggg aacggatgct tgagtttta
1501 tcataaatgt gatgatgaat gcatgaatag tgtcaggaat gggacatatg attatcccaa
1561 atatgaggaa gagtccaagc tgaacaggaa cgaaatcaaa ggagtgaaat tgagcaatat
1621 gggggtttat caaatacttg ctatatacgc tacagttgca ggctctttgt cactggcaat
1681 catgatagct gggatttctt tctggatgtg ttctaatggg tctctgcaat gcagaatttg
1741 catatgactg taagtcaatt tgtaattaaa aaaactcctt
```

SEQ ID NO:25

```
  1 mtitflillf tvvkgdqici gyhannstek vdtilernvt vthaknilek thngklcrls
 61 gipplelgdc siagwllgnp ecdrllsvpe wsyivekenp vnglcypgsf ndyeelkhll
121 tsvthfekvk ilprdqwtqh tttggsraca vsgnpsffrn mvwltkkgsn ysiakrsynn
181 tsgeqmlviw gihhpnddae qrtlyqnvgt yvsvgtstln krsipeiatr pkvnglggrm
241 efswtlletw dvinfestgn liapeygfki skrgssgimk tekilencet kcqtplgain
301 ttlpfhnihp ltigecpkyv ksdrlilatg vrnvpqiesr glfgaiagfi eggwqgmvdg
361 wygyhhsndq gsgyaadkes tqkaidgitn kvnsviekmn tqfeavgkef nnlerrlenl
421 nkkmedgfid vwtynaellv lmenertldf hdsnvknlyd kvrmqlrdna keigngcfef
481 yhkcddecmn svrngtydyp kyeeesklnr neikgvklsn mgvyqilaiy atvagslsla
541 imiagisfwm csngslqcri ci
```

Figure 13

SEQ ID NO:18

```
  1 gtttaaagat gagtcttcta accgaggtcg aaacgtatgt tctctctatc gtcccgtcag
 61 gcccccctcaa agccgagata gcacagagac tcgaagacgt ttttgcaggg aaaaacaccg
121 atcttgaggc tctcatggaa tggctaaaga caagaccaat cctgtcacct ctgactaagg
181 ggattttagg gtttgtgttc acgctcaccg tgcccagtga gcgaggactg cagcgtagac
241 gttttgttca gaatgccctc aatgggaatg gtgacccgaa caacatggac aaggcggtca
301 aactttacag gaaactaaaa agggaaataa cattccatgg ggccaaagaa gtagcgctca
361 gttactctgc tggtgcactt gccagttgca tgggcctcat atacaacaga atgggaactg
421 tcaccactga ggttgccttt ggtctggtat gcgcaacctg taacagatt gctgattctc
481 agcatcgatc ccatagacaa atggtgacaa caccaatcc actaatcagg cacgagaaca
541 gaatggtgat agccagcaca acagctaaag caatggaaca aatggctgga tcaagcgaac
601 aagcagcaga ggctatggag gttgccagcc aggctagaca aatggtacag gcaatgagaa
661 caattgggac tcaccctagt ccagcactg gtctaaaaga tgatcttctt gaaaatttac
721 aggcctatca gaaacggatg ggagtgcaaa tgcaacgatt caaatgatcc tctcactgat
781 gctgcaagca tcattgggat tttgcacctg atattgtgga ttcttgatcg tcttttttttc
841 aaatgcattt accgtcgctt taaatacggt ctgcaaagag ggccttctac ggaaggagtg
901 ccggagtcca tgagggaaga atatcgacag aaacagcaga gtgctgtgga tgttgacgat
961 ggtcattttg tcaacatagt gctagagtaa a
```

SEQ ID NO:26

```
  1 mslltevety vlsivpsgpl kaeiaqrled vfagkntdle almewlktrp ilspltkgil
 61 gfvftltvps erglqrrrfv qnalngngdp nnmdkavkly rklkreitfh gakevalsys
121 agalascmgl iynrmgtvtt evafglvcat ceqiadsqhr shrqmvtttn plirhenrmv
181 iasttakame qmagsseqaa eamevasqar qmvqamrtig thpssstglk ddllenlqay
241 qkrmgvqmqr fk
```

SEQ ID NO:47

```
  1 mslltevetp irngweckcn dsndpltdaa siigilhlil wildrlffkc iyrrfkyglq
 61 rgpstegvpe smreeyrqkq qsavdvddgh fvnivle
```

Figure 14

SEQ ID NO:19

```
   1 agatgaatcc gaatcagaag ataataacaa tcggggtagt gaataccact ctgtcaacaa
  61 tagcccttct cattggagtg ggaaacttaa ttttcaacac agtcatacat gagaaaatag
 121 gagaccatca aatagtgacc tatccaacaa taacgacccc tgcagtaccg aactgcagtg
 181 acactataat aacatacaat aacactgtga taaacaacat aacaacaaca ataataactg
 241 aagaagaaag gcctttcaag tctccactac cgctgtgccc cttcagagga ttcttccctt
 301 ttcacaagga caatgcaata cgactgggtg aaaacaaaga cgtcatagtc acaagagagc
 361 cttatgttag ctgcgataat gacaactgct ggtcctttgc tctcacacaa ggagcattgc
 421 tagggaccaa acatagcaat gggaccatta agacaggac accatatagg tctctaattc
 481 gtttcccaat aggaacagct ccagtactag gaaattataa agagatatgc attgcttggt
 541 cgagcagcag ttgctttgac gggaaagagt ggatgcatgt gtgcatgaca gggaacgata
 601 atgatgcaag tgcccagata atatatggag ggagaatgac agactccatt aaatcatgga
 661 gaaaggacat actaagaact caggagtctg aatgccaatg cattgacggg acttgtgttg
 721 ttgctgtcac agatggccct gctgctaata gtgcagatta cagggtttac tggatacggg
 781 agggaaaaat aataaagtat gaaaatgttc caaaacaaa gatacaacac ttagaagaat
 841 gttcctgcta tgtggacatt gatgtttact gtatatgtag ggacaattgg aagggctcta
 901 acagaccttg gatgagaatc aacaacgaga ctatactgga aacagggtat gtatgtagta
 961 aattccactc agacaccccc aggcccgctg acccttcaac aatgtcatgt gactccccaa
1021 gcaatgtcaa tggaggaccc ggagtgaagg ggtttggttt caaagctggc gatgatgtat
1081 ggttaggtag aacagtgtcg actagtggta gatcgggctt tgaaattatc aaagttacag
1141 aagggtggat caactctcct aaccatgtca atcaattac acaaacacta gtgtcaaaca
1201 atgactggtc aggctattcc ggtagcttca ttgtcaaagc caaggactgt tttcagccct
1261 gttttttatgt tgagcttata cgagggaggc ccaacaagaa tgatgacgtc tcttggacaa
1321 gtaatagtat agttactttc tgtggactag acaatgaacc tggatcggga aattggccag
1381 atggttctaa cattgggttt atgcccaagt aatagaaaaa agcaccttgt ttctacta
```

SEQ ID NO:27

```
   1 mnpnqkiiti gvvnttlsti alligvgnli fntvihekig dhqivtypti ttpavpncsd
  61 tiitynntvi nnitttiite eerpfksplp lcpfrgffpf hkdnairlge nkdvivtrep
 121 yvscdndncw sfaltqgall gtkhsngtik drtpyrslir fpigtapvlg nykeiciaws
 181 ssscfdgkew mhvcmtgndn dasaqiiygg rmtdsikswr kdilrtqese cqcidgtcvv
 241 avtdgpaans adyrvywire gkiikyenvp ktkiqhleec scyvdidvyc icrdnwkgsn
 301 rpwmrinnet iletgyvcsk fhsdtprpad pstmscdsps nvnggpgvkg fgfkagddvw
 361 lgrtvstsgr sgfeiikvte gwinspnhvk sitqtlvsnn dwsgysgsfi vkakdcfqpc
 421 fyvelirgrp nknddvswts nsivtfcgld nepgsgnwpd gsnigfmpk
```

Figure 15

SEQ ID NO:20

```
   1 gataatcact caatgagtga catcgaagcc atggcgtctc aaggcaccaa acgatcatat
  61 gaacaaatgg agactggtgg ggaacgccag gatgccacag aaatcagagc atctgtcgga
 121 agaatgattg gtggaatcgg gaaattctac atccaaatgt gcactgaact caaactcagt
 181 gactatgagg gacgactaat ccaaaatagc atgacaatag agagaatggt gctctctgct
 241 tttgatgaga aagaaataa atacctagaa gagcatccca gtgcaggaa ggatcctaag
 301 aaaactggag gacccatata tagaagagta gacggaaagt ggatgagaga actcattctt
 361 tatgacaaag aagaaataag gagagtttgg cgccaagcaa acaatggtga agatgcaaca
 421 gctggtcttg ctcatatcat gatttggcac tccaatctga atgatgccac gtaccagaga
 481 acaagagcgc ttgttcgcac cggaatggat cccagaatgt gctctctaat gcaaggttca
 541 acacttccca aaggtctgg ggccgcaggt gctgcagtga aggagttgg aacagtagca
 601 atggaattaa tcagaatgat caaacgtggg atcaatgacc gaaacttctg gagaggtgaa
 661 aatggacgaa agacaaggat tgcatatgaa agaatgtgca atattctcaa gggaaaattt
 721 cagacagctg cccagagggc aatgatggat caagtgagag aaagtcggaa ccccggaaac
 781 gctgagattg aagatctcat tttcctggca cggtcagcac ttattctaag aggatcagtt
 841 gcacataagt cttgcctgcc tgcttgtgtg tatgggcttg cagtggcaag tgggcatgac
 901 tttgaaaggg aagggtattc actggtcggg atagcccat ttaaattact ccaaaacagt
 961 caagtgttca gcttgataag accaaatgaa aacccagctc acaagagtca attagtgtgg
1021 atggcatgcc actctgctgc atttgaggat ctgagggtat caagtttcat cagagggaag
1081 aaagtgattc caagaggaag gctctccaca agagggttc agattgcttc aaatgagaat
1141 gtggaagcca tggattccaa taccttagag ctgagaagca gatactggc cataaggacc
1201 agaagtggag gaaataccaa tcaacagaag gcatccgcgg gccagatcag tgtgcaaccc
1261 acattctcag tgcaacggaa tctccctttt gaaagagcaa ccattatggc agctttcagc
1321 gggaacaatg aaggacggac atccgatatg cgaacagaag ttataaggat gatggaaaat
1381 gcaaagccag aagatttgtc cttccagggg cggggagtct tcgagctctc ggacgaaaaa
1441 gcaacgagcc cgatcgtgcc ttcctttgac atgagtaatg aaggatctta tttcttcgga
1501 gacaatgcag aggagtatga cagttgagga aaaata
```

SEQ ID NO:28

```
   1 masqgtkrsy eqmetggerq dateirasvg rmiggigkfy iqmctelkls dyegrliqns
  61 mtiermvlsa fderrnkyle ehpsagkdpk ktggpiyrrv dgkwmrelil ydkeeirrvw
 121 rqanngedat aglahimiwh snlndatyqr tralvrtgmd prmcslmqgs tlprrsgaag
 181 aavkgvgtva melirmikrg indrnfwrge ngrktriaye rmcnilkgkf qtaaqrammd
 241 qvresrnpgn aeiedlifla rsalilrgsv ahksclpacv yglavasghd feregyslvg
 301 idpfkllqns qvfslirpne npahksqlvw machsaafed lrvssfirgk kviprgrlst
 361 rgvqiasnen veamdsntle lrsrywairt rsggntnqqk asagqisvqp tfsvqrnlpf
 421 eratimaafs gnnegrtsdm rtevirmmen akpedlsfqg rgvfelsdek atspivpsfd
 481 msnegsyffg dnaeeyds
```

Figure 16

SEQ ID NO:21

```
  1 caacgacata atggactcca ccactgtgtc aagctttcag gtagactgtt tcctttggca
 61 catccgcaaa cggtttgcag acaatggatt gggtgatgcc ccattccttg atcggctccg
121 ccgagatcaa aagtctctaa aaggaagagg caacaccctt ggcctcgaca ttgaaacagc
181 cactcttgtt gggaaacaaa ttgtggagtg gattttgaaa gaagaatcca gcgatacact
241 taagatgact attgcatccg tacctacttc gcgctattta gctgacatga ccctcgagga
301 aatatcacga gactggttaa tgctcatgcc taggcaaaag ataataggcc tctttgtgt
361 gcgaatggac caggcgatca tggaaaagaa catcatactg aaagcgaact tcagtgtgat
421 ctttaaccga ttagagactt tgatactact aagggctttc actgaggagg aacaatcgt
481 tggagaaatt tcacaattac cttctcttcc aggacatact aatgaggatg tcaaaaatgc
541 aattggggtc ctcatcggag gacttgaatg gaatggtaac acggttcgag gctctgaaaa
601 tctacagaga ttcgcttgga gaaaccgtaa tgaggatggg agaccttcac tacctccaga
661 gaagaaatga aaagtggcga gagcaattgg gacaaaaatt tgaggaaata aggtggttaa
721 ttgaagaagt gcggcacaga ttgaaaacga cagagaatag ttttgaacaa ataacattca
781 tgcaagcctt acaactactg cttgaagtag aacaagagat aaggactttc tcgtttcagc
841 ttatttaatg ataac
```

SEQ ID NO:29

```
  1 mdsttvssfq vdcflwhirk rfadnglgda pfldrlrrdq kslkgrgntl gldietatlv
 61 gkqivewilk eessdtlkmt iasvptsryl admtleeisr dwlmlmprqk iigplcvrmd
121 qaimekniil kanfsvifnr letlillraf teegtivgei sqlpslpght nedvknaigv
181 ligglewngn tvrgsenlqr fawrnrnedg rpslppekk
```

SEQ ID NO:48

```
  1 mdsttvssfq dilmrmskmq lgsssedlng mvtrfealki yrdslgetvm rmgdlhylqr
 61 rnekwreqlg qkfeeirwli eevrhrlktt ensfeqitfm qalqllleve qeirtfsfql
121 i
```

Figure 17

SEQ ID NO:22

```
   1 accaaaaaaa tggaagactt tgtgcgacaa tgcttcaatc caatgatcgt cgagcttgcg
  61 gaaaaggcaa tgaaggaata tggggaagat ccaaaaatcg aaactaacaa attcgcagca
 121 atatgcactc acttggaagt atgtttcatg tattcggatt tccacttcat tgatgagcga
 181 ggcgaatcaa taattgtgga atctggtgat ccaaatgcat tactgaagca ccgatttgaa
 241 ataattgaag gaagagacag aacaatggcc tggacagtgg tgaatagcat ctgcaacacc
 301 acagggggtcg agaagcctaa atttcttccg gatctgtatg attacaagga gaaccgattc
 361 attgaaattg gagtaacacg gagagaggtt catatatact acctagagaa agccaacaag
 421 ataaaatctg agaagacaca cattcacatc ttttcattta ctggagaaga aatggccacc
 481 aaagcagact acactcttga tgaagaaagc agggcaagaa tcaaaaccag gctattcact
 541 ataagacaag aaatggccag caggggtcta tggattcct ttcgtcagtc tgaaagaggc
 601 gaagagacaa ttgaggaaag atttgaaatc acaggaacca tgcgtaggct gccgaccaa
 661 agtctcccac cgaatttctc cagccttgaa aactttagag cctatgtgga tggattcgaa
 721 ccgaacggct gcattgaggg caagctttct caaatgtcaa agaagtgaa tgccaggatt
 781 gagccattcc tgaagacaac accacgccct ctcaaattac ctgatgggcc ccttgctct
 841 cagcggtcaa aattcttgct gatggatgcc ttgaaactaa gcatcgaaga cccgagtcac
 901 gagggagagg gtataccact atacgatgca atcaaatgca tgaagacatt tttcggctgg
 961 aaagagccca acataatcaa accacatgag aaaggcataa atcccaatta ctttctggct
1021 tggaagcaag tgctagcaga actccaggac cttgaaaatg aagagaagat cccaaagaca
1081 aagaacatga agaaaacaag ccaattgaag tgggtgcttg gtgagaatat ggcaccagaa
1141 aaagtggact ttgaggattg caaggacatt ggcgatctaa agcagtatga tagtgatgag
1201 ccagagccta gatcgctggc aagctggatc cagagtgaat tcaataaggc atgtgaattg
1261 accgactcga gctggataga acttgatgaa ataggagaag atgttgctcc gattgaacac
1321 attgcaagta tgaggaggaa ctattttaca gcagaagtgt cccactgcag ggccactgag
1381 tacataatga aaggagtcta cataaataca gctctgctca atgcatcttg tgcagccatg
1441 gatgacttcc agctgattcc aatgataagc aaatgtagaa caaggaagg aagacggaaa
1501 acaaacctgt atgggttcat cataaaagga agatctcatt tgaggaatga tactgatgtg
1561 gtaaactttg tgagcatgga atttctctc actgacccga ggctagaacc acacaaatgg
1621 gagaagtatt gtgttcttga ataggagat atgctcctga ggactgcaat aggccaagtg
1681 tcaaggccca tgttcctgta cattagaacc aatgggacct caagatcaa gatgaaatgg
1741 ggtatggaaa tgaggcgctg cctccttcaa tctcttcaac agattgagag catgattgag
1801 gctgagtctt ctgtcaaaga aaggacatg actaaggaat tctttgaaaa caagtcggaa
1861 acgtggccaa ttggagaatc ccccagagga gtagaggaag ctctattgg gaaagtatgc
1921 agaaccttac tggcaaagtc tgtattcaac agtctgtacg catctccaca acttgagggg
1981 ttttcagctg aatcgagaaa attgcttctc attgttcagg cacttaggga aacctggaa
2041 cctgggacct tcgatcttgg ggggctatac gaagcaattg aggagtgcct gattaatgat
2101 ccctgggttt tgcttaatgc atcttggttc aactccttcc tcacacatgc actgaaatag
2161 ttgtggcaat gctactattt gctatccata ctgtccaaaa aagtaccttg tttctactaa
2221 tagaagagcg at
```

SEQ ID NO:30

```
  1 medfvrqcfn pmivelaeka mkeygedpki etnkfaaict hlevcfmysd fhfiderges
 61 iivesgdpna llkhrfeiie grdrtmawtv vnsicnttgv ekpkflpdly dykenrfiei
121 gvtrrevhiy ylekankiks ekthihifsf tgeematkad ytldeesrar iktrlftirq
181 emasrglwds frqsergeet ieerfeitgt mrrladqslp pnfsslenfr ayvdgfepng
241 ciegklsqms kevnariepf lkttprplkl pdgppcsqrs kfllmdalkl siedpshege
301 giplydaikc mktffgwkep niikphekgi npnyflawkq vlaelqdlen eekipktknm
361 kktsqlkwvl genmapekvd fedckdigdl kqydsdepep rslaswiqse fnkaceltds
421 swieldeige dvapiehias mrrnyftaev shcrateyim kgvyintall nascaamddf
481 qlipmiskcr tkegrrktnl ygfiikgrsh lrndtdvvnf vsmefsltdp rlephkweky
541 cvleigdmll rtaigqvsrp mflyirtngt skikmkwgme mrrcllqslq qiesmieaes
```

Figure 17 (continued)

```
601 svkekdmtke ffenksetwp igesprgvee gsigkvcrtl laksvfnsly aspqlegfsa
661 esrklllivq alrdnlepgt fdlgglyeai eeclindpwv llnaswfnsf lthalk
```

Figure 18

SEQ ID NO:23

```
   1 gaatggatgt caatccgacc ctactttttcc taaaagttcc agcgcaaaat gccataagca
  61 ccacattccc ttatactgga gatcctccat acagccatgg aacaggaaca ggatacacca
 121 tggacacagt caacagaaca catcaatatt cagaaaaagg gaagtggacg ataaacacag
 181 agactggggc accccagctc aacccgattg atggaccact acctgaggat aatgaaccaa
 241 gtggatatgc acaaacagaa tgtgttctgg aggccatggc tttccttgaa gagtcccacc
 301 cagggatatt tgagaattca tgccttgaaa caatggaagt tgttcaacaa caaggggtgg
 361 ataaactaac tcaaggtcgc caaacttatg attggacatt aaacagaaat caaccagcag
 421 caactgcatt ggccaacacc atagaagttt ttagatcgaa tagtctaaca gccaatgagt
 481 caggaagact aatagatttc ctaaaggatg taatggaatc aatggataga aagaaatgg
 541 agataacaac acactttcaa agaaaaagga gagtgagaga caacatgacc aagaagatgg
 601 tcacacaaag aacaatagga aagaaaaaac aaagattgag taagagaagt tatctaataa
 661 gagcacttac attgaatacg atgaccaaag atgcagagag aggcaaatta aaaagaaggg
 721 ctatcgcaac acccgggatg caaattagag ggttcgtgta ctttgttgag actttagcta
 781 ggagcatttg cgaaaagctt gaacagtctg gactcccagt aggggggaaat gaaaagaagg
 841 ccaaattggc aaatgttgtg agaaaaatga tgactaattc acaagacaca gagctttctt
 901 tcacaatcac tggggacaat actaagtgga tgaaaatca aaatcctcga atgttcctgg
 961 cgatgattac atatatcacc gaaatcaac ccgagtggtt cagaaacatc ctgagcatgg
1021 cacccataat gttttcaaac aaaaatggcaa gactaggaaa agggtacatg ttcgagagta
1081 aaaggatgaa gctccgaaca caaataccag cagaaatgct agcaagcatt gatctgaagt
1141 atttcaatga atcaacaagg aagaaaattg agaaaataag gcctcttcta atagatggca
1201 cagcatcatt gagccctgga atgatgatgg gcatgttcaa catgctaagt acggttttgg
1261 gagtctcgat actgaatctt ggacaaaaga aatacaccag gacaacatac tggtgggatg
1321 ggctccaatc ctccgacgat tttgccctca ttgtgaatgc accaaattat gagggaatac
1381 aagcaggagt gaatagattc tacaggacct gcaagttagt aggaataaac atgagcaaaa
1441 agaagtccta tataaataaa acagggacat tgaattcac aagcttttttt tatcgctatg
1501 ggtttgtggc taatttagc atggagctgc ccagttttgg agtgtctgga ataaatgaat
1561 cagctgatat gagtattgga gtaacagtga aaagaacaa tatgataaac aatgatcttg
1621 gacctgcaac agcccagatg gcccttcaat tgttcatcaa agactacaga tacacatata
1681 ggtgccacag aggagacaca caaattcaga cgagaagatc attcgagcta agaagctat
1741 gggatcaaac ccgatcaaat gcaggactat tagtatctga tggaggacca aacttataca
1801 atatcaggaa tcttcacatt cctgaagtct gcttaaaatg ggagctaatg gatgaggatt
1861 atcggggaag gctttgtaat cccctgaatc cttttgtcag ccataaagag attgattctg
1921 taaacaatgc tgtggtgatg ccagcccatg cccagccaa agcatggaa tatgatgccg
1981 ttgcaactac acactcctgg atccccaaga ggaatcgctc tattctcaac acaagccaaa
2041 ggggaattct tgaggatgaa cagatgtacc agaagtgctg caacctgttc gagaaatttt
2101 tccctagtag ttcatacagg agaccggttg gaatttctag catggtggag gccatggtgt
2161 ctagggcccg gattgatgcc agaatcgact tcgagtctgg acggattaag aaagaagagt
2221 tctctgagat cataaggatc tgttccacca ttgaagaact cagacggcaa acatgatgaa
2281 tttggcttgt ccttcatgaa aaatgccctt gtttctacta ataccgagac gatata
```

SEQ ID NO:31

```
   1 mdvnptllfl kvpaqnaist tfpytgdppy shgtgtgytm dtvnrthqys ekgkwtinte
  61 tgapqlnpid gplpedneps gyaqtecvle amafleeshp gifensclet mevvqqtrvd
 121 kltqgrqtyd wtlnrnqpaa talantievf rsnsltanes grlidflkdv mesmdreeme
 181 itthfqrkrr vrdnmtkkmv tqrtigkkkq rlskrsylir altlntmtkd aergklkrra
 241 iatpgmqirg fvyfvetlar sicekleqsg lpvggnekka klanvvrkmm tnsqdtelsf
 301 titgdntkwn enqnprmfla mityitrnqp ewfrnilsma pimfsnkmar lgkgymfesk
 361 rmklrtqipa emlasidlky fnestrkkie kirpllidgt aslspgmmmg mfnmlstvlg
 421 vsilnlgqkk ytrttywwdg lqssddfali vnapnyegiq agvnrfyrtc klvginmskk
 481 ksyinktgtf eftsffyryg fvanfsmelp sfgvsgines admsigvtvi knnminndlg
```

Figure 18 (continued)

```
541 pataqmalql fikdyrytyr chrgdtqiqt rrsfelkklw dqtrsnagll vsdggpnlyn
601 irnlhipevc lkwelmdedy rgrlcnplnp fvshkeidsv nnavvmpahg paksmeydav
661 atthswipkr nrsilntsqr giledeqmyq kccnlfekff psssyrrpvg issmveamvs
721 raridaridf esgrikkeef seiiricsti eelrrqt
```

Figure 19

SEQ ID NO:24

```
   1 tatattcaat atggagagaa taaaagaact aagagatcta atgtcgcagt cccgcactcg
  61 cgaaatcctc accaagacca ctgtggacca tatggccata atcaaaaagt acacatcagg
 121 aaggcaagag aagaaccctg cactcagaat gaagtggatg atggcaatga agtacccaat
 181 cacagcagac aagagaataa tggacatgat tccagagaga aatgaacaag acaaaccct
 241 ctggagcaaa acaaacgatg ctggatcgga ccgcgtgatg gtatcacccc tggctgtaac
 301 atggtggaat aggaatggcc caacagcaag cacagttcac taccctaagg tatataaaac
 361 ttatttcgaa aaagtcgaaa ggttaaaaca tggtaccttt ggccctgtcc acttcaggaa
 421 tcaagttaaa ataagaagga gagttgacac aaaccctggt cacgcagatc tcagtgccaa
 481 ggaggcacag gatgtgatca tggaagttgt tttcccaaat gaggtggggg caagaatact
 541 gacatcagag tcacagctga caataacaaa agagaagaaa gaagagctcc aggattgtaa
 601 aattgctccc ttaatggtgg catacatgct agaaaaagag ttggtccgta aaacgaggtt
 661 tctcccggtg gctggtggaa caggcagtgt ttatattgaa gtgctgcatt taactcaggg
 721 gacatgctgg gagcaaatgt acactccagg aggagaagtg agaaatgatg atgttgacca
 781 aagtttgatt attgctgcta gaaacatagt aagaagagca gcagtgtcag cagacccatt
 841 agcatctctt ttggaaatgt gccacagcac acagattgga ggaataagga tggtggacat
 901 ccttagacag aatccaacgg aggaacaagc cgtagacata tgcaaggcag caatggggct
 961 gaggattagc tcctctttca gctttggtgg gttcactttc aaaagaacaa gtgggtcatc
1021 agttaagaga gaagaagaag tgctcacggg caaccttcaa acactgaaaa taagagtaca
1081 tgaaggatat gaagaattca atggtcgg gagaagagca acagctattc tcagaaaagc
1141 aaccaggaga ttgatccagt taatagtaag tgggagagat gagcagtcaa ttgctgaggc
1201 aataattgtg gccatggtat tttcacaaga ggattgcatg atcaaggcag ttagggcga
1261 tctgaacttt gtcaataggg caaaccagcg actgaatccc atgcatcaac tcttgaggca
1321 tttccaaaaa gatgcaaaag tgcttttcca gaattgggga attgaaccca tcgacaatgt
1381 gatgggaatg atcgggatat gcccgatat gaccccaagc acggagatgt cgctgagagg
1441 gataagagtc agcaaaatgg gagtagatga atactccagc acagagagag tggtagtgag
1501 cattgacaga ttttgaggg tcgggatca acgagggaac gtactattgt ctcctgaaga
1561 ggtcagtgag acacaaggga cggagaaatt ggcaataact tattcgtcat cgatgatgtg
1621 ggagatcagt ggccctgagt cagtgctggt caacacttat caatggatca taaggaattg
1681 ggaaagtttg aaaattcaat ggtcacaaga tcccacgatg ttatacaaca aatggaatt
1741 tgaaccattt cagtctcttg tccctaaagc aaccagaagt cgttacagtg ggttcgtgag
1801 gacactgttc cagcaaatgc gggatgtgat tggaacattt gacactgtcc aaataataaa
1861 acttctcccc tttgctgctg ctccaccaga acagagtagg atgcagtttt cctcactgac
1921 tgtgaatgtg agaggatcag ggttgaggat actggtaaga ggcaattctc cagtattcaa
1981 ttacaataaa gcaaccaaaa ggcttacagt tcttggaaag gatgcaggtg aattgaccga
2041 agacccagat gaaggcacag ctggagtgga gtctgctgtc ctgagggat ttctcatttt
2101 gggcaaagaa gacaagagat atggtccagc attaagcatc aatgaactga gcaatcttgc
2161 aaaaggagag aaagctaatg tgctaattgg gcaaggagac gtagtgttgg taatgaaacg
2221 gaaacgggac tctagcatac ttactgacag ccagacagcg accaaaagaa ttcggacggc
2281 catcaattag tgtcgaa
```

SEQ ID NO:32

```
  1 merikelrdl msqsrtreil tkttvdhmai ikkytsgrqe knpalrmkwm mamkypitad
 61 krimdmiper neqgqtlwsk tndagsdrvm vsplavtwwn rngptastvh ypkvyktyfe
121 kverlkhgtf gpvhfrnqvk irrrvdtnpg hadlsakeaq dvimevvfpn evgariltse
181 sqltitkekk eelqdckiap lmvaymleke lvrktrflpv aggtgsvyie vlhltqgtcw
241 eqmytpggev rnddvdqsli iaarnivrra avsadplasl lemchstqig girmvdilrq
301 npteeqavdi ckaamglris ssfsfggftf krtsgssvkr eeevltgnlq tlkirvhegy
361 eeftmvgrra tailrkatrr liqlivsgrd eqsiaeaiiv amvfsqedcm ikavrgdlnf
421 vnranqrlnp mhqllrhfqk dakvlfqnwg iepidnvmgm igilpdmtps temslrgirv
481 skmgvdeyss tervvvsidr flrvrdqrgn vllspeevse tqgteklait ysssmmweis
```

Figure 19 (continued)

```
541 gpesvlvnty qwiirnwesl kiqwsqdptm lynkmefepf qslvpkatrs rysgfvrtlf
601 qqmrdvigtf dtvqiikllp faaappeqsr mqfssltvnv rgsglrilvr gnspvfnynk
661 atkrltvlgk dageltedpd egtagvesav lrgflilgke dkrygpalsi nelsnlakge
721 kanvligqgd vvlvmkrkrd ssiltdsqta tkrirtain
```

Figure 20

SEQ ID NO:41

```
   1 agcaaaagca ggggttatac catagacaac cgaacaaaga caatgaccat cactttctc
  61 atcctcctgt tcacagtagt gaaaggggac caaatatgta tcggatacca tgccaacaat
 121 tccacagaaa aagttgacac aatcttggaa cgaaacgtca ccgtgactca tgccaaggac
 181 attcttgaaa aaacgcataa tggaaagttg tgcagattaa gcgggatccc tccactggaa
 241 ctgggggatt gcagcattgc aggttggctc cttggaaatc cggaatgtga ccggctctta
 301 agtgtacctg aatggtccta tatagtggaa aaggaaaacc cggtgaatgg tctgtgctac
 361 ccaggcagtt tcaatgatta tgaggaattg aaacatctcc tcaccagtgt gacacacttt
 421 gagaaagtta agattctgcc cagagatcaa tggactcagc acacaacaac tggtggttct
 481 cgggcctgtg cagtgtctgg aaacccgtca ttctttagga catggtttg cttacaaag
 541 aagggggtcaa actacccaat gctaaaagg tcatacaaca acacaagtgg ggagcaaatg
 601 ctggtaatct ggggatacat catcccaat gacgatgcgg aacaaaggac actgtaccag
 661 aatgtgggaa catatgtttc cgttgggaca tcaacactaa ataagaggtc aatccctgaa
 721 atagcaacaa ggcccaaagt caatggacaa ggagggagaa tggaattctc ttggactcta
 781 ttggagacat gggatgtcat aaattttgag agcactggta atttaattgc accagaatac
 841 ggattcaaaa tatcaaagag aggaagctca ggaattatga gacagagaa aacacttgaa
 901 aattgtgaaa ccaaatgtca gaccccttg ggggcaataa atacaacatt gcccttcac
 961 aacattcacc cattgacaat aggtgagtgc cccaagtatg taaagtcaga cagactggtt
1021 ttggcaacag gactaagaaa tgtccctcag attgaatcaa ggggattgtt tggagcaata
1081 gctgggttta tagaaggcgg atggcaaggg atggttgatg gctggtatgg gtatcatcac
1141 agcaatgatc aaggatcagg atatgcagca gacaaagaat ccactcaaaa ggcaattgat
1201 gggataacta caaagtaaa ttctgtgatt gaaagatga acactcagtt tgaggctgtt
1261 gggaaagagt tcaacaatct agagagaaga ctagaaaact aaataaaaa gatggaagat
1321 ggatttcttg atgtatggac atataatgcc gaactcctag ttctaatgga gaatgagagg
1381 acacttgatt tccatgactc taatgtgaag aatctgtacg ataaggtcag aatgcaatta
1441 agagacaatg ctaaggaaat agggaacgga tgctttgagt tttatcataa atgtgatgat
1501 gaatgcatga atagtgtcag gaatggaaca tatgattatc caaatatga ggaagagtcc
1561 aagctgaaca ggaacgaaat aaaaggactg aaattgagca atatggggggt ctatcaaata
1621 cttgctatat acgctacagt gcaggctcc ttgtcactgg caatcatgat agctgggatt
1681 tctttctgga tgtgttctaa tgggtctctg caatgcagaa tttgcatatg actgtaagtc
1741 aatttgtaat taaaaacacc cttgtttcta ct
```

SEQ ID NO:42

```
   1 MTITFLILLF TVVKGDQICI GYHANNSTEK VDTILERNVT VTHAKDILEK THNGKLCRLS
  61 GIPPLELGDC SIAGWLLGNP ECDRLLSVPE WSYIVEKENP VNGLCYPGSF NDYEELKHLL
 121 TSVTHFEKVK ILPRDQWTQH TTTGGSRACA VSGNPSFFRN MVWLTKKGSN YPIAKRSYNN
 181 TSGEQMLVIW GIHHPNDDAE QRTLYQNVGT YVSVGTSTLN KRSIPEIATR PKVNGQGGRM
 241 EFSWTLLETW DVINFESTGN LIAPEYGFKI SKRGSSGIMK TEKTLENCET KCQTPLGAIN
 301 TTLPFHNIHP LTIGECPKYV KSDRLVLATG LRNVPQIESR GLFGAIAGFI EGGWQGMVDG
 361 WYGYHHSNDQ GSGYAADKES TQKAIDGITN KVNSVIEKMN TQFEAVGKEF NNLERRLENL
 421 NKKMEDGFLD VWTYNAELLV LMENERTLDF HDSNVKNLYD KVRMQLRDNA KEIGNGCFEF
 481 YHKCDDECMN SVRNGTYDYP KYEEESKLNR NEIKGLKLSN MGVYQILAIY ATVAGSLSLA
 541 IMIAGISFWM CSNGSLQCRI CI
```

Figure 21

SEQ ID NO:43

```
   1 tgcgagatga atccgaatca gaagataata acaatcgggg tagtgaatac cactctgtca
  61 acaatagccc ttctcattgg agtgggaaac ttagttttca acacagtcat acatgagaaa
 121 ataggagacc atcaaatagt gacccatcca acaataacga cccctgcagt accgaactgc
 181 agtgacacta taataacata caataacact gtgataaaca acataacaac aacaataata
 241 actgaagcag aaaggccttt caagtctcca ctaccgctgt gcccttcaa aggattcttc
 301 ccttttcaca aggacaatgc aatacgactg ggtgagaaca agacgtcat agtcacaagg
 361 gagccttatg ttagctgcga taatgacaac tgctggtcct tgctctcgc acaaggagca
 421 ttgctaggga ctaaacatag caatgggacc attaaagaca ggacaccata taggtctcta
 481 attcgtttcc caataggaac agctccagta ctgggaaatt acaaagagat atgcattgct
 541 tggtcgagca gcagttgctt tgacgggaaa gagtggatgc atgtgtgcat gacagggaac
 601 gataatgatg caagtgccca gataatatat ggagggagaa tgacagactc cattaaatca
 661 tggagaaagg acatactaag aacccaggag tctgaatgtc aatgcattga cgggacttgt
 721 gttgttgctg tcacagatgg ccctgctgct aatagtgcag accacagggt ttactggata
 781 cgggagggaa gaataataaa gtatgaaaat gttcccaaaa caaagataca acacttagaa
 841 gaatgttcct gctatgtgga cattgatgtt tactgtatat gtagggacaa ttggaagggc
 901 tctaacagac cttggatgag aatcaacaac gagactatac tggaaacagg tatgtatgt
 961 agtaaattcc actcagacac ccccaggcca gctgacccttt caacaatgtc atgtgactcc
1021 ccaagcaatg tcaatggagg acccggagtg aaggggtttg gtttcaaagc tggcaatgat
1081 gtatggttag gtagaacagt gtcaactagt ggtagatcgg gctttgaaat tatcaaagtt
1141 acagaagggt ggatcaactc tcctaaccat gtcaaatcaa ttacacaaac actagtgtcc
1201 aacaatgact ggtcaggcta ttcaggtagc ttcattgtca aagccaagga ctgttttcag
1261 ccctgttttt atgttgagct tatacgaggg aggcccaaca agaatgatga cgtctcttgg
1321 acaagtaata gtatagttac tttctgtgga ctagacaatg aacctggatc gggaggttgg
1381 ccggatggtt ctaacattgg gtttgtgccc aagtaataga aaaagca
```

SEQ ID NO:44

```
  1 MNPNQKIITI GVVNTTLSTI ALLIGVGNLV FNTVIHEKIG DHQIVTHPTI TTPAVPNCSD
 61 TIITYNNTVI NNITTTIITE AERPFKSPLP LCPFKGFFPF HKDNAIRLGE NKDVIVTREP
121 YVSCDNDNCW SFALAQGALL GTKHSNGTIK DRTPYRSLIR FPIGTAPVLG NYKEICIAWS
181 SSSCFDGKEW MHVCMTGNDN DASAQIIYGG RMTDSIKSWR KDILRTQESE CQCIDGTCVV
241 AVTDGPAANS ADHRVYWIRE GRIIKYENVP KTKIQHLEEC SCYVDIDVYC ICRDNWKGSN
301 RPWMRINNET ILETGYVCSK FHSDTPRPAD PSTMSCDSPS NVNGGPGVKG FGFKAGNDVW
361 LGRTVSTSGR SGFEIIKVTE GWINSPNHVK SITQTLVSNN DWSGYSGSFI VKAKDCFQPC
421 FYVELIRGRP NKNDDVSWTS NSIVTFCGLD NEPGSGGWPD GSNIGFVPK
```

H2N3 INFLUENZA A VIRUSES AND METHODS OF USE

CONTINUING APPLICATION DATA

This application claims the benefit of U.S. Provisional Application Ser. No. 60/959,333, filed Jul. 13, 2007, U.S. Provisional Application Ser. No. 60/961,072, filed Jul. 18, 2007, U.S. Provisional Application Ser. No. 60/961,930, filed Jul. 25, 2007, and U.S. Provisional Application Ser. No. 61/002,242, filed Nov. 7, 2007, each of which is incorporated by reference herein.

GOVERNMENT FUNDING

The present invention was made with government support under Grant No. CRIS 088, awarded by the NADC, USDA-ARS, Grant No. HHSN266200700005C, awarded by the NIH, and Grant No. U01 CI000357-01, awarded by the NIH. The Government has certain rights in this invention.

BACKGROUND

The inherent home of the worldwide reservoir of influenza A viruses is the wild waterfowl population (Hinshaw et al., 1982, In: Beare A S (ed). Basic and Applied Influenza Research, CRC Press, Boca Raton, La., pp. 79-104). Infection in water-based avian species is usually subclinical and confined to the intestinal tract. All subtypes of Type A influenza viruses have been detected in waterfowl, and the viruses are usually very stable genetically in these hosts. Influenza viruses have been shown to sporadically infect a wide variety of other host species, and such infection often results in disease (Webster et al., 1992, *Microbiol Rev* 56:152-179). Once established in a non-waterfowl species, influenza viruses are much less stable and mutation occurs more frequently (Bean et al., 1992, *J Virol* 66:1129-38). The viruses have been able to adapt to cause sustained infection in a few other species, most notably humans, pigs, horses and poultry. Characterization of the external proteins, hemagglutinin (HA) and neuraminidase (NA), allows influenza A viruses to be classified into 16 HA and 9 NA subtypes. All subtypes can be found in the waterfowl reservoir, but infection of other species appears to be limited to certain subtypes. Influenza viruses have a segmented genome and concurrent infection of a host with more than one virus can result in production of a new virus with a different constellation of genes that differ from either original virus, a process called reasssortment. Influenza viruses can cross into new host species intact or contribute to the appearance of a new subtype in that species through reassortment (Wright et al., 2001, Orthomyxoviruses. In: Knipe D M, Howley P M (eds). Fields Virology, 4th ed. Lippincott. Williams & Wilkins, Philadelphia, pp. 1533-1579). Either of these two scenarios can result in influenza pandemics within the new host species.

The influenza subtypes that have been able to establish and maintain infections in humans and swine are H1, H3, N1 and N2. Humans also can be infected with H2 influenza viruses, a subtype that has not been identified in swine. H2N2 influenza virus has not circulated in the human population for the past 40 years and is currently detected only in avian species (Liu et al., 2004, *Virus Genes* 29:81-86, Munster et al., 2007, *PLoS Pathog* 3:e61, Krauss et al., 2004, *Vector Borne Zoonotic Dis* 4:177-189). There are two distinct lineages of avian H2 influenza viruses. The Eurasian lineage is genetically more similar to human H2 viruses (Schafer et al., 1993, *Virology* 194:781-788) than the American lineage. Nevertheless, some H2 viruses isolated from North American shorebirds carry HA of the Eurasian lineage, suggesting interregional transmission of the H2 gene (Makarova et al., 1999, *J Gen Virol* 80 Pt 12:3167-3171). H2 subtypes are presently circulating in birds, especially migratory birds. A variety of influenza subtypes also have been recovered from domestic poultry, but only two subtypes (H5, H7) have been associated with severe disease. Such infections in poultry are systemic in nature rather than being limited to the intestinal tract.

Three human pandemics have occurred in the last century and all three appear to have been due to infection of humans with a virus of avian origin. The 1918 Spanish "flu" was caused by a virus that crossed into humans "in toto", while the 1957 Asian "flu" (H2N2) and 1968 Hong Kong "flu" (H3N2) were due to reassortment of an avian source virus with a virus pre-existent in the human population (Kawaoka et al., 1989, *J Virol* 63:4603-4608). Typically, infection of humans with an avian virus does not readily occur because of differences in cell receptors in the two species. Avian influenza viruses prefer to attach to N-acetylneuraminic acid-α2,3-galactose receptor moieties which are found in abundance in avian intestinal tracts but are few in number in human respiratory tracts. Viruses adapted to humans and swine prefer to attach to N-acetylneuraminic acid-α2,6-galactose receptor moieties which are in abundance in human respiratory tracts (Rogers et al., 1983, *Virol* 127:361-373). Swine are readily infected with both human and avian viruses because their respiratory tracts have an abundance of both receptors. Experimentally, swine have been found to be susceptible to infection with nearly all subtypes (Hinshaw et al., 1981, *Infect Immun* 34:354-361, Kida et al., 1994, *J Gen Virol* 75:2183-2188). New reassortant viruses have been recovered from swine experimentally infected with two different influenza viruses at the same time (Webster et al., 1973, *Virol* 51:149-162). Results of these studies and others resulted in the concept of swine as "mixing vessels" and the concern that swine may contribute to formation of pandemic viruses (Scholtissek, 1990, *Med Principles Pract* 2:65-71). The close association of humans, swine, ducks and poultry under agricultural conditions in Asia is thought to contribute to the tendency of new pandemics to arise from that part of the world.

Since 1997, influenza viruses in Asia have been a prominent concern in world news (Shortridge et al. 1998, *Virol* 20:331-342, Shortridge et al., 2000, *Vet Microbiol* 74:141-147, Lipatov, et al., 2004, *J Virol* 78: 8951-8959, Webster et al., 2005, *Arch Virol Suppl* 19:I 17-129). The appearance and uncontrolled spread of a H5N1 influenza virus and the apparent ability of the virus to infect humans with lethal consequences have raised concerns that this virus is a harbinger of the next worldwide influenza pandemic. The H5N1 virus also has characteristics unusual for influenza viruses in its ability to cause fatal infection in waterfowl, the usually subclinical reservoir for influenza viruses (Sturn-Ramirez et al., 2005, *J Virol* 17:11269-79), and to infect species usually not considered susceptible to influenza virus infection, i.e. felines (Kuiken et al., 2004, Science 306 (5694): 241). The virus is a reassortant of viruses that were circulating in several avian populations: geese, poultry and quail (Webster et al., 2006, *Emerg Infect Dis* 12:3-8). The H5N1 virus does not currently have the ability to spread readily between humans, but the possibility remains that through mutation or additional reassortment, the virus may acquire that contagious property. To date, infection of swine with the H5N1 influenza virus, while reported in southeast Asia, does not appear to occur frequently (Choi et al., 2005, *J Virol* 79:10821-5). However, infection of swine with this virus, even if it only occurs rarely, might result in genetic mutations that change its inherent characteristics or could contribute to reassortment that would give rise to a virus with pandemic potential.

Natural infection of swine with avian influenza viruses has been documented worldwide, either as intact viruses or as reassortment events. In the late 1970s, an avian H1N1 virus became widespread in swine populations in Europe and the United Kingdom, displacing the classic swine H1N1 virus that had been imported to that part of the world from the United States (Pensaert et al., 1981, *Bull World Health Org* 59:75-78). Multiple lineages of H1N1 virus were detected in swine in China in 1993 (Guan et al., 1996, *J Virol* 70:8041-8046). Some H3N2 viruses recovered from swine in Asia since the 1970s appear to be entirely of avian origin (Kida et al., 1988, *Virol* 162:160-166). More frequently, avian viruses contribute genes to new reassortant viruses found in swine. In 1993, influenza viruses that were reassortants of avian and human viruses were recovered from pigs in Italy (Castrucci et al., 1993, *Virol* 193:503-506). Since 1998, swine in the United States have been infected with triple reassortant viruses with NP, M and NS genes from the classic H1N1 swine virus; HA, NA and PB1 genes from human viruses; and PA and PB2 polymerase genes derived from an avian virus (Zhou et al., 1999, *J Virol* 73:8851-8856, Webby et al., 2000, *J Virol* 74:8243-8251, Webby et al., 2004, *Virus Res* 103:67-73). The mixed-source internal genes in this triple reassortant appear to have contributed to a virus that replicates efficiently in swine but is able to "mix and match" the genes for the external HA and NA proteins quite readily. Some studies have implicated avian polymerase genes in enabling influenza viruses to cross species boundaries and establish in new hosts (Kawaoka et al., 1989, *J Virol* 63:4603-4608, Gabriel et al., 2005, *Proc Natl Acad Sci USA* 102(51):18590-5). Although early studies indicated that avian influenza viruses of most subtypes could infect pigs, a pilot study with an H5N1 virus isolated from birds in Vietnam in 2004 revealed only mild infection and no spread of virus to contact pigs. A serologic study of 3175 pigs from the regions in Asia in which the H5N1 influenza virus was responsible for widespread death loss in poultry revealed only 8 (0.25%) sera with antibodies against the virus (Choi et al., 2005, *J Virol* 79:10821-5). An assessment of the ability of these viruses to infect swine and evaluation of the genetic changes that occur during such infection would provide information on the degree of risk that swine could contribute to the establishment of a new pandemic virus.

SUMMARY OF THE INVENTION

The present invention is based on the identification of an influenza type A virus that is subtype H2N3 and isolated from a mammal (swine). The H2N3 subtype has not been found in mammals before, and the H2N2 subtype has not been found in man since 1968. Susceptible mammalian species typically do not have immunity against this virus and may need to be vaccinated against this subtype, thus there is a need for vaccines that protect animals, including humans, from this virus. Likewise, there is a need for diagnostic assays that accurately detect this virus and distinguish between other influenza A viruses.

The present invention provides isolated influenza A virus. The virus may replicate in a mammal, such as a pig, a mouse, or a ferret. A virus of the present invention may be present as a composition that also includes a pharmaceutically acceptable carrier.

A virus of the present invention may include a hemagglutinin subtype H2 or a neuraminidase subtype N3. The virus may contain both a hemagglutinin subtype H2 or a neuraminidase subtype N3. The hemagglutinin includes an amino acid sequence having at least 91% identity with SEQ ID NO:9 or SEQ ID NO:25, and the neuraminidase includes an amino acid sequence having at least 99% identity with SEQ ID NO:11 or SEQ ID NO:27.

A virus of the present invention may include a reverse complement of a polynucleotide encoding a hemagglutinin subtype H2, wherein the polynucleotide includes a nucleotide sequence having at least 91% identity with SEQ ID NO:1 or SEQ ID NO:17. A virus of the present invention may include a reverse complement of a polynucleotide encoding a neuraminidase subtype N3, wherein the polynucleotide includes a nucleotide sequence having at least 99% identity with SEQ ID NO:3 or SEQ ID NO:19. Examples of viruses include virus SW_2124514 deposited with the American Type Culture Collection under number PTA-8545 in accordance with the provisions of the Budapest Treaty, and virus SW_4296424 deposited with the American Type Culture Collection under number PTA-8545 in accordance with the provisions of the Budapest Treaty.

Also provided by the present invention are isolated polypeptides. A polypeptide of the present invention may be present as a composition that includes a pharmaceutically acceptable carrier. A polypeptide may be a hemagglutinin or a fragment thereof, wherein the isolated hemagglutinin includes an amino acid sequence, and wherein the amino acid sequence and the amino acid sequence of SEQ ID NO:9 or SEQ ID NO:25 have at least 91% identity. A hemagglutinin of the present invention typically binds to a mammalian cell. A polypeptide may be a neuraminidase or a fragment thereof, wherein the isolated neuraminidase includes an amino acid sequence, wherein the amino acid sequence and the amino acid sequence of SEQ ID NO:11 or SEQ ID NO:27 have at least 99% identity.

The present invention further provides isolated polynucleotides. A polynucleotide of the present invention may be present in a vector, and the vector may be present in a cell. The present invention also includes such vectors and cells. An isolated polynucleotide may include (a) a nucleotide sequence encoding a hemagglutinin, wherein the amino acid sequence of the hemagglutinin and the amino acid sequence of SEQ ID NO:9 or SEQ ID NO:25 have at least 91% identity and the hemagglutinin binds a mammalian cell, (b) the full complement of the nucleotide sequence of (a), (c) the full reverse complement of the nucleotide sequence of (a), or (d) the full complement of the nucleotide sequence of (c). An isolated polynucleotide may include (a) a nucleotide sequence encoding a neuraminidase, wherein the amino acid sequence of the neuraminidase and the amino acid sequence of SEQ ID NO:11 or SEQ ID NO:27 have at least 99% identity, (b) the full complement of the nucleotide sequence of (a), (c) the full reverse complement of the nucleotide sequence of (a), or (d) the full complement of the nucleotide sequence of (c).

The present invention also provides antibody. The antibody may be polyclonal or monoclonal, and an antibody of the present invention may be present as a composition that includes a pharmaceutically acceptable carrier. An antibody of the present invention may specifically bind a hemagglutinin subtype H2, wherein the hemagglutinin subtype H2 includes an amino acid SEQ ID NO:9, SEQ ID NO:25, or a fragment thereof, and wherein the antibody does not bind to other known H2 hemagglutinins, such as a polypeptide having an amino acid sequence SEQ ID NO:42. An antibody An antibody of the present invention may specifically bind a neuraminidase subtype N3, wherein the neuraminidase subtype N3 includes an amino acid SEQ ID NO:11, SEQ ID NO:27, or a fragment thereof, and wherein the antibody does not bind to other known N3 neuraminidases, such as a polypeptide having an amino acid sequence SEQ ID NO:44.

Methods for making antibody are also provided. The antibody may be polyclonal or monoclonal, and the invention also includes the antibody produced by the method. The methods may include administering to an animal a hemagglutinin in an amount effective to cause the production of an antibody specific for the hemagglutinin, wherein the hemagglutinin includes an amino acid sequence having at least 91% identity with SEQ ID NO:9 or SEQ ID NO:25, wherein the hemagglutinin binds to a mammalian cell. The methods may include administering to an animal a neuraminidase in an amount effective to cause the production of an antibody specific for the neuraminidase, wherein the neuraminidase includes an amino acid sequence having at least 99% identity with SEQ ID NO:11 or SEQ ID NO:27.

The present invention provides methods for assaying pathogenesis of an influenza A virus. The method may include administering to an animal an influenza A virus that includes a hemagglutinin subtype H2, and identifying the presence of signs associated with influenza A virus infection in the animal. The hemagglutinin may include an amino acid sequence having at least 91% identity with SEQ ID NO:9 or SEQ ID NO:25. The animal may be a mammal, such as a pig, a mouse, a bird, or a ferret. The virus may further include a neuraminidase subtype N3, wherein the neuraminidase includes an amino acid sequence having at least 99% identity with SEQ ID NO:11 or SEQ ID NO:27.

The present invention provides methods for assaying transmissibility of an influenza A virus. The method may include administering to a first animal an influenza A virus that includes a hemagglutinin subtype H2, placing a sentinel animal near the first animal, and identifying the presence of signs associated with influenza A virus infection in the sentinel animal. The hemagglutinin may include an amino acid sequence having at least 91% identity with SEQ ID NO:9 or SEQ ID NO:25. The first animal and the sentinel animal may be mammals, such as a pig, a mouse, a bird, or a ferret. The first animal and the sentinel may be independently selected from a pig, a mouse, a bird, or a ferret.

Also provided by the present invention are methods for detecting the presence of an influenza A virus. The method may include amplifying a target polynucleotide by contacting the target polynucleotide with a primer pair under suitable conditions to result in an amplified product, wherein the primer pair amplifies a target nucleotide comprising SEQ ID NO:1 or SEQ ID NO:17 and does not amplify a target nucleotide encoding other known H2 hemagglutinins, such as a target polynucleotide comprising SEQ ID NO:41, and detecting the amplified product, wherein the presence of the amplified product is indicative of the presence of an influenza A virus. The method may include amplifying a target polynucleotide by contacting the target polynucleotide with a primer pair under suitable conditions to result in an amplified product, wherein the primer pair amplifies a target nucleotide comprising SEQ ID NO:3 or SEQ ID NO:19 and does not amplify a target nucleotide encoding other known N3 neuraminidases, such as a target polynucleotide comprising SEQ ID NO:43, and detecting the amplified product, wherein the presence of the amplified product is indicative of the presence of an influenza A virus subtype H2N3. The target polynucleotide may be present in a biological sample. The target polynucleotide may be from an influenza virus obtained from a pig.

Other methods for detecting the presence of an influenza A virus are also provided. For instance, a method may include contacting a biological sample with an antibody of the present invention under conditions to form a complex with an influenza A virus, and detecting the complex, wherein the presence of the complex indicates the presence of an influenza A virus. A biological sample may be obtained from a pig.

Methods for detecting antibody to an influenza A virus are provided. The methods may include performing a hemagglutination inhibition test, wherein the test includes use of serum obtained from an animal, mammalian red blood cells, and an influenza A virus including a hemagglutinin, wherein the hemagglutinin includes an amino acid sequence having at least 91% identity with SEQ ID NO:9 or SEQ ID NO:25, and detecting inhibition of hemagglutination, wherein the inhibition of hemagglutination indicates the animal was exposed to an influenza A virus. The influenza virus used in the test may be SW_2124514 or SW_4296424.

Also provided by the present invention are methods for treating an animal at risk of infection with an influenza A virus. A method may include administering to the animal a composition having an inactivated influenza A virus, wherein the inactivated influenza A virus includes a hemagglutinin subtype H2, a neuraminidase subtype N3, or the combination thereof. The hemagglutinin may include an amino acid sequence having at least 91% identity with SEQ ID NO:9 or SEQ ID NO:25. The neuraminidase may include an amino acid sequence having at least 99% identity with SEQ ID NO:11 or SEQ ID NO:27. The influenza A virus may replicate in a mammal before inactivation. The influenza A virus may be chemically inactivated. The animal may be a pig, a bird, or a human. A method may include administering to the animal a composition having an attenuated influenza A virus, wherein the attenuated influenza A virus includes a hemagglutinin subtype H2, a neuraminidase subtype N3, or the combination thereof. The hemagglutinin may include an amino acid sequence having at least 91% identity with SEQ ID NO:9 or SEQ ID NO:25. The neuraminidase may include an amino acid sequence having at least 99% identity with SEQ ID NO:11 or SEQ ID NO:27. The influenza A virus may replicate in a mammal before attenuation. The influenza A virus may be cold adapted. The animal may be a pig, a bird, or a human.

The present invention also provides methods for treating an animal at risk of infection with an influenza A virus including administering to the animal a composition that includes a vector, wherein the vector includes a polynucleotide encoding a hemagglutinin or a fragment thereof when present in a cell, wherein the amino acid sequence of the hemagglutinin and the amino acid sequence of SEQ ID NO:9 or SEQ ID NO:25 have at least 91% identity, and wherein the hemagglutinin binds to a mammalian cell. The vector may be present in a virus. The animal may be a pig, a bird, or a human.

The present invention further provides methods for treating an animal at risk of infection with an influenza A virus including administering to the animal, such as a pig, a bird, or a human, a composition that includes a hemagglutinin or a fragment thereof, wherein the amino acid sequence of the hemagglutinin and the amino acid sequence of SEQ ID NO:9 or SEQ ID NO:25 have at least 91% identity, and wherein the hemagglutinin binds to a mammalian cell.

Also provided by the present invention are compositions. A composition may include an influenza A virus and a pharmaceutically acceptable carrier, wherein the influenza virus includes a hemagglutinin subtype H2, a neuraminidase subtype N3, or the combination thereof. The hemagglutinin may include an amino acid sequence having at least 91% identity with SEQ ID NO:9 or SEQ ID NO:25, the neuraminidase may include an amino acid sequence having at least 99% identity with SEQ ID NO:11 or SEQ ID NO:27, and the isolated influenza A virus may replicate in a mammal. The virus may be inactivated or attenuated. The composition may further include a second influenza A virus, such as an inactivated or attenuated influenza virus. The influenza A virus may be disrupted.

The present invention also includes kits. A kit may include packaging materials, and an antibody that specifically binds a hemagglutinin comprising an amino acid SEQ ID NO:9 or SEQ ID NO:25, an antibody that specifically binds neuraminidase comprising an amino acid SEQ ID NO:11 or SEQ ID NO:27, or a combination thereof. A kit may include packaging materials, and a primer pair that amplifies a target nucleotide comprising SEQ ID NO:1 or SEQ ID NO:17 and does not amplify a target nucleotide comprising SEQ ID NO:41, a primer pair that amplifies a target nucleotide comprising SEQ ID NO:3 or SEQ ID NO:19 and does not amplify a target nucleotide comprising SEQ ID NO:43, or a combination thereof.

DEFINITIONS

As used herein, the terms "virus particle" and "virus" are used interchangeably and refer to an influenza A particle, preferably a subtype H2N3 particle. A virus particle includes RNA polynucleotides that will in some aspects reproduce in a cell, an envelope that surrounds the polynucleotide, and the polypeptides hemagglutinin and neuraminidase present.

As used herein, "isolated" refers to a substance that has been removed from its natural environment, produced using recombinant techniques, or chemically or enzymatically synthesized. For instance, a polypeptide, polynucleotide, or virus of this invention may be isolated. Preferably, a polypeptide, polynucleotide, or virus of this invention is purified, i.e., is at least 60% free, preferably at least 75% free, and most preferably at least 90% free from other components with which they are naturally associated.

As used herein, the term "polynucleotide" refers to a polymeric form of nucleotides of any length, either ribonucleotides or deoxynucleotides, and includes both double- and single-stranded RNA and DNA. A polynucleotide may include nucleotide sequences having different functions, including for instance coding regions, and non-coding regions such as regulatory regions. A polynucleotide may be obtained directly from a natural source, or may be prepared with the aid of recombinant, enzymatic, or chemical techniques. A polynucleotide may be linear or circular in topology. A polynucleotide may be, for example, a portion of a vector, such as an expression or cloning vector, or a fragment.

As used herein, a "recombinant polynucleotide" refers to a polynucleotide having sequences that are not naturally joined together. The sequences may be joined by the artificial manipulation of different polynucleotide sequences using recombinant techniques, or may be chemically or enzymatically synthesized. A recombinant polynucleotide may be included in a suitable vector.

"Polypeptide" as used herein refers to a polymer of amino acids and does not refer to a specific length of a polymer of amino acids. The term "polypeptide" also includes molecules which contain more than one polypeptide joined by disulfide bonds, ionic bonds, or hydrophobic interactions, or complexes of polypeptides that are joined together, covalently or noncovalently, as multimers (e.g., dimers, tetramers). Thus, for example, the terms peptide, oligopeptide, protein, and enzyme are included within the definition of polypeptide. This term also includes post-expression modifications of the polypeptide, for example, glycosylations, acetylations, phosphorylations and the like.

As used herein, an "immunogenic polypeptide" refers to a polypeptide which, when introduced into an animal, induces an immune response in the animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells directed specifically to an epitope or epitopes of the polypeptide.

As used herein, a polypeptide "fragment" includes any polypeptide which retains at least some of the immunogenicity of the corresponding native polypeptide. Examples of fragments of polypeptides described herein include, but are not limited to, proteolytic fragments and deletion fragments. Polypeptide fragments further include any portion of the polypeptide which includes an immunogenic epitope of the native polypeptide, including linear as well as three-dimensional epitopes.

As used herein, the term "replication competent" refers to a virus particle that replicates when present in a cell. The cell may be ex vivo or in vivo. "Ex vivo" refers to a cell that has been removed from the body of an animal. Ex vivo cells include, for instance, primary cells (e.g., cells that have recently been removed from a animal and are capable of limited growth in tissue culture medium), and cultured cells (e.g., cells that are capable of long term culture in tissue culture medium). "In vivo" refers to cells that are present within the body of an animal. Typically, replication of a virus particle in a cell results in the production of additional viral particles.

As used herein, an antibody that can "specifically bind" or is "specific for" a virus and/or a polypeptide is an antibody that interacts only with an epitope of the antigen that induced the synthesis of the antibody, or interacts with a structurally related epitope. As used herein, the term "complex" refers to the combination of an antibody and a virus and/or a polypeptide that results when an antibody specifically binds to a virus and/or a polypeptide.

As used herein, "treatment" and "treating" refer to the use of a composition of the present invention to prevent, cure, retard, or reduce the severity of influenza disease signs in an animal, and/or result in no worsening of influenza disease over a specified period of time in an animal which has already been exposed to influenza A virus and is thus in need of therapy. As used herein, the term "signs" of infection refer to objective evidence in an animal of a condition caused by infection by an influenza A virus. Signs of infection by an influenza A virus herein and the evaluation of such signs are routine and known in the art.

As used herein, a "biological sample" refers to a sample of obtained from a animal, including but not limited to, for example, nasal or ocular discharge, sputum, blood, lymph, lung, bronchioalveolar lavage fluid, tracheal swab, tracheal wash, or respiratory tract tissue or swabs. The sample may be, for instance, tissue or fluid, and may be obtained by routine methods. A "biological sample" also includes samples of cell culture constituents including but not limited to the cells and media resulting from the growth of cells and tissues in culture medium or in an egg. The cells may be infected with a virus of the present invention or may contain a vector that encodes a polypeptide of the present invention.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

BRIEF DESCRIPTION OF THE FIGURES

FIG. 1. Phylogenetic trees of selected influenza virus H2 (a) and N3 (b) genes based on the nucleotide sequences of the ORFs. Horizontal distance is proportional to genetic distance. The trees are rooted to A/duck/Singapore/97 H5N3 (a) and A/tern/Astrakan/775/83 H3N3 (b). Numbers below nodes represent bootstrap values from 200 replicates.

FIG. 2. Microscopic lung sections from control and infected pigs. (a) Bronchiole in the lung of a control pig inoculated with noninfectious cell culture supernatant. Note the regular outline of the pseudostratified columnar epithelium. (b) Necrotizing bronchiolitis in the lung of a pig 3 days after inoculation with H2N3 swine influenza virus. The epithelial lining of the airway is focally disrupted by sloughing of necrotic infected cells and early reactive proliferation of the remaining epithelium. The lumen contains sloughed epithelial cells and mixed leukocytes. A small number of lymphocytes are seen infiltrating subepithelial and peribronchiolar connective tissue.

FIG. 3. Microscopic lung sections from control and infected mice. (a) Bronchiole in the lung from a control mouse. Note the regular outline of a uniform single to pseudostratified layer of cuboidal epithelial cells. Pneumocytes lining alveolar walls are inconspicuous. (b) Marked proliferative alveolitis in the lung of a mouse 10 days after inoculation with $10^6$ $TCID_{50}$ of H2N3 swine influenza virus. (c) Epithelial necrosis and proliferation in an airway and proliferative alveolitis in the lung of a mouse 10 days after inoculation with $10^6$ $TCID_{50}$ of H2N3 swine influenza virus.

FIG. 4. Nucleotide sequence (SEQ ID NO:1, GenBank Accession No. EU258939) of segment 4 of SW/2124514 and polypeptide (SEQ ID NO:9, GenPept Accession No. ABY40433) encoded by nucleotides 59-1747 (SEQ ID NO:37).

FIG. 5. Nucleotide sequence (SEQ ID NO:2, GenBank Accession No. EU258938) of segment 7 of SW/2124514 and polypeptides encoded by nucleotides 7-765 (SEQ ID NO:10, GenPept Accession No. ABY40431) and encoded by nucleotides 7-32 and 721-988 (SEQ ID NO:45, GenPept Accession No. ABY40432).

FIG. 6. Nucleotide sequence (SEQ ID NO:3, GenBank Accession No. EU258937) of segment 6 of SW/2124514 and polypeptide (SEQ ID NO:11, GenPept Accession No. ABY40430) encoded by nucleotides 5-1414 (SEQ ID NO:39).

FIG. 7. Nucleotide sequence (SEQ ID NO:4, GenBank Accession No. EU258936) of segment 5 of SW/2124514 and polypeptide (SEQ ID NO:12, GenPept Accession No. ABY40429) encoded by nucleotides 27-1523.

FIG. 8. Nucleotide sequence (SEQ ID NO:5, GenBank Accession No. EU258935) of segment 8 of SW/2124514 and polypeptide encoded by nucleotides 13-672 (SEQ ID NO:13, GenPept Accession No. ABY40427) and encoded by nucleotides 13-42 and 515-850 (SEQ ID NO:46, GenPept Accession No. ABY40428).

FIG. 9. Nucleotide sequence (SEQ ID NO:6, GenBank Accession No. EU258940) of segment 3 of SW/2124514 and polypeptide (SEQ ID NO:14, GenPept Accession No. ABY40434) encoded by nucleotides 6-2156.

FIG. 10. Nucleotide sequence (SEQ ID NO:7, GenBank Accession No. EU258941) of segment 2 of SW/2124514 and polypeptide (SEQ ID NO:15, GenPept Accession No. ABY40435) encoded by nucleotides 5-2278.

FIG. 11. Nucleotide sequence (SEQ ID NO:8, GenBank Accession No. EU258942) of segment 1 of SW/2124514 and polypeptide (SEQ ID NO:16, GenPept Accession No. ABY40436) encoded by nucleotides 11-2290.

FIG. 12. Nucleotide sequence (SEQ ID NO:17, GenBank Accession No. EU258943) of segment 4 of SW/4296424 and polypeptide (SEQ ID NO:25, GenPept Accession No. ABY40437) encoded by nucleotides 59-1747 (SEQ ID NO:38).

FIG. 13. Nucleotide sequence (SEQ ID NO:18, GenBank Accession No. EU258944) of segment 7 of SW/4296424 and polypeptide encoded by nucleotides 9-767 (SEQ ID NO:26, GenPept Accession No. ABY40438) and encoded by nucleotides 9-34 and 723-990 (SEQ ID NO:47, GenPept Accession No. ABY40439).

FIG. 14. Nucleotide sequence (SEQ ID NO:19, GenBank Accession No. EU258945) of segment 6 of SW/4296424 and polypeptide (SEQ ID NO:27, GenPept Accession No. ABY40440) encoded by nucleotides 3-1412 (SEQ ID NO:40).

FIG. 15. Nucleotide sequence (SEQ ID NO:20, GenBank Accession No. EU258946) of segment 5 of SW/4296424 and polypeptide (SEQ ID NO:28, GenPept Accession No. ABY40441) encoded by nucleotides 31-1527.

FIG. 16. Nucleotide sequence (SEQ ID NO:21, GenBank Accession No. EU258947) of segment 8 of SW/4296424 and polypeptides encoded by nucleotides 11-670 (SEQ ID NO:29, GenPept Accession No. ABY40442) and encoded by nucleotides 11-40 and 513-848 (SEQ ID NO:48, GenPept Accession No. ABY40443).

FIG. 17. Nucleotide sequence (SEQ ID NO:22, GenBank Accession No. EU258948) of segment 3 of SW/4296424 and polypeptide (SEQ ID NO:30, GenPept Accession No. ABY40444) encoded by nucleotides 10-2160.

FIG. 18. Nucleotide sequence (SEQ ID NO:23, GenBank Accession No. EU258949) of segment 2 of SW/4296424 and polypeptide (SEQ ID NO:31, GenPept Accession No. ABY40445) encoded by nucleotides 3-2276.

FIG. 19. Nucleotide sequence (SEQ ID NO:24, GenBank Accession No. EU258950) of segment 1 of SW/4296424 and polypeptide (SEQ ID NO:32, GenPept Accession No. ABY40446) encoded by nucleotides 11-2290.

FIG. 20. Nucleotide sequence (SEQ ID NO:41) of hemagglutinin having Genbank Accession number CY003992 and polypeptide (SEQ ID NO:42) encoded thereby (Genbank Accession number ABB18080).

FIG. 21. Nucleotide sequence (SEQ ID NO:43) of neuraminidase having Genbank Accession number DQ236167 and polypeptide (SEQ ID NO:44) encoded thereby (Genbank Accession number ABB80526).

DETAILED DESCRIPTION OF ILLUSTRATIVE EMBODIMENTS

The present invention includes isolated influenza A viruses. An influenza A virus includes 8 segments of linear negative-sense single stranded RNA. An influenza A virus of the present invention may include a segment that contains a coding region encoding a subtype H2 hemagglutinin (also referred to herein as H2 hemagglutinin). Such a segment is often referred to in the art as segment 4. Examples of segments encoding a subtype H2 hemagglutinin and present in a virus of the present invention include, but are not limited to, the reverse complement of SEQ ID NO:1 and the reverse complement of SEQ ID NO:17. An influenza A virus of the present invention may include a segment that contains a coding region encoding a subtype N3 neuraminidase (also referred to herein as N3 neuraminidase). Such a segment is often referred to in the art as segment 6. Examples of segments encoding a subtype N3 neuraminidase and present in a virus of the present invention include, but are not limited to, the reverse complement of SEQ ID NO:3 and the reverse complement of SEQ ID NO:19. Subtype H2 hemagglutinins and subtype N3 neuraminidases are described below. Preferably, a virus of the present invention includes a segment that contains a coding region encoding a subtype H2 hemagglutinin and a segment that contains a coding region encoding a subtype N3 neuraminidase.

An influenza A virus of the present invention also includes 6 other RNA segments, one encoding M1 and M2 polypeptides, one encoding an NP polypeptide, one encoding NS1 and NS2 polypeptides, one encoding a PA polypeptide, one encoding a PB1 polypeptide, and one encoding a PB2 polypeptide. The PB1 segment may encode other polypeptides, e.g., PB1-F2 polypeptide. Examples of segments encoding an M polypeptide include, but are not limited to, the reverse complement of SEQ ID NO:2 and the reverse complement of SEQ ID NO:18. Examples of segments encoding an NP polypeptide include, but are not limited to, the reverse complement of SEQ ID NO:4 and the reverse complement of SEQ ID NO:20. Examples of segments encoding an NS polypeptide include, but are not limited to, the reverse complement of SEQ ID NO:5 and the reverse complement of SEQ ID NO:21. Examples of segments encoding a PA polypeptide include, but are not limited to, the reverse complement of SEQ ID NO:6 and the reverse complement of SEQ ID NO:22. Examples of segments encoding a PB1 polypeptide include, but are not limited to, the reverse complement of SEQ ID NO:7 and the reverse complement of SEQ ID NO:23. Examples of segments encoding a PB2 polypeptide include, but are not limited to, the reverse complement of SEQ ID NO:8 and the reverse complement of SEQ ID NO:24.

While a virus of the present invention includes 8 segments, such a virus may have any combination of the segments described herein, including 1, 2, 3, 4, 5, 6, 7, or 8 of the segments described herein. For instance, a virus of the present invention may include the reverse complement of SEQ ID NO:1, SEQ ID NO:2, SEQ ID NO:3, SEQ ID NO:4, SEQ ID NO:5, SEQ ID NO:6, SEQ ID NO:7, and SEQ ID NO:8 (referred to herein as virus SW_2124514), or the reverse complement of SEQ ID NO:17, SEQ ID NO:18, SEQ ID NO:19, SEQ ID NO:20, SEQ ID NO:21, SEQ ID NO:22, SEQ ID NO:23, and SEQ ID NO:24 (referred to herein as virus SW_4296424). A virus of the present invention may include none of the segments described herein. For instance, the present invention includes a virus with a segment encoding an H2 hemagglutinin described herein, and/or a segment encoding a N3 neuraminidase described herein, and those segments may be segments other than the reverse complement of SEQ ID NO:1, SEQ ID NO:3, SEQ ID NO:17, SEQ ID NO:19.

Other viruses encoding an H2 hemagglutinin of the present invention and/or a N3 neuraminidase of the present invention and including other segments may be obtained by reassortment. Reassortant influenza viruses may be readily obtained using routine methods. For instance, a subset of vectors corresponding to genomic segments of a master influenza virus may be introduced, in combination with complementary segments derived from strains of interest. Typically, the master strains are selected on the basis of desirable properties relevant to vaccine administration. For example, for vaccine production, e.g., for production of a live attenuated vaccine, a master donor virus strain may be selected for an attenuated phenotype, cold adaptation and/or temperature sensitivity.

An influenza A virus of the present invention may be replication competent. In other aspects, an influenza A virus of the present invention is not replication competent, and an example of such a virus is an inactivated influenza A virus. Inactivated influenza A viruses are described below. Ex vivo cells that may be used as host cells for replication of an influenza A virus include, for instance, vertebrate cells, such as avian cells, in particular embryo cells from an embryonated egg. Other examples include mammalian cells, such as hamster cells, monkey cells, or dog cells. Preferably, mammalian cells are kidney cells or cell lines derived from such cells. A preferred example of a mammalian kidney cells are Madin-Darby canine kidney (MDCK) cells or cells from a clone of MDCK, MDCK-like cells, monkey kidney cells such as AGMK cells including Vero cells, suitable pig cell lines, or any other mammalian cell type suitable for the replication of influenza A virus. Suitable cells also include human cells, e.g. MRC-5 or Per-C6 cells, and avian cell lines. Suitable cells are not limited to cell lines; for example primary cells may be used. Avian embryo cells, such as chicken embryo fibroblasts, may be used in cell culture, or may be present in an embryonated egg. Methods and conditions for replicating influenza A virus in ex vivo cells are routine and known in the art. Whether an influenza virus is replicating in cultured cells can be easily determined using routine methods, such as by observing cytopathic effects. Ex vivo replication may also be used to produce large amounts of virus for use in, for instance, vaccines using routine and known methods.

An influenza A virus of the present invention may be replication competent in in vivo cells. The in vivo cells may be present in a vertebrate, such as a mammal including, but not limited to, pigs, mice, and ferrets, or an avian. It is believed that an influenza A virus of the present invention may be able to infect humans. Methods and conditions for replicating influenza A virus in an animal are routine and known in the art, as are methods for determining whether an influenza A virus is pathogenic. Whether an influenza virus is replicating in an animal can be easily determined using routine methods, such as, for instance, by observing viral load in the animal's sinuses, lungs, trachea, or observing pathology associated with infection by influenza A virus. For instance, histopathologic examination can be done using trachea and/or lung tissue.

An influenza A virus of the present invention is also able to be transmitted by contact between animals including, but not limited to, pigs and ferrets. Animal models for testing pathogenicity and transmissibility of influenza type A viruses are known to the person skilled in the art and are used routinely.

An influenza A virus of the present invention may be obtained from an animal, preferably an animal presenting signs of influenza A infection. The signs of such an infection vary depending upon the animal, and are known to the person skilled in the art. For instance, a pig infected with influenza A (swine influenza) typically presents with signs including coughing, sneezing, nasal or ocular discharge, dyspnea, lethargy, fever, anorexia, or a combination thereof. The lung or other tissue (such as nasal tissue or nasal swabs, tracheal swabs, bronchio-alveolar lavage fluid) may then be homogenized with a pharmaceutically acceptable aqueous solution (such as physiological saline, Ringers solution, Hank's Balanced Salt Solution, Minimum Essential Medium, and the like). The virus may be separated (e.g., isolated) using routine methods know in the art. Such methods include, for instance, low speed centrifugation of a homogenate, and passing a homogenate through filters with pore diameters in a micron range to remove contaminants. Typically, a virus particle is then grown in vivo (i.e., within the body of an animal or embryonated egg) or ex vivo to produce more virus particles. This process of transferring a small number of virus particles to a new environment for continued reproduction of the virus is referred to herein as passaging. Passaging may include, but is not limited to, transfer of virus particles from an infected animal to a non-infected animal, and from an infected cell culture to a non-infected cell culture.

A virus of the present invention may be inactivated, i.e., rendered incapable of reproducing in vivo and/or in cell culture. Methods of influenza A virus inactivation are known to the person skilled in the art and are used routinely. Examples include, for instance, treatment of a virus of the invention with heat, a standard chemical inactivating agent such as an aldehyde reagent including formalin, acetaldehyde and the like; reactive acidic alcohols including cresol, phenol and the like; acids such as benzoic acid, benzene sulfonic acid and the like; lactones such as beta-propiolactone and caprolactone; amines such as binary ethyleneimine and the like; and activated lactams, carbodiimides and carbonyl diheteroaromatic compounds such as carbonyl diimidazole. Treatment by heat or irradiation such as with ultraviolet and gamma irradiation may also be used to inactivate the virus.

Attenuated influenza A viruses and methods for making attenuated influenza A viruses are also included in the present invention. Attenuated viruses are able to replicate in an animal and induce an immune response, but generally are not pathogenic and have a reduced ability to cause the clinical signs of influenza in an animal. Methods of producing an attenuated virus are routine and known to the art. For instance, a virus of the present invention may be passaged under various conditions, e.g., used to infect an embryonated egg or a cell in culture, allowed to reproduce, and then harvested. This process is repeated until the virulence of the virus in an animal, for instance pigs, is decreased. Another example includes viruses adapted to grow at lower temperatures and not grow as well at higher temperatures. Such attenuated viruses are often referred to as cold-adapted viruses, and may be produced by various routine methods, including reassortment with existing cold-adapted influenza A viruses (Younger et al., U.S. Pat. No. 5,149,53, Dowling et al., U.S. Patent Application 20070092536). In another example, a virus of the present invention may be attenuated by mutation of a coding region, e.g., the coding region encoding a polypeptide, such as the non-structural polypeptide NS1 (Palese et al., WO 2006/083286, Egorov et al., U.S. Pat. No. 6,866,853).

The viruses SW_2124514 and SW_4296424 were deposited with American Type Culture Collection (ATCC), Manassas, Va., on Jul. 24, 2007. SW_2124514 (also referred to herein as SW/2124514) was subsequently granted ATTC Patent Deposit Designation PTA-8545, and SW 4296424 (also referred to herein as SW/4296424) was subsequently granted ATTC Patent Deposit Designation PTA-8546. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

An influenza A virus of the present invention may include a hemagglutinin of subtype H2, a neuraminidase of subtype N3, or the combination thereof. A subtype H2 hemagglutinin of the present invention has hemagglutinin activity (HA). A subtype H2 hemagglutinin of the present invention can bind to mammalian cells, preferably, pig, human, or ferret cells. Preferably, a subtype H2 hemagglutinin is immunogenic. Hemagglutinin activity can be tested by routine methods know in the art. For instance, serial dilutions of a virus or isolated hemagglutinin can be placed in wells of a microtiter plate, and a dilute suspension of red blood cells (RBCs), typically chicken or turkey, are added to each well. After a suitable time to allow red blood cells to settle, control red blood cells settle to a compact button, and the presence of a hemagglutinin prevents the formation of the compact button. In some aspects, mammalian red blood cells are preferably used, for example horse RBC.

Examples of subtype H2 hemagglutinins include the amino acid sequence of SEQ ID NO:9 and SEQ ID NO:25. Other subtype H2 hemagglutinins include those having structural similarity with the amino acid sequence of SEQ ID NO:9 or SEQ ID NO:25. The similarity is referred to as structural similarity and is generally determined by aligning the residues of the two amino acid sequences (i.e., a candidate amino acid sequence and the amino acid sequence of SEQ ID NO:9 or SEQ ID NO:25) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in SEQ ID NO:9 or SEQ ID NO:25. A candidate amino acid sequence may be isolated from an influenza A virus, or may be produced using recombinant techniques, or chemically or enzymatically synthesized. Preferably, two amino acid sequences are compared using the BESTFIT algorithm in the GCG package (version 10.2, Madison Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identities." Preferably, a subtype H2 hemagglutinin polypeptide also includes polypeptides with an amino acid sequence having at least 80% amino acid identity, at least 85% amino acid identity, at least 86% amino acid identity, at least 87% amino acid identity, at least 88% amino acid identity, at least 89% amino acid identity, at least 90% amino acid identity, at least 91% amino acid identity, at least 92% amino acid identity, at least 93% amino acid identity, at least 94% amino acid identity, at least 95% amino acid identity, at least 96% amino acid identity, at least 97% amino acid identity, at least 98% amino acid identity, or at least 99% amino acid identity to SEQ ID NO:9 or SEQ ID NO:25. Preferably, a polypeptide having structural similarity to a subtype H2 hemagglutinin has hemagglutinin activity, binds to a mammalian cell, or the combination thereof. Preferably, a polypeptide having structural similarity to a subtype H2 hemagglutinin is immunogenic.

The present invention also includes isolated, preferably purified, subtype H2 hemagglutinins described herein, such as the subtype H2 hemagglutinins SEQ ID NO:9 and SEQ ID NO:25, and those polypeptides having structural similarity to SEQ ID NO:9 or SEQ ID NO:25 and preferably having hemagglutinin activity and ability to bind to a mammalian cell, such as a pig, ferret, mouse, or human cell. Preferably, the cell is a red blood cell.

An influenza A virus of the present invention may include a neuraminidase of subtype N3. A subtype N3 neuraminidase has neuraminidase activity (NA). Preferably, a subtype N3 neuraminidase is immunogenic. Neuraminidase activity can be tested by routine methods know in the art. See, for instance, Pedersen, 2008, Methods Mol Biol., 436:67-75.

Examples of subtype N3 neuraminidases include the amino acid sequence of SEQ ID NO:11 and SEQ ID NO:27. Other subtype N3 neuraminidases include those having structural similarity with the amino acid sequence of SEQ ID NO:11 or SEQ ID NO:27. The similarity is referred to as structural similarity and is generally determined by aligning the residues of the two amino acid sequences (i.e., a candidate amino acid sequence and the amino acid sequence of SEQ ID NO:11 or SEQ ID NO:27) as described above. Preferably, a subtype N3 neuraminidase polypeptide also includes polypeptides with an amino acid sequence having at least 80% amino acid identity, at least 85% amino acid identity, at least 86% amino acid identity, at least 87% amino acid identity, at least 88% amino acid identity, at least 89% amino acid identity, at least 90% amino acid identity, at least 91% amino acid identity, at least 92% amino acid identity, at least 93% amino acid identity, at least 94% amino acid identity, at least 95% amino acid identity, at least 96% amino acid identity, at least 97% amino acid identity, at least 98% amino acid identity, or at least 99% amino acid identity to SEQ ID NO:11 or SEQ ID NO:27. Preferably, a polypeptide having structural similarity to a subtype N3 neuraminidase has neuraminidase activity. Preferably, a polypeptide having structural similarity to a subtype N3 neuraminidase is immunogenic.

The present invention also includes isolated, preferably purified, subtype N3 neuraminidases described herein, such as subtype N3 neuraminidases SEQ ID NO:11 and SEQ ID NO:27, and those polypeptides having structural similarity to SEQ ID NO:11 or SEQ ID NO:27 and preferably having neuraminidase activity.

The present invention also includes fragments of the polypeptides described herein, e.g., subtype H2 hemagglutinins SEQ ID NO:9 and SEQ ID NO:25 as well as those polypeptides having structural similarity to SEQ ID NO:9 or SEQ ID NO:25, and subtype N3 neuraminidases SEQ ID NO:11 and SEQ ID NO:27, as well as those polypeptides having structural similarity to SEQ ID NO:11 or SEQ ID NO:27. A polypeptide fragment may include a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 amino acid residues. Preferred examples of fragments of an H2 hemagglutinin include epitopes that responsible for the hemagglutinin being a subtype H2 hemagglutinin, such as the HA1 domain. Preferred examples of fragments of an N3 neuraminidase include epitopes that responsible for the neuraminidase being a subtype N3 neuraminidase.

Optionally, a fragment may be biologically active. A biologically active fragment of a subtype H2 hemagglutinin has hemagglutinin activity and/or binds a mammalian cell, and a biologically active fragment of a subtype N3 neuraminidase has neuraminidase activity. Domains of influenza virus hemaggluinins and neuraminidases that have these activities are known to the skilled person.

An H2 hemagglutinin of the present invention having structural similarity to SEQ ID NOs: 9 or 25, and an N3 neuraminidase of the present invention having structural similarity to SEQ ID NOs: 11 or 27, may include one or more conservative substitutions of the sequence disclosed at SEQ ID NOs: 9, 11, 25, or 27. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) can generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, including amino acids not coded for in the standard genetic code and resulting from, for instance, post-translational modification of an amino acid, but also include artificial amino acids. Regions of hemagglutinins and neuraminidases that are conserved are known to the skilled person (Skehel and Wiley, 2000, Annu. Rev. Biochem., 69:531-569; Webster et al., 1992, Microbiol. Rev., 56:152-179; Blok and Air, 1982, Virol., 121:211-229; Barman et al., J. Virol., 78:5258-5269)

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

A polypeptide of the present invention or a fragment thereof may be expressed as a fusion polypeptide that includes a polypeptide of the present invention or a fragment thereof and a carrier polypeptide. The carrier polypeptide may be used to increase the immunogenicity of the fusion polypeptide to increase production of antibodies that specifically bind to a polypeptide of the invention. Such constructs may be useful for the production of vaccines (Song et al., 2008, PLoS ONE, 3(5):e2257). The invention is not limited by the types of carrier polypeptides that may be used to create fusion polypeptides. Examples of carrier polypeptides include, but are not limited to, keyhole limpet hemacyanin, bovine serum albumin, ovalbumin, mouse serum albumin, rabbit serum albumin, and the like.

A polypeptide of the present invention having structural similarity to SEQ ID NO:9, SEQ ID NO:11, SEQ ID NO:25, or SEQ ID NO:27 may have one or more conservative substitutions. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) can generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids.

The polypeptides of the present invention may be obtained from, for instance, a biological sample from a porcine animal infected with an influenza A virus. The influenza A virus may be one of the present invention. Preferably, the influenza A virus is SW_2124514 or SW_4296424. The polypeptide may be obtained from cultured cells or eggs, that have, for instance, been infected with an influenza A virus that encodes the polypeptide or contain a recombinant polynucleotide, preferably a polynucleotide of the invention, that encodes a polypeptide of the invention or a fragment thereof. The polypeptide may be obtained from a prokaryotic cell or a eukaryotic cell that contains an expression vector that includes a polynucleotide encoding a polypeptide of the invention or a fragment thereof. The polypeptides of the present invention may also be obtained by chemical synthesis.

An influenza A virus may include a polynucleotide encoding a subtype H2 hemagglutinin of the present invention. Examples of polynucleotides include the coding region SEQ ID NO:37 (nucleotides 59 to 1747 of SEQ ID NO:1), and the coding region SEQ ID NO:38 (nucleotides 59 to 1747 of SEQ ID NO:17). The polynucleotides disclosed herein are typically described as cDNA, and are a reverse complement of the actual RNA sequence present in the virus. SEQ ID NO:37 and SEQ ID NO:38 encode the subtype H2 hemagglutinins represented by SEQ ID NO:9 and SEQ ID NO:25, respectively. It should be understood that a polynucleotide encoding a subtype H2 hemagglutinin represented by SEQ ID NO:9 or SEQ ID NO:25 is not limited to the nucleotide sequence disclosed at SEQ ID NO:37 or SEQ ID NO:38, but also includes the class of polynucleotides encoding such polypeptides as a result of the degeneracy of the genetic code. For example, the naturally occurring nucleotide sequence SEQ ID NO:37 is but one member of the class of nucleotide sequences encoding a polypeptide having the amino acid sequence SEQ ID NO:9. Likewise, SEQ ID NO:38 is but one member of the class of nucleotide sequences encoding a polypeptide having the amino acid sequence SEQ ID NO:25. The class of nucleotide sequences encoding a selected polypeptide sequence is large but finite, and the nucleotide sequence of each member of the class can be readily determined by one skilled in the art by reference to the standard genetic code, wherein different nucleotide triplets (codons) are known to encode the same amino acid.

Other polynucleotides encoding a subtype H2 hemagglutinin include those having structural similarity with the nucleotide sequence of SEQ ID NO:37 or SEQ ID NO:38. The similarity is referred to as structural similarity and is determined by aligning the residues of the two polynucleotides (i.e., the nucleotide sequence of the candidate coding region and the nucleotide sequence of the coding region of SEQ ID NO:37 or SEQ ID NO:38) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate coding region is the coding region being compared to SEQ ID NO:37 or SEQ ID NO:38. A candidate nucleotide sequence may be isolated from an influenza A virus, or may be produced using recombinant techniques, or chemically or enzymatically synthesized. Preferably, two nucleotide sequences are compared using the BESTFIT algorithm in the GCG package (version 10.2, Madison Wis.), or the Blastn program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. In the comparison of two nucleotide sequences using the BLAST search algorithm, structural similarity is referred to as "identities." Preferably, a polynucleotide includes a nucleotide sequence having at least 80% nucleotide identity, at least 85% nucleotide identity, at least 86% nucleotide identity, at least 87% nucleotide identity, at least 88% nucleotide identity, at least 89% nucleotide identity, at least 90% nucleotide identity, at least 91% nucleotide identity, at least 92% nucleotide identity, at least 93% nucleotide identity, at least 94% nucleotide identity, at least 95% nucleotide identity, at least 96% nucleotide identity, at least 97% nucleotide identity, at least 98% nucleotide identity, or at least 99% nucleotide identity to SEQ ID NO:37 or SEQ ID NO:38. Preferably, a nucleotide sequence having structural similarity to SEQ ID NO:37 or SEQ ID NO:38 encodes a subtype H2 hemagglutinin with hemagglutinin activity and binds a mammalian cell.

The present invention also includes isolated, preferably purified, nucleotide sequences encoding a subtype H2 hemagglutinin, such as SEQ ID NO:37 and SEQ ID NO:38, and those nucleotide sequences having structural similarity to SEQ ID NO:37 or SEQ ID NO:38, as well as the complements and reverse complements thereof.

An influenza A virus may include a polynucleotide encoding a subtype N3 neuraminidase of the present invention. Examples of polynucleotides include the coding region SEQ ID NO:39 (nucleotides 5 to 1414 of SEQ ID NO:3), and the coding region SEQ ID NO:40 (nucleotides 3 to 1412 of SEQ ID NO:19). SEQ ID NO:39 and SEQ ID NO:40 encode the subtype N3 neuraminidases represented by SEQ ID NO:11 and SEQ ID NO:27, respectively. It should be understood that a polynucleotide encoding a subtype N3 neuraminidase represented by SEQ ID NO:11 and SEQ ID NO:27 is not limited to the nucleotide sequence disclosed at SEQ ID NO:39 and SEQ ID NO:40, but also includes the class of polynucleotides encoding such polypeptides as a result of the degeneracy of the genetic code. For example, the naturally occurring nucleotide sequence SEQ ID NO:39 is but one member of the class of nucleotide sequences encoding a polypeptide having the amino acid sequence SEQ ID NO:11. Likewise, SEQ ID NO:40 is but one member of the class of nucleotide sequences encoding a polypeptide having the amino acid sequence SEQ ID NO:27. The class of nucleotide sequences encoding a selected polypeptide sequence is large but finite, and the nucleotide sequence of each member of the class can be readily determined by one skilled in the art by reference to the standard genetic code, wherein different nucleotide triplets (codons) are known to encode the same amino acid.

Other polynucleotides encoding a subtype N3 neuraminidase include those having structural similarity with the nucleotide sequence of SEQ ID NO:39 or SEQ ID NO:40. The similarity is referred to as structural similarity and is determined by aligning the residues of the two polynucleotides (i.e., the nucleotide sequence of the candidate coding region and the nucleotide sequence of the coding region of SEQ ID NO:39 or SEQ ID NO:40) as described above. Preferably, a polynucleotide includes a nucleotide sequence having having at least 80% nucleotide identity, at least 85% nucleotide identity, at least 86% nucleotide identity, at least 87% nucleotide identity, at least 88% nucleotide identity, at least 89% nucleotide identity, at least 90% nucleotide identity, at least 91% nucleotide identity, at least 92% nucleotide identity, at least 93% nucleotide identity, at least 94% nucleotide identity, at least 95% nucleotide identity, at least 96% nucleotide identity, at least 97% nucleotide identity, at least 98% nucleotide identity, or at least 99% nucleotide identity to SEQ ID NO:39 or SEQ ID NO:40. Preferably, a nucleotide sequence having structural similarity to SEQ ID NO:39 or SEQ ID NO:40 encodes a subtype N3 neuraminidase with neuraminidase activity.

The present invention also includes isolated, preferably purified, nucleotide sequences encoding a subtype N3 neuraminidases, such as SEQ ID NO:39 and SEQ ID NO:40, and those nucleotide sequences having structural similarity to SEQ ID NO:39 or SEQ ID NO:40, as well as the complements and reverse complements thereof.

A polynucleotide of the present invention can be inserted in a vector. A vector is a replicating polynucleotide to which another polynucleotide may be attached so as to bring about the replication of the attached polynucleotide. The term vector includes, but is not limited to, plasmid vectors, viral vectors, cosmid vectors, or artificial chromosome vector. When a polynucleotide of the present invention is in a vector the polynucleotide can be DNA or RNA. When present in a vector, a polynucleotide of the invention can be referred to as a recombinant polynucleotide. Construction of vectors containing a polynucleotide of the invention employs standard ligation techniques known in the art. See, e.g., Sambrook et al, Molecular Cloning: A Laboratory Manual., Cold Spring Harbor Laboratory Press (1989).

A vector can provide for further cloning (amplification of the polynucleotide), i.e., a cloning vector, or for expression of the polypeptide encoded by the coding region, i.e., an expression vector. Suitable expression vectors include those that can be used to produce amounts of polypeptide that can be used in a subunit vaccine and administration to an animal. Examples of such expression vectors include, but are not limited to, plamid, baculovirus, or vaccinia virus, etc., expression systems. Suitable expression vectors include those that can be used as expression vectors that can be administered to an animal to result in immunization. Such vectors, often referred to in the art as vectored vaccines, may be a microbe or virus modified to express a polypeptide of the present invention or a fragment thereof. Examples of such expression vectors include, but are not limited to, virus vectors such as Newcastle Disease virus (Park et al., 2006, Proc Natl Acad Sci USA, 103:8203-8208), Canarypox virus (Carithers, 1995, Vaccine, 13:539-549; Paoletti, 1996, Proc Natl Acad Sci USA, 93:11349-11353), attenuated influenza A virus (Palese et al., WO 2006/083286), vaccinia virus (Paoletti, 1996, Proc Natl Acad Sci USA, 93(21):11349-11353), adenovirus, herpes virus, sindbis virus, and fowlpox (Paoletti, 1996, Proc Natl Acad Sci USA, 93(21):11349-11353), and microbe vectors such as *Salmonella* spp. Vectors may include a coding region encoding a polypeptide of the present invention or a fragment thereof.

Selection of a vector depends upon a variety of desired characteristics in the resulting construct, such as a selection marker, vector replication rate, and the like. Suitable host cells for cloning or expressing the vectors herein are prokaryote or eukaryotic cells.

An expression vector optionally includes regulatory sequences operably linked to the coding region. The invention is not limited by the use of any particular promoter, and a wide variety of promoters are known. Promoters act as regulatory signals that bind RNA polymerase in a cell to initiate transcription of a downstream (3' direction) coding region. The promoter used may be a constitutive or an inducible promoter. It may be, but need not be, heterologous with respect to the host cell. Examples of useful promoters include, but are not limited to, SV40 T-antigen promoter, cytomegalovirus enhancer, chicken M-actin promoter, and pCATG promoter.

An expression vector may optionally include a ribosome binding site and a start site (e.g., the codon ATG) to initiate translation of the transcribed message to produce the polypeptide. It may also include a termination sequence to end translation. A termination sequence is typically a codon for which there exists no corresponding aminoacetyl-tRNA, thus ending polypeptide synthesis. The polynucleotide used to transform the host cell may optionally further include a transcription termination sequence.

The vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence are sequences that confer resistance to kanamycin, ampicillin, chloramphenicol, tetracycline, and neomycin.

Polypeptides and fragments thereof useful in the present invention may be produced using recombinant DNA techniques, such as an expression vector present in a cell. Such methods are routine and known in the art. The polypeptides and fragments thereof may also be synthesized in vitro, e.g., by solid phase peptide synthetic methods. The solid phase peptide synthetic methods are routine and known in the art. A polypeptide produced using recombinant techniques or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity.

The present invention includes antibodies that specifically bind a virus of the present invention. An antibody that specifically binds an influenza A subtype H2N3 virus of the present invention, preferably, SW_2124514 or SW_4296424, is an antibody that does not specifically bind an influenza A virus having the designation A/Mallard/Alberta/79/2003 (Obenauer et al., 2006, Science, 311:1576-1580).

The present invention also includes antibodies that specifically bind a polypeptide of the present invention. An antibody that specifically binds a subtype H2 polypeptide of the present invention, preferably, the subtype H2 hemagglutinin SEQ ID NO:9, SEQ ID NO:25, or a fragment thereof, does not bind to the subtype H2 hemagglutinin having the amino acid sequence described at Genbank Accession Number ABB18080 (SEQ ID NO:42). An antibody that specifically binds a subtype N3 neuraminidase of the present invention, preferably, the subtype N3 neuraminidase SEQ ID NO:11, SEQ ID NO:27, or a fragment thereof, does not bind to the subtype N3 neuraminidase having the amino acid sequence described at Genbank Accession Number ABB80526 (SEQ ID NO:44).

Antibody may be produced using a virus of the present invention, a polypeptide of the present invention, or a fragment thereof. Preferably, the antibody is monoclonal. Laboratory methods for producing, characterizing, and optionally isolating polyclonal and monoclonal antibodies are known in the art (see, for instance, Harlow E. et al. *Antibodies. A laboratory manual* Cold Spring Harbor Laboratory Press, Cold Spring Harbor (1988). For instance, a virus of the present invention may be administered to an animal, preferably a mammal, in an amount effective to cause the production of antibody specific for the administered virus. Polypeptides of the present invention may also be administered to an animal, preferably a mammal, to produce antibodies. Optionally, a virus or a polypeptide may be mixed with an adjuvant, for instance Freund's incomplete adjuvant, to stimulate the production of antibodies upon administration. Whether an antibody of the present invention specifically binds to a virus and/or a polypeptide of the present invention can be determined using methods known in the art. For instance, specificity may be determined by testing antibody binding to SEQ ID NO:9 and the amino acid sequence SEQ ID NO:42. Other examples include testing the kinetics of antibody binding to different polypeptides, and testing competition in binding using as competitors known polypeptides containing or not containing an epitope against which the antibody is directed.

An antibody produced using a virus or a polypeptide may be a neutralizing antibody. A neutralizing antibody is one that prevents a virus of the present invention from replicating in cell culture. Without intending to be limited by mechanism, the inability to replicate can occur by, for instance, aggregation of virus particles, inhibition of attachment of virus to cell receptors on the target cell, inhibition of virus internalization, inhibition of the entry of the viral genome and associated proteins into the cell, or inhibition of a postentry event (Dimmock, 1993, Curr. Top. Microbiol. Immunol. 183:1-149). Methods for testing antibody to determine if it is neutralizing are routine and known in the art.

The present invention also provides compositions including one or more viruses, polypeptides, polynucleotides, or antibodies of the present invention, or combinations thereof. Such compositions may include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration and not deleterious to a recipient thereof. A composition of the present invention may be referred to as a vaccine. The term "vaccine" as used herein refers to a composition that, upon administration to an animal, will increase the likelihood the recipient is protected against a virus of the present invention. For instance, when the composition includes or encodes an immunogenic polypeptide, administration to the animal typically produces an immunological response to the polypeptide and results in immunity. Without intending to be limited by theory, preferably the use of a vaccine that includes a polypeptide or encodes a polypeptide elicits neutralizing antibodies in the recipient.

A composition may include a whole virus, such as an inactivated virus or an attenuated virus. A composition may include virus that has been disrupted. Such a composition, often referred to as a split vaccine, may be prepared by fragmentation of whole virus, either wild-type (i.e., infectious), inactivated, or attenuated, with solubilizing concentrations of organic solvents or detergents and subsequent removal of the solubilizing agent and some or most of the viral lipid material. Split vaccines generally contain contaminating matrix protein and nucleoprotein and sometimes lipid, as well as the membrane envelope proteins. Split vaccines typically contain most or all of the virus structural proteins, although not necessarily in the same proportions as they occur in the whole virus. Methods for disrupting influenza A virus to prepare split vaccines are known and used routinely, and typically include a number of different filtration and/or other separation steps such as ultracentrifugation, ultrafiltration, zonal centrifugation, and chromatography (e.g ion exchange) steps in a variety of combinations, and optionally an inactivation step, which may be carried out before or after splitting. The splitting process may be carried our as a batch, continuous, or semi-continuous process.

A composition may include one or more polypeptides of the present invention. Such a composition is often referred to as a subunit vaccine. The polypeptides present in the composition may be obtained by isolation, preferably purification, from virus particles, such as disrupting a virus followed by isolation of the polypeptide(s). The polypeptides present in the composition may also be obtained by using expression systems as described herein followed by isolation, preferably purification, of the polypeptide(s). Preferably, a composition including a polypeptide includes a hemagglutinin or a neuraminidase, more preferably, both a hemagglutinin and a neuraminidase.

A composition may include a polynucleotide of the present invention. The polynucleotide can include DNA, RNA, or a combination thereof. The polynucleotide may be supplied as part of a vector or as a "naked" polynucleotide. General methods for construction, production, and administration of polynucleotide vaccines are known in the art, e.g. F. Vogel et al., 1995, Clin. Microbiol. Rev. 8:406-410; Freeman et al., WO 93/02556; Felgner et al., U.S. Pat. No. 5,580,859, Pardoll et al., 1995, Immunity 3:165; Stevenson et al., 1995, Immunol. Rev. 145:211; Molling, 1997, J. Mol. Med. 75:242 (1997); Donnelly et al., 1995 Ann. NY. Acad. Sci. 772:40; Yang et al., 1996, Mol. Med. Today 2:476; and Abdallah et al., 1995, Biol. Cell 85:1. A nucleic acid molecule may be generated by methods standard in the art, such as by recombinant techniques, or by enzymatic or chemical synthesis.

A composition may be univalent or multivalent, such as bivalent or trivalent. For instance, a composition may include one or more viruses, polypeptides, polynucleotides, or antibodies of the present invention, or combinations thereof, for protecting against more than one type of influenza virus. For instance, a composition may include or express antigens to more than one type of influenza virus. Likewise, a composition including antibodies may include antibodies to more than one type of influenza virus. For example, an additional influenza virus may be an influenza A virus that is not H2N3, or an influenza B virus. A composition may include compounds for protecting against other pathogens, including viral pathogens and microbial pathogens. For instance, a composition may include *Mycoplasma hyopneumoniae* bacterin, *Leptospira* sp. bacterins, Eastern Encephalomyelitis virus vaccines, Western Encephalomyelitis virus vaccines, or Tetanus Toxoid.

Compositions of the present invention may further include at least one adjuvant. An "adjuvant" refers to an agent that may act in a nonspecific manner to enhance an immune response to a particular antigen, thus potentially reducing the quantity of antigen necessary in any given immunizing composition, and/or the frequency of administration necessary in order to generate an adequate immune response to the antigen of interest. Preferably, an adjuvant will aid in stimulating a TH1 type response through antigen presentation by dendritic cells to T-cells. Adjuvants may include, for example, IL-1, IL-2, emulsifiers, muramyl dipeptides, dimethyldiocradecylammonium bromide, avridine, aluminum hydroxide, oils, saponins (Lacaille-Dubois and Wagner, 1996, Phytomedicine, 2:363-386), alpha-tocopherol, polysaccharides, emulsified paraffins, ISA-70, RIBI, enterobacterial lipopolysaccharide (LPS), synthetic polymers, and other substances known in the art.

Examples of saponins include, but are not limited to, Quil A (derived from the bark of the South American tree Quillaja *Saponaria* Molina), and fractions thereof (Kensil and Marciani, U.S. Pat. No. 5,057,540; Kensil, 1996, Crit. Rev. Ther. Drug Carrier Syst., 12:1-55; and Kensil et al., EP 0 362 279 B1), such as QS21 and QS17, and saponins derived from other plant species such as *Gypsophila* and *Saponaria* (Bomford et al., 1992, Vaccine, 10:572-577). Examples of LPS include, but are not limited to, the non-toxic derivative of LPS, monophosphoryl lipid A (MPL; Ribi et al., 1986, Immunology and Immunopharmacology of bacterial endotoxins, Plenum Publ. Corp., NY, p 407-419), 3-O-deacylated monophosphoryl lipid A (3D-MPL; GB 2122204B), and diphosphoryl lipid A (GB 2220211; Myers and Truchot, U.S. Pat. No. 4,912,094). Other purified and synthetic lipopolysaccharides useful as adjuvants have been described (Hilgers et al., 1986, Int. Arch. Allergy. Immunol., 79:392-396; Hilgers et al., 1987, Immunology, 60:141-146; and Hilgers and Platenburg, EP 0 549 074 B1).

Compositions of the present invention may further include at least one surfactant, preferably, a non-ionic surfactant. Suitable non-ionic surfactants include, but are not limited to, octyl- or nonylphenoxy polyoxyethanols, polyoxyethylene sorbitan esters, and polyoxyethylene ethers. Octylphenoxy polyoxyethanols and polyoxyethylene sorbitan esters are described in "Surfactant systems" Eds: Attwood and Florence (1983, Chapman and Hall). Octylphenoxy polyoxyethanols (the octoxynols), including t-octylphenoxypolyethoxyethanol (Triton X-100) are also described in Merck Index Entry 6601 (Page 971, $10^{th}$ Edition, Merck & Co. Inc., Whitehouse Station, N.J.). The polyoxyethylene sorbitan esters, including polyoxyethylene sorbitan monooleate (Tween 80) are described in Merck Index Entry 7455 (Page 1095, $10^{th}$ Edition, Merck & Co. Inc., Whitehouse Station, N.J.). Further polyoxyethylene ethers include, for instance, polyoxyethylene-8-stearyl ether, polyoxyethylene-4-lauryl ether, polyoxyethylene-35-lauryl ether, and polyoxyethylene-23-lauryl ether. Particularly preferred non-ionic surfactants include Triton X-45™, Triton X-102™, Triton X-114™, Triton X-165™, Triton X-205™, Triton X-305™, Triton N-57™, Triton N-101™, Triton N-128™, polyoxyethylene-9-lauryl ether (laureth 9) and polyoxyethylene-9-stearyl ether (steareth 9).

A composition of the invention may include a pharmaceutically acceptable carrier may include a biological response modifier, such as, for example, IL-2, IL-4 and/or IL-6, TNF, IFN-alpha, IFN-gamma, and other cytokines that effect immune cells.

Immunogenic carriers may be used to enhance the immunogenicity of polypeptides present in a composition of the present invention. Such carriers include but are not limited to other polypeptides, polysaccharides, liposomes, and bacterial cells and membranes. Polypeptide carriers may be joined to the attenuated or inactivated virus of the present invention, and/or a polypeptide of the present invention to form fusion polypeptides by recombinant or synthetic means or by chemical coupling. Useful carriers and means of coupling such carriers to polypeptide antigens are known in the art.

A composition may be prepared by methods known in the art of pharmacy. In general, a composition can be formulated to be compatible with its intended route of administration. More specifically, the compositions of the present invention may be administered to any tissue of an animal, including, but not limited to, muscle (such as skeletal muscle or cardiac muscle), skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue, rectal tissue, nervous system tissue, eye tissue, glandular tissue, tongue tissue, and connective tissue, e.g., cartilage.

A composition of the present invention may be administered to any internal cavity of an animal, including, but not limited to, lungs, mouth, nasal cavity, stomach, peritoneal cavity, intestine, a heart chamber, veins, arteries, capillaries, lymphatic cavities, uterine cavity, joint cavities, spinal canal in spinal cord, ocular cavities, the lumen of a duct of a salivary gland or a liver. In some aspects, the compositions may be administered into embryonated avian eggs (Mendu et al., U.S.

Pat. No. 7,249,569), by injection into birds, or by nasal delivery to birds (Gorans and Erickson, US Patent Application 20050101937).

Compositions of the present invention may be administered by intramuscular (i.m.), subcutaneous (s.c.), or intrapulmonary routes. Other suitable routes of administration include, but are not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), inraatrial (i.e., into the heart atrium) and sub arachnoid (i.e., into the sub arachnoid spaces of the brain) administration.

Any route of administration may be used so long as it results in the delivery of an amount sufficient to generate an immune response (when a polypeptide or polynucleotide is administered) or a protective response (when an antibody is administered) in an animal in need of such response. Intradermal delivery is preferred, and may be accomplished using any suitable device. Examples of suitable devices include, but are not limited to, short needle devices, devices that limit needle penetration length, jet injection devices, and ballistic delivery devices.

A composition of the present invention may be administered in a variety of different dosage forms. An aqueous medium containing the composition may be desiccated and combined with pharmaceutically acceptable inert excipients and buffering agents such as lactose, starch, calcium carbonate, sodium citrate formed into tablets, capsules, and the like. These combinations may also be formed into a powder or suspended in an aqueous solution such that these powders and/or solutions may be added to food or to drinking water. These compositions may be suitably sweetened or flavored by various known agents to promote the uptake of the composition orally by an animal. Administration of a composition of the present invention may further include administration of other antiviral agents. Many antiviral agents are known in the art and are used routinely.

For purposes of parenteral administration, the composition may be combined with pharmaceutically acceptable carrier(s) well known in the art such as saline solution, water, propylene glycol, etc. In this form, the composition may be parenterally, intranasally, or orally applied by methods known in the art. The composition may also be administered intravenously by syringe. In this form, the vaccine may be combined with pharmaceutically acceptable aqueous carrier(s) such as a saline solution. The parenteral and intravenous formulations of the composition may also include emulsifying and/or suspending agents as well, together with pharmaceutically acceptable diluent to control the delivery and the dose amount of the composition.

Solutions or suspensions may include the following components: a sterile diluent such as water for administration, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates; electrolytes, such as sodium ion, chloride ion, potassium ion, calcium ion, and magnesium ion, and agents for the adjustment of tonicity such as sodium chloride or dextrose. pH may be adjusted with acids or bases, such as hydrochloric acid or sodium hydroxide. A composition may be enclosed in ampoules, disposable syringes or multiple dose vials made of glass or plastic.

Compositions may include sterile aqueous solutions (where water soluble) or dispersions and sterile powders for the extemporaneous preparation of sterile solutions or dispersions. For intravenous administration, suitable carriers include physiological saline, bacteriostatic water, or phosphate buffered saline (PBS). A composition is typically sterile and, when suitable for injectable use, should be fluid to the extent that easy syringability exists. It should be stable under the conditions of manufacture and storage and preserved against the contaminating action of microorganisms such as bacteria and fungi. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions may be brought about by including in the composition an agent which delays absorption, for example, aluminum monostearate and gelatin.

The compositions of the present invention may be prepared with carriers that will protect the one or more viruses, polypeptides, polynucleotides, or antibodies against rapid elimination from the body, such as a controlled release formulation, including implants. Biodegradable, biocompatible polymers may be used, such as ethylene vinyl acetate, polyanhydrides, polyglycolic acid, collagen, polyorthoesters, and polylactic acid. Such formulations may be prepared using standard techniques. The materials may also be obtained commercially. Liposomal suspensions may also be used as pharmaceutically acceptable carriers. These may be prepared according to methods known to those skilled in the art.

Determining an effective amount of one or more compositions of the present invention depends upon a number of factors including, for example, the virus or the polypeptide being administered or expressed, the age and weight of the animal, the severity of the disease, and the route of administration. Based on the above factors, determining the precise amount, number of doses, and timing of doses are within the ordinary skill in the art and will be readily determined by the attending physician or veterinarian.

The present invention is also directed to methods of using the compositions described herein. The methods include, for instance, methods of treatment and methods of diagnosis. Treatment may be prophylactic or, alternatively, may be initiated after the exposure of an animal to influenza A virus, preferably, an influenza A virus of the present invention. Prophylactic treatment refers to the use of a composition of the present invention to generate immunity in an animal which has not yet been exposed to influenza A virus, preferably an influenza A virus of the present invention, thereby preventing or reducing disease signs if the animal is later exposed to such an influenza A virus. Treatment that is prophylactic, for instance, initiated before an animal manifests signs of influenza infection, is referred to herein as treatment of an animal that is "at risk" of developing influenza. Treatment initiated after the exposure of an animal to an influenza A virus may result in decreasing the severity of the signs, or completely removing the signs. In this aspect of the invention, an "effective amount" is an amount effective to prevent the manifestation of signs of influenza, decrease the severity of the signs of influenza, and/or complete remove the signs. The methods of the present invention therefore may be referred to as therapeutic vaccination or preventative or prophylactic vaccination. It is not required that any composition of the present invention provide total immunity to influenza or totally cure or eliminate all influenza disease signs.

The methods may include administering a composition of the present invention to an animal. Thus, the administered composition may include one or more viruses, polypeptides, polynucleotides, or antibodies of the present invention, or combinations thereof. The animal may be any animal susceptible to infection by a virus of the present invention, including, but not limited to, a vertebrate, more preferably a mammal (such as a pig, a mouse, a ferret, or a human), or an avian (such as a bird). Examples of birds include, but are not limited to, feral birds such as ducks and geese, and domesticated birds such as turkeys, chickens, ducks, and geese. A composition of the present invention may be delivered to an animal by methods described herein and known in the art, thereby achieving an effective therapeutic vaccination or preventative vaccination.

The present invention provides methods for detecting a virus of the present invention. These methods are useful in, for instance, detecting influenza A virus of the present invention in an animal, detecting influenza A virus of the present invention in a cell culture, or diagnosing a disease caused by influenza A virus of the present invention (including during an infection or after an infection). Preferably, the virus detected is influenza A subtype H2N3. In some aspects of the invention, detecting influenza A virus includes detecting such a virus in an animal. These methods may include providing a biological sample from an animal. In this aspect the animal is one that is suspected of harboring the virus (presently infected), or may be a member of a group that is being screened for the presence of influenza A. Antibody of the present invention may be added to the biological sample and incubated under conditions to form a complex with influenza A virus, such as a virus expressing an H2 hemagglutinin of the present invention, or a virus expressing an N3 neuraminidase of the present invention. Preferably, the antibody does not specifically bind an influenza A having the designation A/Mallard/Alberta/79/2003, and/or does not specifically bind to the subtype H2 hemagglutinin having the amino acid sequence described at Genbank Accession Number ABB18080 (SEQ ID NO:42). The complex is then detected, and the presence of the complex indicates the presence of influenza A virus of the present invention in the biological sample. The detection of antibodies is known in the art and may include, for instance, immunofluorescence and peroxidase. Typical formats in which antibodies of the present invention may be used include, for instance, enzyme linked immunosorbent assay (ELISA); radioimmunoassay (RIA), immunofluorescent assay (IFA), and western immunoassay. Other assays for use when an animal is one that is suspected of harboring the virus (presently infected) include mass spectroscopy (Downard and Morrissey, 2007, Analyst, 132:611-614; Morrissey et al., 2007, J. Viriol. Methods, 145:106-114).

The present invention also includes methods for determining whether an animal has been exposed to influenza A virus of the present invention. Such an animal may be presently infected with such a virus or the virus may no longer be present in the animal. The methods typically include testing a biological sample obtained from an animal for the presence of antibody that specifically binds a virus of the present invention. Preferably, the biological sample is derived from the circulatory system and may be, for instance, blood (including serum) or lymph. For example, the hemagglutination inhibition assay generally includes mixing red blood cells (RBCs, typically chicken or turkey RBCs, and in some aspects, mammalian RBCs) with an influenza A virus of the present invention, and serum in a tube or a microtiter plate. Preferably, the influenza A virus used expresses a hemagglutinin of the present invention, more preferably, is SW_2124514 or SW_4296424. Typically, serum is serially diluted and several mixtures are prepared. This is incubated statically for approximately 1 hour, and the shape of the settled RBCs evaluated. The presence of a compact button (non-agglutinated) of RBCs at the bottom of the test tube or well indicates antibody was added to the test tube. If all of the dilutions tested for an animal are negative, this generally indicates the animal was exposed to influenza A virus. The presence of agglutinated RBCs at the bottom of the test tube or well indicates no antibody to the virus was added to the test tube, and this usually indicates the animal was not exposed to influenza A virus.

Other methods for detecting a virus of the present invention include the amplification of a polynucleotide, preferably by the polymerase chain reaction (PCR). The polynucleotide may be one that is, for instance, present in a biological sample from an animal that is suspected of harboring the virus, or a member of a group that is being screened for the presence of the virus. The polynucleotide may be obtained from a virus of the present invention, preferably, SW_2124514 or SW_4296424. When the polynucleotide is obtained from a virus particle, the polynucleotide is converted from an RNA polynucleotide to a DNA polynucleotide by reverse transcription.

The method may include contacting a viral polynucleotide that is suspected of being influenza A virus of the present invention with a primer pair and incubating under conditions to form a detectable amplified polynucleotide. As used herein, a "primer pair" refers to two single stranded polynucleotides that can be used together to amplify a region of a polynucleotide, preferably by a PCR. Many variations of PCR exist, including, for instance, real time PCR and mass tag PCR (Briese et al., 2005, Emerging Inf. Dis., 11: 310-313), and are useful herein. The polynucleotide that results from amplifying a region of a polynucleotide is referred to as an "amplification product" or an "amplified polynucleotide." The phrase "under conditions suitable to form a detectable amplification product" refers to the reaction conditions that result in an amplification product. For instance, in the case of a PCR, the conditions suitable to form a detectable amplification product include the appropriate temperatures, ions, and enzyme.

Suitable polynucleotides that can be amplified include polynucleotides encoding a hemagglutinin of the present invention and a neuraminidase of the present invention. Primers that amplify a portion of a polynucleotide of the present invention can be designed using readily available computer programs, such as DNAStar Lasergene (Madison, Wis.). Factors that can be considered in designing primers include, but are not limited to, melting temperatures, primer length, size of the amplification product, and specificity. Primer length is generally between about 15 and about 30 nucleotides. The conditions for amplifying a polynucleotide by PCR vary depending on the nucleotide sequence of primers used, and methods for determining such conditions are routine in the art. An example of a primer pair that can be used in this method includes 5'-CAG GCA GTT TCA ATG ATT ATG (SEQ ID NO:33) and 5'-CCA TCA ATT GCC TTT TGA GT (SEQ ID NO:34), which results in an amplified polynucleotide of 842 nucleotides. Another primer pair is 5'-AGC AAA AGC AGG TGC GAG ATG-3' (SEQ ID NO:35) and 5'-AGT AGA AAC AAG GTG CTT TTT TCT-3' (SEQ ID NO:36), which results in an amplified polynucleotide of 1,413 nucleotides. It is understood that the nucleotide sequences of the segments described herein permit the skilled person to identify other primers that can be used in PCR, including real time PCR. Such primers may overlap with the primers disclosed herein.

The present invention provides kits. A kit may include a polypeptide described herein (when detecting antibody to a virus) an antibody described herein (for detecting the presence of a virus) or a primer pair as described herein (when amplifying a polynucleotide) in a suitable packaging material in an amount sufficient for at least one assay. Optionally, other reagents such as buffers and solutions, external positive or negative controls, and the like, needed to practice the invention are also included. Instructions for use of the packaged polypeptide, antibody, or primer pair may also be included.

The kits typically include packaging material, which refers to one or more physical structures used to house the contents of the kit. The packaging material can be constructed by well-known methods, preferably to provide a sterile, contaminant-free environment. The packaging material may have a marking that indicates the contents of the kit. In addition, the kit contains instructions indicating how the materials within the kit are employed. As used herein, the term "package" refers to a solid matrix or material such as glass, plastic, paper, foil, and the like.

"Instructions" typically include a tangible expression describing the various methods of the present invention, including sample preparation conditions, amplification conditions, and the like.

The present invention is illustrated by the following examples. It is to be understood that the particular examples, materials, amounts, and procedures are to be interpreted broadly in accordance with the scope and spirit of the invention as set forth herein.

Example 1

This example describes the isolation and characterization of H2N3 influenza A viruses from pigs with respiratory disease from two farms in the United States, a subtype not previously reported in swine. These H2N3 reassortant viruses contain genes derived from avian and swine influenza viruses. The pathogenicity and transmissibility of the H2N3 isolates in different mammalian hosts was also investigated. The H2N3 virus was able to replicate in pigs, mice, and ferrets and was transmitted among pigs and ferrets. Serologic evidence suggests that the virus continued to circulate in the affected swine production systems.

Materials and Methods

Analysis of Clinical Samples. An outbreak of respiratory disease occurred in pigs at a commercial grower-finisher swine farm. At necropsy, the attending veterinarian observed gross lesions of pneumonia and submitted formalin-fixed and unfixed sections of lung tissue to the Minnesota Veterinary Diagnostic Laboratory (MVDL). At the MVDL, the formalin-fixed tissue was routinely processed for histopathology. Bronchial swab samples from the unfixed lung tissue were suspended in 2 ml of PBS and tested for Mycoplasma hyopneumoniae by PCR (Calsamiglia et al., 1999, *J Vet Diagn Invest* 11:246-251). Unfixed sections (approximately 5 g) of lung were cultured aerobically for bacteria by inoculation on MacConkey, colistin-nalidixic acid, brilliant green, and blood agar plates with and without nicotinamide adenosine dinucleotide (NAD) factor (Staphylococcus epidermidis nurse colonies). In parallel, unfixed sections of lung (approximately 10 g) were homogenized in Eagle's minimal essential medium (MEM) containing 4% BSA, 15 µg/100 ml trypsin, and an antibiotic mixture of neomycin, gentamicin, penicillin, streptomycin, and amphotericine B and were cultivated on Madin-Darby canine kidney (MDCK) cells. RNA and DNA were also isolated from the homogenate for diagnostic tests for influenza virus nucleoprotein (RT-PCR), PRRSV ORF 6 (RT-PCR), and PCV2 ORF 2 (PCR).

For virus isolation, 10% lung homogenates were centrifuged for 10 min at 640×g. The supernatant was passed through 0.45-µm filters to remove any bacterial contamination and was inoculated on monolayers of MDCK cells in 24-well plates. The MDCK cells were maintained in Eagle's MEM containing 1 µg/ml TCPK-trypsin and 0.3% bovine albumin. The plates were incubated at 37° C. in a CO2 incubator and were observed daily. After cytopathic effects were observed, infected cells were lysed by freezing and thawing, and virus was serotyped by hemagglutination inhibition assays with turkey erythrocytes. Five months after the first outbreak, another outbreak of respiratory disease occurred in 5- to 6-week-old pigs at a different multisourced commercial swine nursery. Again, gross lesions were consistent with pneumonia, and lung tissues were submitted to the MVDL for testing as described above.

Hemagglutination Inhibition (HI) Assays. HI assays were performed for serologic subtyping of H2N3 viruses to determine seroconversion and to test convalescent serum samples collected from the various swine herds associated with the outbreak. Sera were heat-inactivated at 56° C., treated with a 20% suspension of kaolin (Sigma-Aldrich) to eliminate non-specific inhibitors, and adsorbed with 0.5% turkey red blood cells. The sera were tested for antibodies against H2N3 swine influenza viruses and reference strains of swine influenza (A/Swine/IA/1973 H1N1, A/Swine/TX/98 H3N2, and A/Sw/NC/2001 variant H1N1) virus by HI assay (Palmer et al., 1975, Advanced Laboratory Techniques for Influenza Diagnosis (United States Department of Health, Education, and Welfare, Washington, D.C.) pp. 51-52). The ferret sera were tested to determine seroconversion for H2N3 virus.

DNA Sequencing, Phylogenetic Analysis, and Subtype Determination. Viral RNA was prepared from 200 µl of virus suspension with the RNeasy Mini Kit (Qiagen) as directed by the manufacturer. Two-step RT-PCR was conducted by using universal primers as reported (Hoffmann et al., 2001, *Arch Virol* 146:2275-2289 and Ma et al., 2006, *J Virol* 80:5092-5096). Each gene segment was amplified under standard conditions. PCR products were purified by using a QIAamp Gel extraction kit (Qiagen) and sequenced by using an ABI 3730 DNA Analyzer (Applied Biosystems). Multiple sequence alignments were made by using CLUSTALW (Thompson et al., 1994, Nucleic Acids Res 22:4673-4680), and phylogenetic trees were generated by using the neighbor joining algorithm in the PHYLIP version 3.57C software package (Felsenstein JPHYLIP, 1993, (Department of Genetics, University of Washington, Seattle) Version 3.5c). A Megablast search of the Influenza Sequence Database was performed. The viral subtype determined by sequencing was compared with those from GenBank. The isolate was plaque-purified, retested, and again subtyped by RT-PCR and sequencing (plaques were uniform in appearance, and two plaques from each isolate were chosen for amplification and sequencing).

Experiments in Pigs. Pigs were obtained from a healthy herd that was free of swine influenza virus and PRRSV. All animal experiments were in compliance with the Institutional Animal Care and Use Committee of the National Animal Disease Center (NADC). The inoculation protocol has been described in Richt et al. (2003, *J Clin Microbiol* 41:3198-3205). Briefly, 20 4-week-old cross-bred pigs were inoculated intratracheally with $2\times10^6$ tissue culture infective dose ($TCID_{50}$) per pig of Sw/4296424 virus prepared in MDCK cells. Four-week-old contact pigs were commingled with inoculated pigs on day 3 p.i. to study transmission efficiency. Twelve control pigs were inoculated with noninfectious cell culture supernatant. Five of 20 inoculated pigs and 3 of 12 control pigs were euthanized on days 3, 5, and 7 p.i., respectively. The remaining five pigs from the inoculated group and three control pigs were euthanized on day 27 p.i. and were analyzed for seroconversion. Nasal swabs were taken on days 0, 3, 5, and 7 p.i., placed in 2 ml of MEM, and stored at −80° C. Blood was collected from all inoculated, contact, and control pigs on days 0, 3, 5, 7, and 14 p.i. Blood was also collected from contact pigs on day 24 after contact and from the remaining five inoculated and control pigs on day 27 p.i. and was analyzed for seroconversion. Each lung was lavaged with 50 ml of MEM to obtain BALF.

Viral load in BALF was determined in a 96-well plate as described in Richt et al. (2003, *J Clin Microbiol* 41:3198-3205). Briefly, 10-fold serial dilutions of each sample were made in serum-free MEM supplemented with TPCK-trypsin and antibiotics. Each dilution (100 µl) was plated on PBS-washed confluent MDCK cells in 96-well plates. Plates were evaluated for cytopathic effects after 24 to 48 hours. At 48 hours, plates were fixed with 4% phosphate-buffered formaldehyde and immunocytochemically stained with a monoclonal antibody to influenza A nucleoprotein (Kitikoon et al., 2006, *Vet Immunol Immunopathol* 112:117-128). The $TCID_{50}$/ml was calculated for each sample by the method of Reed and Muench (Reed and Muench, 1938, *Am J Hyg* 27:493-497).

Virus was isolated from nasal swab samples stored at −80° C. by thawing and vortexing each sample for 15 seconds, centrifuging it for 10 minutes at 640×g, and passing the supernatant through 0.45-µm filters to reduce bacterial contamination. An aliquot of 100 µl was plated on confluent, PBS-washed MDCK cells in 48-well plates. After incubation for 1 hour at 37° C., 500-µl serum-free MEM supplemented with 1 µg/ml TPCK trypsin and antibiotics was added. All wells were evaluated for cytopathic effects after 48-72 hours. Subsequently, plates were fixed with 4% phosphate-buffered formaldehyde and stained as described above. BALF was tested for the presence of PRRSV and *M. hyopneumoniae* by diagnostic PCR assays. For PRRSV, the total RNA was isolated from each sample by using the RNeasy Mini Kit (Qiagen). One microgram of the extracted RNA and a primer pair specific for ORF 7 of PRRSV were used in real-time PCR as described in Lekcharoensuk et al. (2006, *Emerg Infect Dis* 12:787-794). DNA was extracted from BALF for detecting *M. hyopneumoniae* as described in Lekcharoensuk et al. (2006, *Emerg Infect Dis* 12:787-794).

Examination of Lungs of Experimental Pigs. At necropsy, lungs were removed in toto. A single veterinarian recorded the percentage of gross lesions of lobes showing the purple-red consolidation typical of swine influenza virus infection. A mean value was determined for the seven pulmonary lobes of each animal (Richt et al., 2003, *J Clin Microbiol* 41:3198-3205). Tissue samples from the trachea, the right cardiac pulmonary lobe, and other affected lobes were fixed in 10% buffered formalin, routinely processed, and stained with hematoxylin and eosin for histopathologic examination. Lung sections were given a score of 0 to 3 to reflect the severity of bronchial epithelial injury (Richt et al., 2003, *J Clin Microbiol* 41:3198-3205) according to the following criteria: 0.0, no significant lesions; 1.0, a few airways showing epithelial damage and light peribronchiolar lymphocytic cuffing, often accompanied by mild focal interstitial pneumonia; 1.5, more than a few airways affected (up to 25%), often with mild focal interstitial pneumonia; 2.0, 50% of airways affected, often with interstitial pneumonia; 2.5, approximately ≈75% of airways affected, usually with significant interstitial pneumonia; 3.0, >75% of airways affected, usually with interstitial pneumonia. A single pathologist scored all slides and was blind to the treatment groups.

Experiments in Mice. Six- to 7-week old BALB/c mice, bred in the mouse facility of the NADC in Ames, Iowa, were used for infectivity experiments. All experiments were in compliance with the Institutional Animal Care and Use Committee of the NADC. Animals were weighed and anesthetized with isoflurane USP (Phoenix Pharmaceutical) before intranasal inoculation with $10^2$-$10^6$ $TCID_{50}$ of H2N3 virus (Sw/4296424) in a volume of 50 µl. Weight was recorded once daily, and general health status was observed twice daily. After onset of disease, general health status was observed three times per day. Surviving mice were euthanized on day 14 p.i., and the lungs were collected. The right lung was stored in an Eppendorf tube at −80° C. for virus detection, and the left lung was fixed in 10% formalin for histopathologic analysis. Virus detection was done in a 10% tissue homogenate in PBS (homogenized twice for 1 min in a Mini Bead-Beater-8; Biospec Products). The homogenate was centrifuged at 640×g for 5, minutes and the supernatant was transferred to 1.5-ml reaction tubes for RNA isolation. Real-time RT-PCR was used to detect viral RNA as described in Richt et al. (2004, *J Vet Diagn Invest* 16:367-373). Experiments in Ferrets. Influenza-negative ferrets were obtained through the ferret breeding program and were housed at St. Jude Children's Research Hospital in compliance with the St. Jude Children's Research Hospital Animal Care and Use Committee. Infection and transmissibility of H2N3 was tested in six 18-week-old ferrets. Three ferrets were inoculated intranasally with $10^{2.5}$ $TCID_{50}$ of H2N3 (Sw/2124514). Twenty-four hours p.i., one naive contact animal was introduced into the cage of each inoculated animal. Nasal washes were collected on days 1, 4, and 7 p.i., and virus was titrated in embryonated eggs. Egg 50% infective dose (EID50) values were calculated by the Reed-Muench method (Reed and Muench, 1938, *Am J Hyg* 27:493-497). Seroconversion was determined after 21 days by determining the serum eutralizing antibody titers of the inoculated and contact ferrets, as described in Richt et al. (2004, *J Vet Diagn Invest* 16:367-373).

Results

Analysis of Clinical Samples. In the second outbreak, the influenza virus A/Swine/Missouri/4296424/2006 (Sw/4296424) was isolated from several 5- to 6-week-old pigs with multifocal bronchopneumonia at a multisourced commercial swine nursery. Lung lesions included moderate, subacute to chronic, purulent bronchopneumonia and interstitial pneumonia with bronchiolitis and peribronchitis. Lung tissue was negative for porcine reproductive and respiratory syndrome virus (PRRSV), porcine circovirus type 2 (PCV2), and *M. hyopneumoniae* but was positive for *Streptococcus suis*. Because of the characteristic influenza-like lesions and clinical signs of pneumonia, lung tissue homogenate was inoculated on MDCK cells. Cytopathic effects were detected on day 3 postinoculation (p.i.). The influenza virus nucleoprotein (NP) gene was detected in the infected cells by RT-PCR. The virus did not react with reference swine anti-sera (A/Sw/IA/1973 H1N1, A/Sw/TX/1998 H3N2, A/Sw/NC/2001 H1N1) in HI assays, and multiplex RT-PCR detected no H1N1 or H3N2 genes (Choi et al., 2002, *J Vet Diagn Invest* 14:62-65). The virus was submitted to the NADC for subtyping and sequencing.

After the isolate had been subtyped and sequenced (described below), a search of case records revealed that another "untypable" influenza isolate had been submitted five months earlier. A/Swine/Missouri/2124514/2006 (Sw/2124514) had been isolated from a 12-week-old pig with respiratory disease at another commercial grower-finisher swine farm. Lung lesions were histopathologically characteristic of swine influenza (severe, subacute inflammation of alveoli and bronchi with bronchiolar epithelial cell necrosis and metaplasia). The lung was negative for PRRSV, PCV2, and *M. hyopneumoniae* but was positive for influenza A virus by RT-PCR (specific for the NP gene) and *S. suis*. The virus was submitted to the NADC for subtyping and sequencing.

Subtyping and Phylogenetic Analysis. To identify and characterize both influenza viruses, nucleic acid sequencing and molecular and phylogenetic analysis were conducted. Both viruses were directly sequenced from low-passage isolates by using MDCK cells, and the sequences were confirmed after plaque purification and resequencing. They were identified as H2N3 viruses by nucleotide sequence and a BLAST search of the Influenza Sequence Database. The HA gene segment of Sw/4296424 most closely matched those of H2 viruses isolated from mallards in North America [up to 97.8% nucleotide sequence identity, see Table 1]. Its NA segment was closely related to that of an H4N3 avian influenza virus (AIV) isolated from bluewinged teal (98.3% identity). With the exception of the polymerase acidic (PA) gene, its internal genes were derived from contemporary triple-reassortant swine influenza viruses currently found in the United States. These viruses carry internal genes from human (PB1), avian (PB2, PA), and swine [NP, matrix (M), nonstructural (NS)] influenza virus origin (Table 1). Its PA segment was 99.2% identical to that of the H6N5 AIV isolated from mallard ducks (Table 1). The Sw/2124514 and Sw/4296424 viruses showed 99.3-99.9% total nucleotide sequence identity (Table 2). Both isolates were repeatedly plaque cloned, retested, and confirmed by sequencing to belong to the H2N3 subtype. The H2N3 subtype was serologically confirmed by hemagglutination inhibition and neuraminidase inhibition assays. Phylogenetic analysis based on the HA and NA genes showed that these two viruses belong to the American avian lineage that is distinct from the Eurasian avian strains and the H2N2 viruses isolated from humans after the 1957 influenza pandemic (FIG. 1).

TABLE 1

Influenza A viruses with greatest nucleotide sequence identity to H2N3 swine influenza virus (A/Swine/Missouri/4296424/2006) as determined by a Blast search of the Influenza Sequence Database

| Gene | Identity (%) | Virus designation | Subtype | GenBank accession no. |
|---|---|---|---|---|
| HA | 97.8 | A/Mallard/Alberta/79/2003 | H2N3 | CY003992 |
|  | 97.1 | A/Mallard/Alberta/149/2002 | H2N4 | CY003984 |
| NA | 98.3 | A/blue-winged teal/Barbados/21/04 | H4N3 | DQ236167 |
|  | 98.2 | A/GSC_chicken_B/British Columbia/04 | H7N3 | AY648289 |
| PB1 | 97.8 | A/Swine/Minnesota/00395/2004* | H3N1 | DQ145544 |
|  | 97.7 | A/Wisconsin/10/98 | H1N1 | AF342823 |
| PB2 | 97.8 | A/Swine/Illinois/100084/01† | H1N2 | AF455738 |
|  | 97.8 | A/Swine/Korea/CY02/02† | H1N2 | AY129163 |
| PA | 99.2 | A/Mallard/Alberta/154/2003 | H6N5 | CY004279 |
|  | 97.2 | A/Mallard/Maryland/881/2002 | H6N2 | CY011117 |
| NP | 98.3 | A/Swine/Michigan/PU243/04 | H3N1 | DQ150426 |
|  | 97.9 | A/Swine/Indiana/PU542/04 | H3N1 | DQ150434 |
| M | 98.7 | A/Swine/Indiana/PU542/04 | H3N1 | DQ150436 |
|  | 98.4 | A/Swine/Ontario/33853/2005 | H3N2 | DQ469993 |
| NS | 97.2 | A/Swine/Indiana/14810-S/01 | H1N2 | AY060136 |
|  | 97.2 | A/Swine/Indiana/14810-T/01 | H1N2 | AY060135 |

*Triple reassortant virus, PB1, derived from human influenza virus.
†Triple reassortant virus, PB2, derived from avian influenza virus.

TABLE 2

Sequence comparison of Sw/4296424 and Sw/2124514

| Segment | Identity, nt | Identity, aa |
|---|---|---|
| PB1 | 99.3% | 99.3% |
| PB2 | 99.7% | 99.7% |
| PA | 99.9% | 99.9% |
| HA | 99.4% | 99.5% |
| NP | 99.6% | 99.6% |
| NA | 99.7% | 99.4% |
| M | 99.8% | 100%* |
| NS | 99.5% | 99.5%† |

*M1 protein identity.
†NS1 protein identity.

Molecular Analysis of the HA and NA Surface Proteins. Influenza A viruses contain two surface proteins: the HA is the receptor binding and membrane-fusion glycoprotein, and the NA is a receptor-destroying enzyme. The viral HA is a critical factor of host species specificity of influenza viruses (Neumann et al., 2006, *Emerg Infect Dis* 12:881-886). To characterize residues within HA that may be associated with adaptation of an avian virus to the mammalian host, the amino acid sequences of swine HAs were compared with those of the putative reference avian viruses. Molecular comparison of the HA molecules of the two swine H2N3 isolates revealed that they differ from the putative reference H2N3 virus isolated from mallards by six common amino acid substitutions (D36N, Q226L, T274I, V316I, L419I, and L506V) (Table 3). The substitution Q226L was found in both swine H2N3 isolates, whereas position 228 contained G, identical to the avian consensus sequence (Table 4) (Matrosovich et al., 1997, *Virology* 233:224-234). In contrast, human HA molecules of H2 subtype contain 226L and 228S, whereas early human H2 isolates contain 226L and 228G (Table 4), similar to the swine isolates. Positions 36N, 274I, 316I, and 419I are unique to the two swine H2N3 isolates (Table 3), whereas the respective positions in human and avian isolates depicted in FIG. 1a are 36D, 274T, 316V, and 419L. For the influenza isolates depicted in FIG. 1a, position 506V is conserved among human, two swine H2N3 isolates, and the avian isolates, except for A/mallard/Alberta/2004 (H2N3) as shown in Table 3. Two common amino acid changes in the NA amino acid sequence of both swine isolates were found when compared with the reference H4N3 virus isolated from blue-winged teal: H47Y and H253Y (Table 5). The position 47Y in both swine H2N3 isolates is the same as the respective amino acid in Eurasian avian isolates depicted in FIG. 1b; conversely, the position in North American avian isolates is 47H. The position 253Y is unique to the swine H2N3 isolates, and the position 253H is conserved in Eurasian and North American avian isolates depicted in FIG. 1b. Interestingly, Sw/4296424

(H2N3), isolated 5 months later than Sw/2124514 (H2N3), had two additional substitutions (P162S and L321V) in the HA molecule, and had three additional substitutions (V30I, 149T, and A 35T) in the NA molecule when compared with the HA and NA of Sw/2124514 (Table 3 and 5). The position 30I (Sw/4296424) in the NA molecule is similar to Eurasian isolates, whereas the position 30V (Sw/2124514) is conserved in Northern American avian isolates.

TABLE 3

Amino acid changes in HA compared to that of A/Mallard/Alberta/2003 (H2N3)

| AA position | Mallard/03/H2N3 | Sw/2124514 | Sw/4296424 |
|---|---|---|---|
| 46†/36* | D | N | N |
| 172†/162* | P | P | *S* |
| 236†/226* | Q | L | L |
| 284†/274* | T | I | I |
| 326†/316* | V | I | I |
| 331†/321* | L | L | *V* |
| 429†/419* | L | I | I |
| 500†/490* | P | I | P |
| 516†/506* | L | V | V |

Sw/2124514 was isolated in the first outbreak. Sw/4296424 was isolated in the second outbreak. Letters in boldface indicated substitutions in both swine H2N3 isolates; letters in italics indicated substitutions only in the Sw/4296424 isolate.
†H2 numbering system.
*H3 numbering system.

TABLE 4

Comparison of amino acids in HA receptor-binding sites of human, avian, and swine H2 influenza virus isolates

| | HA receptor-binding residues | | | | | |
|---|---|---|---|---|---|---|
| Virus strains | 138/148 | 190/200 | 194/204 | 225/235 | 226/236 | 228/238 |
| AIV consensus | A | E | L | G | Q | G |
| Mallard/2003/H2N3 | A | E | L | G | Q | G |
| Sw/4296424 | A | E | L | G | L | G |
| Sw/2124514 | A | E | L | G | L | G |
| Human consensus | A | E | L | G | L | G/S |
| Davis/1/57 | A | E | L | G | L | G |
| Albany/7/57 | A | E | L | G | L | G |
| RI/5+/57 | A | E | L | G | L | S |
| Albany/6/58 | A | E | L | G | L | S |
| Ohio/2/59 | A | E | L | G | L | S |
| Berlin/3/64 | A | E | L | G | L | S |

Under HA receptor-binding residues, the H3 numbering system is used for numbers before the slash, and the H2 numbering system is used for numbers after the slash. The Davis/1/57 and Albany/7/57 viruses were isolated earlier in the human H2 pandemic when compared to the other H2 human viruses listed here.

TABLE 5

Amino acid changes in NA compared to that of A/Blue-winged teal/Barbados/21/2004 (H4N3)

| AA position | Teal/04/H4N3 | Sw/2124514 | Sw/4296424 |
|---|---|---|---|
| 30 | V | V | *I* |
| 47 | H | Y | Y |
| 49 | T | *I* | T |
| 134 | A | A | *T* |
| 253 | H | Y | Y |

Sw/2124514 was isolated in the first outbreak. Sw/4296424 was isolated in the second. Letters in boldface indicated substitutions in both swine H2N3 isolates; letters in italics indicated substitutions only in the Sw/4296424 isolate.

Pathogenicity and Transmissibility of H2N3 Swine Influenza Viruses in Pigs. To investigate the extent of swine adaptation of the H2N3 virus, its pathogenicity in this host was investigated by inoculating 20 4-week-old pigs with $2 \times 10^6$ 50% $TCID_{50}$ of the Sw/4296424 virus. Only one H2N3 virus was chosen, because of the high identity between the two isolates. Twelve control pigs were mock-inoculated with non-infectious cell culture supernatant. Transmissibility was assessed by co-housing 10 age-matched contact pigs with the inoculated pigs, starting on day 3 p.i. All pigs used for the study were seronegative at day 0 for antibodies against swine influenza H1N1, H1N2, H2N3, and H3N2 viruses by HI assay. Five inoculated pigs and three control pigs were euthanized for necropsy on days 3, 5, and 7 p.i. The 10 contact pigs and 5 virus-inoculated pigs were serologically tested by HI assay with H2N3 on day 24 after contact or day 27 p.i., respectively. No acute respiratory signs were observed. Necropsy revealed severe macroscopic lung lesions (plum-colored, consolidated areas) in inoculated pigs but revealed none in control pigs (Table 2). The histopathologic score (0-3) expressing the extent of damage to lung architecture was >2 in inoculated pigs (Table 6). Lungs from inoculated pigs euthanized on day 3, 5, or 7 p.i. exhibited mild to moderate interstitial pneumonia and acute to subacute necrotizing bronchiolitis with slight lymphocytic cuffing of bronchioles and vessels (FIG. 2). Virus was titrated in bronchoalveolar lavage fluid (BALF) and isolated from nasal swab samples. Virus titers in the lung ranged from $10^{4.3}$ to $10^{6.5}$ $TCID_{50}$/ml on days 3 and 5 p.i. (Table 7) and were negative on day 7 p.i. In the H2N3 inoculated group, virus was isolated from nasal swab samples in 25% (5 of 20) of pigs on day 3, 67% (10 of 15) on day 5, and 20% (2 of 10) on day 7 p.i.; in the contact group, 10% (1 of 10) of samples were positive on days 5 and 7 after contact. In contrast, 100% (10 of 10) of the contact pigs were seropositive after 24 days of contact with inoculated pigs (Table 8). Some control pigs had an occasional small focus of mild interstitial pneumonia (Table 6), but they were negative for swine influenza virus infection. All pigs were negative for PRRSV and *M. hyopneumoniae* by PCR. These results indicate that the H2N3 virus is pathogenic in pigs and is transmissible among pigs.

TABLE 6

Macroscopic and microscopic pneumonia in pigs inoculated with H2N3 virus Sw/4296424 or mock-inoculated

| Group | Lung lesion score, % | Histopathologic Score (0-3) |
|---|---|---|
| H2N3 day 3 | 27.57 ± 7.36 | 2.23 ± 0.23 |
| Control day 3 | 0.00 ± 0.00 | 0.33 ± 0.09 |
| H2N3 day 5 | 21.86 ± 2.90 | 2.37 ± 0.11 |
| Control day 5 | 0.00 ± 0.00 | 0.56 ± 0.06 |
| H2N3 day 7 | 21.57 ± 5.02 | 2.07 ± 0.25 |
| Control day 7 | 0.00 ± 0.00 | 0.22 ± 0.11 |

Values are the mean ± SEM.

TABLE 7

Virus titers ($TCID_{50}$/ml) in bronchoalveolar lavage fluid 3 and 5 days after virus inoculation in pig challenge experiment with H2N3 virus

| Pig No. | Day 3 | Pig No. | Day 5 |
|---|---|---|---|
| 405 | $10^{6.50}$ | 409 | $10^{5.50}$ |
| 406 | $10^{6.50}$ | 410 | $10^{4.50}$ |
| 407 | $10^{4.77}$ | 411 | $10^{6.50}$ |
| 408 | $10^{4.33}$ | 412 | $10^{5.77}$ |
| 417 | $10^{5.77}$ | 413 | $10^{4.50}$ |

The average virus titers on days 3 and 5 were $10^{6.15}$ and $10^{5.92}$ $TCID_{50}$/ml, respectively.

TABLE 8

Seroconversion of inoculated and contact pigs at different time points in pig challenge experiment with H2N3 virus

| Day | Inoculated pigs | Contact pigs |
|---|---|---|
| Day 14 | 5/5* (92) | 2/10* (20) |
| Day 24/27 | 5/5* (70) | 10/10* (32) |

Number in parentheses indicate serum geometric mean HI titer of positive pigs (lower limit of positivity: 1:20). The inoculated pigs were euthanized at day 27 and contact pigs were euthanized at day 24. All control pigs (n = 12) were negative for influenza-specific antibodies throughout the study.
*Number of positive pigs/number of tested pigs.

Pathogenicity of H2N3 Swine Influenza Viruses in Mice. To test the ability of the H2N3 Sw/4296424 virus to replicate in mice, 6- to 7-week-old BALB/c mice were inoculated intranasally with $10^2$-$10^6$ TCID$_{50}$. Mice inoculated with 104 TCID$_{50}$ or more showed signs of disease (e.g., labored breathing, rough fur, weight loss, and lethargy) (Table 9). Seventy-five percent of mice that received 106 TCID$_{50}$ died, but there were no deaths at lower doses. Viral RNA was detected by real-time RT-PCR (Richt et al., 2004, J Vet Diagn Invest 16:367-373) in the lungs of mice after inoculation with $10^6$ or $10^5$ TCID$_{50}$ (Table 9). Histopathologically, the H2N3 virus induced multiple or coalescing foci of interstitial pneumonia and proliferative alveolitis characterized by prominent pneumocyte hypertrophy and infiltration of alveolar walls with a mixed population of macrophages, lymphocytes, and neutrophils (FIG. 3). Some alveolar lumens contained fibrin clots and light mixed leukocytic exudates. Taken together, these findings indicate that H2N3 is pathogenic in mice without previous adaptation.

TABLE 9

Mouse challenge experiment with H2N3 virus

| Virus dose TCID$_{50}$ | Percentage of mice with clinical signs | Percentage of mice that died | Virus detected in lung tissue |
|---|---|---|---|
| $10^6$ | 4/4 | 3/4 | 4/4 |
| $10^5$ | 4/4 | 0/4 | 4/4 |
| $10^4$ | 4/4 | 0/4 | n.d |
| $10^3$ | 0/4 | 0/4 | n.d |
| $10^2$ | 0/4 | 0/4 | n.d |

Virus detected in lung tissue by real-time RT-PCR. n.d., not done.

Transmissibility of H2N3 Swine Influenza Virus in Ferrets. To cause a pandemic, an emergent influenza A virus must infect humans and be efficiently transmitted among humans. To investigate the potential of the reassortant H2N3 virus to transmit in mammalian systems, the ferret contact model (Herlocher et al., 2001, *J Infect Dis* 184:542-546) was used. Three 18-week-old ferrets, housed in separate cages, were inoculated with $10^{2.5}$ TCID$_{50}$ of the H2N3 virus Sw/2124514. After 24 hours, one contact animal was placed in each cage. Nasal washes were taken on days 1, 4, and 7 p.i., and virus was titrated in embryonated eggs. Virus was detected in all inoculated and contact ferrets, but none showed obvious clinical signs (Table 10). These results indicate that the H2N3 influenza virus infected ferrets and was transmitted via contact efficiently.

TABLE 10

Virus titers in nasal washes from H2N3 (Sw/2124514)-inoculated and contact ferrets.

| Animal | Virus titer, EID$_{50}$/ml | | | HI titer | |
|---|---|---|---|---|---|
| | Day 1 | Day 4 | Day 7 | Day 21 | Day 28 |
| Inoculated #333 | $10^{4.8}$ | $10^{5.5}$ | $<10^{1.0}$ | 1:160 | 1:160 |
| Contact #362 | $<10^{1.0}$ | $10^{6.3}$ | $10^{6.5}$ | 1:320 | 1:320 |
| Inoculated #366 | $10^{6.0}$ | $10^{5.5}$ | $<10^{1.0}$ | 1:320 | 1:160 |
| Contact #334 | $<10$ | $10^{5.8}$ | $10^{7.0}$ | 1:320 | 1:320 |
| Inoculated #368 | $10^{5.8}$ | $10^{4.5}$ | $<10^{1.0}$ | 1:160 | 1:320 |
| Contact #364 | $<10^{1.0}$ | $10^{6.8}$ | $10^{6.3}$ | 1:320 | 1:320 |

Serological Investigation of H2N3 Swine Influenza Viruses in Outbreak Farms. To further investigate the spread of the H2N3 viruses, a serological survey of animals associated with the two affected production systems was conducted. In the first study, serum samples were taken from sows from four farms that provided piglets to the nursery farms during the second outbreak. Ninety percent (54 of 60) were seropositive for the presence of antibodies to Sw/4296424 (Table 11). A number of the tested animals were present at the time of the index case, and it is unclear whether they were infected at that time or whether they were infected subsequently. The data do, however, show that the virus was present at both sow and nursery farms and that the virus efficiently transmitted between animals. All sows in this operation had antibody titers >1:40 to H1N1 and H3N2 swine influenza viruses, because they had been previously vaccinated with a bivalent H1N1 and H3N2 killed-influenza vaccine. Serum samples were also collected about a year after the first outbreak from 30 sows and 90 weaned pigs associated with the first outbreak, and they were tested for the presence of antibodies to Sw/2124514 by using the HI assay. Of the 30 sows and 90 weaned pigs sampled, 1 of 30 and 26 of 90 were seropositive (Table 11), respectively.

TABLE 11

HI antibody responses to A/Swine/Missouri/2124514/2006 (H2N3) in sows or weaned pigs associated with the first outbreak (Operation A) and to A/Swine/Missouri/4296424/2006 (H2N3) in sows that provided pigs to the farms during the second outbreak (Operation B)

| | Operation A | | Operation B |
|---|---|---|---|
| HI response | sows† | weaned pigs | sows* |
| No. of tested | 30 | 90 | 60 |
| Titer range | Negative to 160 | Negative to 640 | Negative to 640 |
| Seropositive (%) | 3.3% (1/30) | 28.9% (26/90) | 90.0% (54/60) |
| GMT | 57 | 59 | 175 |

GMT, geometric mean titer for samples > 10. _Seropositive indicates a positive antibody titer (HI ≧ 40) in serum samples,
†sows were from six farms (15 sows per farm).
*Sows were from four farms (15 sows per farm).

Discussion

This example characterizes reassortant H2N3 viruses isolated from pigs in the United States. Molecular and phylogenetic analysis revealed that the HA, NA, and PA gene segments are similar to those of AIVs of the American lineage, whereas other gene segments are similar to those of contemporary swine influenza viruses that are triple-reassortant viruses containing human, avian, and swine influenza virus genes. In addition to their potential impact on animal health, these H2N3 viruses have intrinsic properties that make them of considerable concern to public health. These properties include the following: (i) they belong to the H2 subtype as did the 1957 human pandemic strain that disappeared in 1968 (hence, individuals born subsequent to 1968 have little pre-existing immunity to this subtype); (ii) they are circulating in swine, a host shown experimentally to select for mammalian virus traits (Ito et al., 1998, *J Virol* 72:7367-7373); (iii) they have receptor binding site changes associated with increased affinity for α2,6Gal-linked sialic acid viral receptors; and (iv) they are able to replicate and transmit in swine and ferrets via contact. The latter two points suggest that the swine H2N3 viruses have undergone adaptation to the mammalian host and as such have the ability for sustained transmission. Reinforcing this possibility is the finding in one of the production systems that young pigs born at least 6 months after the index case were seropositive for the virus. Although it is not clear whether the seropositivity in the young animals was due to infection or maternal antibodies, these data suggest that the virus continues to circulate within the affected production systems. The fact that the H2N3 viruses are known to have infected two independent swine production systems and that serologic studies suggest they continue circulating is in contrast to other reports of a wholly AIV infection in North American swine, in which infections have appeared to be self-limiting (Karasin et al., 2000, *J Virol* 74:9322-9327 and Karasin et al., 2004, *J Clin Microbiol* 42:4349-4354).

Although the genetic factors that are associated with successful zoonotic transmission of influenza viruses remain largely unknown, receptor-binding properties are likely involved. In avian H2 and H3 influenza viruses, HA receptor-binding-site residues corresponding to codon positions 138, 190, 194, 225, 226, and 228 (using the H3 numbering system) are highly conserved (Matrosovich et al., 1997, *Virology* 233: 224-234). In human H2 and H3 viruses, leucine and serine substitutions at residues 226 and 228, respectively, have been shown to accompany their adaptation from avian to human hosts (Connor et al., 1994, *Virology* 205:17-23). For example, changing the human virus H3 residue L226 to Q226 dramatically changes the receptor-binding specificity of the virus from mammalian to avian virus-like (Rogers et al., 1983, *Nature* 304:76-78). The substitution Q226L was found in both new swine H2N3 isolates, whereas position 228 retains G, which is typical of AIVs (Table 4). This same 226L/228G combination was observed in the first viruses of the 1957 H2N2 human pandemic. The later pandemic strains contained 228S after full adaptation to humans (Matrosovich et al., 2000, *J Virol* 74:8502-8512). In addition to the genetic signatures, biologic evidence also suggests that the H2N3 viruses have undergone adaptation to mammalian hosts as evidenced by replication in mice, swine, and ferrets, with efficient transmission via contact in the latter two. Strong support for the importance of receptor-binding changes on transmissibility of influenza viruses has come from studies of the 1918 H1N1 pandemic strain. Investigators using genetically reconstructed virus were able to show that substitution of only two amino acids in the receptor binding site of this virus was enough to abolish transmission among ferrets (Tumpey et al., 2007, *Science* 315:655-659). Although the evidence that receptor-binding changes are required for the successful adaptation of avian viruses in humans is strong, it should also be noted that this trait on its own is not sufficient. Classical swine H1N1 influenza viruses, for example, have a preference for α2,6Gal-linked sialic acid viral receptors (Ito et al., 1998, *J Virol* 72:7367-7373). Despite this preference and a number of self-limiting human infections, these viruses have not successfully established in the human population, suggesting that other host range barriers exist, reducing the transmission of swine influenza viruses between humans. An examination of the other viral proteins shows that a number of substitutions are present when H2N3 isolates were compared with influenza viruses isolated from swine or mallard ducks, although their significance is unknown (Tables 12-17).

TABLE 12

PB1 amino acids of Sw/4296424 and Sw/2124514 compared to those of A/Swine/Minnesota/00395/2004 (H3N1)

| AA position | Sw/04/H3N1 | Sw/2124514 | Sw/4296424 |
|---|---|---|---|
| 57 | T | T | *I* |
| 86 | D | D | *E* |
| 154 | G | S | S |
| 165 | D | *N* | D |
| 176 | K | R | R |
| 179 | I | *V* | *M* |
| 186 | Q | *R* | Q |
| 212 | V | L | L |
| 213 | N | S | S |
| 216 | G | S | S |
| 456 | H | Y | Y |
| 464 | D | N | N |
| 584 | Q | R | R |
| 586 | K | N | N |
| 687 | R | Q | Q |
| 744 | M | I | I |
| 745 | K | R | R |
| 757 | K | T | T |

Sw/2124514 was isolated in the first outbreak. Sw/4296424 was isolated in the second outbreak. Letters in boldface indicated substitutions in both swine H2N3 isolates; letters in italics indicated substitutions only in the Sw/4296424 isolate.

TABLE 13

PB2 amino acids of Sw/4296424 and Sw/2124514 compared to those of A/S wine/Illinois/100084/01 (H1N2)

| AA position | Sw/01/H1N2 | Sw/2124514 | Sw/4296424 |
|---|---|---|---|
| 102 | S | N | N |
| 106 | T | A | A |
| 136 | K | R | R |
| 155 | S | R | *S* |
| 209 | R | K | K |
| 228 | H | Y | Y |
| 229 | Y | Z | Z |
| 246 | S | P | P |
| 340 | K | R | R |
| 528 | T | A | A |
| 540 | N | S | S |
| 573 | T | N | N |
| 608 | L | I | I |
| 674 | A | E | E |
| 756 | M | M | *T* |

Sw/2124514 was isolated in the first outbreak. Sw/4296424 was isolated in the second outbreak. Letters in boldface indicated substitutions in both swine H2N3 isolates; letters in italics indicated substitutions only in the Sw/4296424 isolate.

TABLE 14

PA amino acids of Sw/4296424 and Sw/2124514 PA compared to those of A/Mallard/Alberta/154/2003 (H6N5)

| AA position | Mallard/H6N5 | Sw/2124514 | Sw/4296424 |
|---|---|---|---|
| 115 | S | N | N |
| 129 | V | I | I |
| 335 | L | F | F |
| 369 | A | A | *V* |
| 565 | V | I | I |

Sw/2124514 was isolated in the first outbreak. Sw/4296424 was isolated in the second outbreak. Letters in boldface indicated substitutions in both swine H2N3 isolates; letters in italics indicated substitutions only in the Sw/4296424 isolate.

TABLE 15

NP amino acids of Sw/4296424 and Sw/2124514 NP compared to those of A/Swine/Michigan/PU243/04 (H3N1)

| AA position | Sw/04/H3N1 | Sw/2124514 | Sw/4296424 |
|---|---|---|---|
| 37 | K | R | R |
| 67 | I | M | M |
| 140 | T | A | A |
| 195 | I | I | *V* |
| 220 | R | K | K |
| 223 | V | I | I |
| 363 | K | R | R |
| 431 | V | V | *I* |
| 452 | K | R | R |
| 456 | S | N | N |

Sw/2124514 was isolated in the first outbreak. Sw/4296424 was isolated in the second outbreak. Letters in boldface indicated substitutions in both swine H2N3 isolates; letters in italics indicated substitutions only in the Sw/4296424 isolate.

TABLE 16

NS1 amino acids of Sw/4296424 and Sw/2124514 NS1 compared to those of A/Swine/Indiana/14810-S/01 (H1N2)

| AA position | Sw/01/H1N2 | Sw/2124514 | Sw/4296424 |
|---|---|---|---|
| 4 | N | T | T |
| 75 | E | D | D |
| 96 | K | E | E |
| 98 | M | M | *I* |
| 103 | F | L | L |
| 155 | A | T | T |
| 162 | P | Q | Q |
| 178 | V | I | I |
| 218 | Q | K | K |

Sw/2124514 was isolated in the first outbreak. Sw/4296424 was isolated in the second outbreak. Letters in boldface indicated substitutions in both swine H2N3 isolates; letters in italics indicated substitutions only in the Sw/4296424 isolate.

TABLE 17

NEP amino acids of Sw/4296424 and Sw/2124514 NEP compared to those of A/Swine/Indiana/14810-S/01 (H1N2)

| AA position | Sw/01/H1N2 | Sw/2124514 | Sw/4296424 |
|---|---|---|---|
| 4 | N | T | T |
| 60 | S | R | R |
| 89 | A | T | T |

Sw/2124514 was isolated in the first outbeak. Sw/4296424 was isolated in the second outbreak. Letters in boldface indicated substitutions in both swine H2N3 isolates.

Although the original source of the H2N3 virus is unclear, both farms use surface water collected in ponds for cleaning barns and watering animals. Considering the swine were housed in barns that prevented intrusion of birds, especially waterfowl, it seems probable the avian virus was introduced into the animals via water, a mode of transmission that has been described before (Karasin et al., 2000, *J Virol* 74:9322-9327, Karasin et al., 2004, *J Clin Microbiol* 42:4349-4354, and Brown et al., 2007, *Avian Dis.,* 51:285-289). As more reports emerge linking the use of untreated pond water to the transmission of AIVs to swine, the risks associated with this practice must be fully evaluated. The appearance of the two highly identical H2N3 viruses in both production systems is unexplained because there is no known relationship between the farms in terms of sharing of equipment, of common feed or water source, or of the movement of animals, workers, or veterinarians.

Pigs are purported to be a mixing vessel for avian and human influenza viruses because their tracheal epithelial cells carry receptors for both human and avian influenza viruses (Ito et al., 1998, *J Virol* 72:7367-7373). Supporting this theory is the documentation of genetic reassortment between avian- and human-like influenza viruses in Italian pigs (Castrucci et al., 1993, *Virology* 193:503-506). In this light, pigs have often been implicated in the emergence of human pandemic strains. More recent evidence has, however, shown that similar receptor expression is also available in the human and quail host (Wan and Perez, 2006, *Virology* 346:278-286 and Shinya et al., 2006, *Nature* 440:435-436), and the direct evidence that human pandemic viruses are generated in swine is ambiguous. Nevertheless, our results provide further evidence for the potential of swine to promote reassortment between different influenza viruses, and the genetic and biologic properties of the H2N3 viruses described suggest that it would be prudent to establish vigilant surveillance in pigs and in workers who have occupational exposure.

Example 2

Vaccine Development

To prepare the vaccine, H2N3 influenza virus was grown in MDCK cells and diluted to approximately 128 HA units. The virus was then UV-inactivated and a commercial adjuvant was added at a 1:5 ratio (Emulsigen, MVP Laboratories, Inc., Ralston, Nebr.). The inactivated vaccine was given intramuscularly to five pigs at a dose of 128 HA units in one ml per pig at 5 and 7 weeks of age. Another group of five pigs received one live exposure to the H2N3 virus at 4 weeks of age with 2 ml of $1 \times 10^6$ TCID$_{50}$/ml given intratracheally while anesthetized. A challenge control group of five pigs received no vaccine. At approximately 10 weeks of age, pigs in all groups were challenged with 2 ml of $1 \times 10^6$ TCID$_{50}$/ml of the H2N3 virus given via the intratracheal route while anesthetized. The percentage of pneumonia in the H2N3 vaccinated groups was significantly reduced when compared to the non-vaccinated H2N3 challenged group. Pigs in the H2N3 live exposure and the inactivated vaccine groups were equally protected from pneumonia, suggesting that modified live-virus vaccine or inactivated vaccine will be protective against this subtype.

Diagnostic Applications

There is a critical need for diagnostic tools for rapid detection of the H2N3 swine influenza virus described herein. Serum was collected from 2 pigs hyperimmunized against the H2N3 influenza A virus. The H2N3-specific anti-sera can be used as reference sera for diagnostic applications. The reference sera will be used in the hemagglutination inhibition assay to serotype unknown influenza A virus isolates using standard techniques.

Gel-based PCR has been developed for this H2N3 subtype swine influenza virus based on sequence obtained from the two novel swine isolates. H2 PCR primers were designed for general detection and differentiation from the common swine H1 and H3 subtype viruses. In addition, N3 PCR primers were designed for general detection and differentiation from the common swine N1 and N2 subtypes. The amplified PCR products are 842 nucleotides for H2 and 1413 nucleotides for N3 genes. The oligonucleotide primer sequences are as follows: H2-Fw (21 mer) 5'-CAG GCA GTT TCA ATG ATT ATG-3' (SEQ ID NO:33), H2-Bw (20 mer) 5'-CCA TCA ATT GCC TTT TGA GT-3' (SEQ ID NO:34), N3-Fw (21 mer) 5'-AGC AAA AGC AGG TGC GAG ATG-3' (SEQ ID NO:35), and N3-Bw (24 mer) 5'-AGT AGA AAC AAG GTG CTT TTT TCT-3' (SEQ ID NO:36).

PCR was done in two-step RT-PCR. The assay was performed under the following conditions:

Reverse transcriptase step: 8 µl of RNA, 1 µl (20 pmol) of forward primer (H2-Fw or N3-Fw) and 1 µl of dNTPs (10 pmol). Incubate 70° C. for 10 minutes, then immediately on ice. The following reagents were added: 3 µl of 10×RT buffer, 5 µl of $MgCl_2$ (25 mM), 1 µl of RNaseout (10 U/µl), 9 µl of $ddH_2O$ and 1 µl of AMV RT enzyme (Promega). Incubate 42° C. for 50 minutes.

PCR step: The cDNA was amplified by using GoTaq Green Master Mix, 2× system (Promega) according to the protocols provided by the manufacturer. The reaction was as follows: 2× Green Master Mix 25 µl, H2 Fw or N3 Fw (20 µM) 1 µl, H2 Bw or N3 Bw (20 µM) 1 µl, RT products as template 5 µl and RNase-free water 18 µl were used. The first cycle of the amplification program consisted of a 4-min period at 94° C. and was followed by 30 cycles with the following conditions: 94° C. for 20 sec, 58° C. for 30 sec, and 72° C. for 1.5 min. The program ended with one cycle at 72° C. for 7 min.

OTHER DOCUMENTS

Webster et al., 1992, Microbiol Rev 56:152-179.
Lipatov et al., 2004, J Virol 78:8951-8959.
Taubenberger, 2006, Proc Am Philos Soc 150:86-112.
Kawaoka et al., 1989, J Virol 63:4603-4608.
Scholtissek, 1995, Virus Genes 11:209-215.
Liu et al., 2004, Virus Genes 29:81-86.
Munster et al., 2007, PLoS Pathog 3:e61.
Krauss et al., 2004, Vector Borne Zoonotic Dis 4:177-189.
Schafer et al., 1993, Virology 194:781-788.
Makarova et al., 1999, J Gen Virol 80 Pt 12:3167-3171
Govorkova et al., 2006, J Infect Dis 194:159-167.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An isolated polynucleotide comprising: (a) a nucleotide sequence encoding a hemagglutinin, wherein the amino acid sequence of the hemagglutinin comprises SEQ ID NO:9 or SEQ ID NO:25 and the hemagglutinin binds a mammalian cell, or (b) the full complement of the nucleotide sequence of (a).

2. A vector comprising the isolated polynucleotide of claim 1.

3. An isolated cell comprising the vector of claim 2.

4. An isolated polynucleotide comprising: (a) a nucleotide sequence encoding a hemagglutinin, wherein the amino acid sequence of the hemagglutinin comprises SEQ ID NO:37 or SEQ ID NO:38 and the hemagglutinin binds a mammalian cell, or (b) the full complement of the nucleotide sequence of (a).

5. A vector comprising the isolated polynucleotide of claim 4.

6. An isolated cell comprising the vector of claim 5.

* * * * *

SEQUENCE LISTING

<160> NUMBER OF SEQ ID NOS: 44

<210> SEQ ID NO 1
<211> LENGTH: 1805
<212> TYPE: DNA
<213> ORGANISM: influenza A virus

<400> SEQUENCE: 1

```
ttattcgtct tcagggagca aaagcagggg ttataccata gacaaccgaa caaagacaat      60
gaccatcact tttctcatcc tcctgttcac agtagtgaaa ggggaccaaa tatgcatcgg     120
ataccatgcc aacaattcca cagaaaaagt tgacacaatc ttggaacgaa acgtcaccgt     180
gactcatgcc aagaacattc ttgaaaagac gcataatgga aagttgtgca gattgagcgg     240
gatccctcca ttggaactgg gggattgcag cattgcaggt tggctccttg gaaatccgga     300
atgtgaccgg ctcttaagtg tacctgaatg gtcctatata gtggaaaagg aaaacccggt     360
gaatggtctg tgctatccag gcagtttcaa tgattatgag gaattgaaac atcttctcac     420
cagtgtgaca cactttgaga aagttaagat tctgcccaga gatcaatgga cccagcacac     480
aacaactggt ggttctcggg cctgtgcagt atctggaaac ccgtcattct taggaacat      540 ggtttggctt acaaagaaag ggtcaaacta cccaattgct aaaaggtcat acaacaacac     600
aagtggggag caaatgctgg taatatgggg gatacatcac cccaatgacg atgcggaaca     660
```

| | |
|---|---|
| gaggacactg taccagaatg tgggaacata tgtttccgtt ggaacatcaa cactaaataa | 720 |
| gaggtcaatc cctgaaatag caacaaggcc caaagtcaat ggactgggag aagaatgga | 780 |
| attctcttgg actctattgg agacatggga tgtcataaat tttgagagca ctggtaattt | 840 |
| aattgcacca gaatacggat tcaaaatatc aagagagga agctcaggaa ttatgaagac | 900 |
| agagaaaata cttgaaaatt gtgaaaccaa atgtcagacc cccttggggg caataaatac | 960 |
| aacattgccc tttcacaaca ttcacccatt gacaataggt gagtgcccca agtatgtaaa | 1020 |
| gtcagataga ctgattttgg cgacaggact aagaaatgtc ccccagattg aatcaagggg | 1080 |
| attgtttgga gcaatagctg ggtttataga aggcggatgg caaggatgg ttgatggctg | 1140 |
| gtatgggtac catcacagca atgatcaagg atcaggatat gcagcagaca agaatccac | 1200 |
| tcaaaaggca attgatggga taactaacaa agtaaattct gtgattgaaa agatgaacac | 1260 |
| tcagtttgag gctgttggga aagagttcaa caacctagag agaagactgg aaaacttaaa | 1320 |
| taaaaagatg gaagatggat ttattgatgt atggacatat aatgccgaac tcctagttct | 1380 |
| aatggaaaat gagaggacac ttgatttcca tgattctaat gtgaagaatc tgtacgataa | 1440 |
| ggtcagaatg caattgagag acaatgctaa ggaaataggg aacggatgct ttgagtttta | 1500 |
| tcataaatgt gatgatgaat gcatgaatag tgtcaggaat gggacatatg attatatcaa | 1560 |
| atatgaggaa gagtccaagc tgaacaggaa cgaaatcaaa ggagtgaaat tgagcaatat | 1620 |
| gggggtttat caaatacttg ctatatacgc tacagttgca ggctctttgt cactggcaat | 1680 |
| catgatagct gggatttctt tctggatgtg ttctaatggg tctctgcaat gcagaatttg | 1740 |
| catatgactg taagtcaatt tgtaattaaa aacacccttg tttctactaa tacgagacga | 1800 |
| tataa | 1805 |

<210> SEQ ID NO 2
<211> LENGTH: 989
<212> TYPE: DNA
<213> ORGANISM: influenza A virus

<400> SEQUENCE: 2

| | |
|---|---|
| ttaaagatga gtcttctaac cgaggtcgaa acgtatgttc tctctatcgt cccgtcaggc | 60 |
| cccctcaaag ccgagatagc acagagactc gaagacgttt tgcaggaa aaacaccgat | 120 |
| cttgaggctc tcatggaatg gctaaagaca agaccaatcc tgtcacctct gactaagggg | 180 |
| attttagggt ttgtgttcac gctcaccgtg cccagtgagc gaggactgca gcgtagacgt | 240 |
| tttgttcaga atgcccctcaa tgggaatggt gacccgaaca acatggacaa ggcggtcaaa | 300 |
| ctttacagga actaaaaag ggaaataaca ttccatgggg ccaaagaagt agcgctcagt | 360 |
| tactctgctg gtgcacttgc cagttgcatg ggcctcatat acaacagaat gggaactgtc | 420 |
| accactgagg ttgcctttgg tctggtatgc gcaacctgtg aacagattgc tgattctcag | 480 |
| catcgatccc atagacaaat ggtgacaaca ccaatccac taatcaggca cgagaacaga | 540 |
| atggtgatag ccagcacaac agctaaagca atggaacaaa tggctggatc aagcgaacaa | 600 |
| gcagcagagg ctatggaggt tgccagccag gctagacaaa tggtacaggc aatgagaaca | 660 |
| attgggactc accctagttc cagcactggt ctaaagatg atcttcttga aaatttacag | 720 |
| gcctatcaga gcggatggg agtgcaaatg caacgattca atgatcctc tcattgatgc | 780 |
| tgcaagcatc attgggattt tgcacctgat attgtggatt cttgatcgtc ttttttcaa | 840 |
| atgcatttac cgtcgcttta atacggtct gcaaagaggg ccttctacgg aaggagtgcc | 900 |
| ggagtccatg agggaagaat atcgacagaa acagcagagt gctgtggatg ttgacgatgg | 960 | tcattttgtc aacatagtgc tagagtaaa                                989

<210> SEQ ID NO 3
<211> LENGTH: 1440
<212> TYPE: DNA
<213> ORGANISM: influenza A virus

<400> SEQUENCE: 3
cgagatgaat ccgaatcaga agataataac aatcggggta gtgaatacca ctctgtcaac     60
aatagcccctt ctcattggag tgggaaactt agttttcaac acagtcatac atgagaaaat   120
aggagaccat caaatagtga cctatccaat aataacgacc cctgcagtac cgaactgcag   180
tgacactata ataacataca ataacactgt gataaacaac ataacaacaa caataataac   240
tgaagaagaa aggcctttca gtctccact accgctgtgc cccttcagag gattcttccc   300
ttttcacaag gacaatgcaa tacgactggg tgaaaacaaa gacgtcatag tcacaagaga   360
gcctatgtt agctgcgata tgacaactg ctggtccttt gctctcgcac aaggagcatt    420
gctagggacc aaacatagca atgggaccat taaagacagg acaccatata ggtctctaat   480
tcgtttccca ataggaacag ctccagtact aggaaattat aaagagatat gcattgcttg   540
gtcgagcagc agttgctttg acgggaaaga gtggatgcat gtgtgcatga cagggaacga   600
taatgatgca agtgcccaga taatatatgg agggagaatg cagactcca ttaaatcatg    660
gagaaaggac atactaagaa ctcaggagtc tgaatgccaa tgcattgacg ggacttgtgt   720
tgttgctgtc acagatggcc ctgctgctaa tagtgcagat tacagggttt actggataccg  780
ggagggaaaa ataataaagt atgaaaatgt tcccaaaaca aagatacaac acttagaaga   840
atgttcctgc tatgtggaca ttgatgtttta ctgtatatgt agggacaatt ggaagggctc   900
taacagacct tggatgagaa tcaacaacga gactatactg gaaacagggt atgtatgtag   960
taaattccac tcagacaccc ccaggccagc tgacccttca acaatgtcat gtgactcccc  1020
aagcaatgtc aatggaggac ccggagtgaa ggggtttggt ttcaaagctg gcgatgatgt  1080
atggttaggt agaacagtgt cgactagtgg tagatcgggc tttgaaatta tcaaagttac  1140
agaagggtgg atcaactctc ctaaccatgt caaatcaatt acacaaacac tagtgtccaa  1200
caatgactgg tcaggctatt ccggtagctt cattgtcaaa gccaaggact gttttcagcc  1260
ctgttttttat gttgagctta tacgagggag gcccaacaag aatgatgacg tctcttggac  1320
aagtaatagt atagttactt tctgtggact agacaatgaa cctggatcgg aaattggcc   1380
agatggttct aacattgggt ttatgcccaa gtaatagaaa aaagcacctt gtttctacta  1440

<210> SEQ ID NO 4
<211> LENGTH: 1532
<212> TYPE: DNA
<213> ORGANISM: influenza A virus

<400> SEQUENCE: 4
acccatcaat gagtgacatc gaagccatgg cgtctcaagg caccaaacga tcatatgaac     60
aaatggagac tggtgggaa cgccaggatg ccacagaaat cagagcatct gtcggaagaa   120
tgattggtgg aatcgggaaa ttctacatcc aaatgtgcac tgaactcaaa ctcagtgact   180
atgagggacg actaatccaa aatagcatga caatagagag aatggtgctc tctgcttttg   240
atgagagaag aaataaatac ctagaagagc atccccagtgc agggaaggat cctaagaaaa   300
ctggaggacc catatataga agagtagacg gaaagtggat gagagaactc attctttatg   360
acaaagaaga aataaggaga gtttggcgcc aagcaaacaa tggtgaagat gcaacagctg   420

```
gtcttgctca tatcatgatt tggcactcca atctgaatga tgccacgtac cagagaacaa      480
gagcgcttgt tcgcaccgga atggatccca gaatgtgctc tctaatgcaa ggttcaacac      540
ttcccagaag gtctggggcc gcaggtgctg cagtgaaagg agttggaaca atagcaatgg      600
aattaatcag aatgatcaaa cgtgggatca atgaccgaaa cttctggaga ggtgaaaatg      660
gacgaaagac aaggattgca tatgaaagaa tgtgcaatat tctcaaggga aaatttcaga      720
cagctgccca gagggcaatg atggatcaag tgagagaaag tcggaacccc ggaaacgctg      780
agattgaaga tctcattttc ctggcacggt cagcacttat tctaagggga tcagttgcac      840
ataagtcttg cctgcctgct tgtgtgtatg ggcttgcagt ggcaagtggg catgactttg      900
aaagggaagg gtattcactg gtcgggatag acccatttaa attactccaa aacagtcaag      960
tgttcagctt gataagacca atgaaaaacc cagctcacaa gagtcaatta gtgtggatgg     1020
catgccactc tgctgcattt gaggatctga gggtatcaag tttcatcaga gggaagaaag     1080
tgattccaag aggaaggctc tccacaagag gggttcagat tgcttcaaat gagaatgtgg     1140
aagccatgga ttccaatacc ttagagctga gaagcagata ctgggccata aggaccagaa     1200
gtggaggaaa taccaatcaa cagaaggcat ccgcgggcca gatcagtgtg caacccacat     1260
tctcagtgca acggaatctc ccttttgaaa gagcaaccgt tatggcagct ttcagcggga     1320
acaatgaagg acgacatcc gatatgcgaa cagaagttat aaggatgatg gaaaatgcaa      1380
agccagaaga tttgtccttc caggggcggg gagtcttcga gctctcggac gaaaaagcaa     1440
cgagcccgat cgtgccttcc tttgacatga gtaatgaagg atcttatttc ttcggagaca     1500
atgcagagga gtatgacagt tgaggaaaaa ta                                   1532

<210> SEQ ID NO 5
<211> LENGTH: 851
<212> TYPE: DNA
<213> ORGANISM: influenza A virus

<400> SEQUENCE: 5
caaaaagaca taatggactc cacaactgtg tcaagctttc aggtagactg tttcctttgg       60
cacatccgca aacggtttgc agacaatgga ttgggtgatg ccccattcct tgatcggctc      120
cgccgagatc aaaagtctct aaaaggaaga ggcaacaccc ttggcctcga cattgaaaca      180
gccactcttg ttgggaaaca aattgtggag tggattttga aagaagaatc cagcgataca      240
cttaagatga ctattgcatc tgtacctact tcgcgctatt tagctgacat gaccctcgag      300
gaaatgtcac gagactggtt aatgctcatg cctaggcaaa agataatagg ccctctttgt      360
gtgcgaatgg accaggcgat catggaaaag aacatcatac tgaaagcgaa cttcagtgtg      420
atctttaacc gattagagac tttgatacta ctaagggctt tcacagagga gggaacaatc      480
gttggagaaa tttcacaatt accttctctt ccaggacata ctaatgagga tgtcaaaaat      540
gcaattgggg tcctcatcgg aggacttgaa tggaatggta acacggttcg aggctctgaa      600 atctacaga gattcgcttg gagaaaccgt aatgaggatg ggagaccttc actacctcca      660
gagaagaaat gaaagtggc gagagcaatt gggacaaaaa tttgaggaaa taaggtggtt      720
aattgaagaa gtgcggcaca gattgaaaac gacagagaat agttttgaac aaataacatt      780
catgcaagcc ttacaactac tgcttgaagt agaacaagag ataaggactt tctcgtttca      840
gcttatttaa t                                                           851

<210> SEQ ID NO 6
<211> LENGTH: 2230
<212> TYPE: DNA
```

<213> ORGANISM: influenza A virus

<400> SEQUENCE: 6

```
ccaaaatgga agactttgtg cgacaatgct tcaatccaat gatcgtcgag cttgcggaaa      60
aggcaatgaa ggaatatggg gaagatccaa aaatcgaaac taacaaattc gcagcaatat     120
gcactcactt ggaagtatgt ttcatgtatt cggatttcca cttcattgat gagcggggcg     180
aatcaataat tgtggaatct ggtgatccaa atgcattact gaagcaccga tttgaaataa     240
ttgaaggaag agaccgaaca atggcctgga cagtggtgaa tagcatctgc aacaccacag     300
gggtcgagaa gcctaaattt cttccggatc tgtatgatta caaggagaac cgattcattg     360
aaattggagt aacacggaga gaggttcata tatactacct agagaaagcc aacaagataa     420
aatctgagaa gacacacatt cacatctttt catttactgg agaagaaatg ccaccaaag      480
cagactacac tcttgatgaa gaaagcaggg caagaatcaa aaccaggcta ttcactataa     540
gacaagaaat ggccagcagg ggtctatggg attcctttcg tcagtctgaa agaggcgaag     600
agacaattga ggaaagattt gaaatcacag gaaccatgcg taggcttgcc gaccaaagtc     660
tcccaccgaa cttctccagc cttgaaaact ttagagccta tgtggatgga ttcgaaccga     720
acggctgcat tgagggcaag cttttctcaaa tgtcaaaaga agtgaatgcc aggattgagc     780
cattcctgaa gacaacacca cgccctctca aattacctga tgggcccct tgctctcagc     840
ggtcaaaatt cttgctgatg gatgccttga aactaagcat cgaagacccg agtcacgagg     900
gagagggtat accactatac gatgcaatca aatgcatgaa gacattttt ggctggaaag     960
agcccaacat aatcaaacca catgagaaag gcataaatcc caattacttt ctggcttgga    1020
agcaagtgct agcagagctc caggaccttg aaaatgaaga aagatccca aagacaaaga    1080
acatgaagaa aacaagccaa ttgaagtggg cgcttggtga aatatggca ccagaaaaag    1140
tggactttga ggattgcaag gacattggcg atctaaagca gtatgatagt gatgagccag    1200
agcctagatc gctggcaagc tggatccaga gtgaattcaa taaggcatgt gaattgaccg    1260
actcgagctg gatagaactt gatgaaatag gagaagatgt tgctccgatt gaacacattg    1320
caagtatgag gaggaactat ttttacagcag aagtgtccca ctgcagggcc actgaataca    1380
taatgaaagg agtctacata aatacagctc tgctcaatgc atcttgtgca gccatggatg    1440
acttccagct gattccaatg ataagcaaat gtagaacaaa ggaaggaaga cggaaaacaa    1500
acctgtatgg gttcatcata aaaggaagat ctcatttgag gaatgatact gatgtggtaa    1560
actttgtgag catggaattt tctctcactg acccgaggct agaaccacac aaatgggaga    1620
agtattgtgt tcttgaaata ggagatatgc tcctgaggac tgcaataggc caagtgtcaa    1680
ggcccatgtt cctgtacatt agaaccaatg ggacctccaa gatcaagatg aaatgggta    1740
tggaaatgag gcgctgcctc cttcaatctc ttcaacagat tgagagcatg attgaggctg    1800
agtcttctgt caaagaaaag gacatgacta aggaattctt tgaaaacaag tcggaaacgt    1860
ggccaattgg agaatccccc agaggagtag aggaaggctc tattgggaaa gtatgcagaa    1920
ccttactggc aaagtctgta ttcaacagtc tgtacgcatc tccacaactt gagggggtttt    1980
cagctgaatc gagaaaattg cttctcattg ttcaggcact tagggacaac ctggaacctg    2040
ggaccttcga tcttgggggg ctatacgaag caattgagga gtgcctgatt aatgatccct    2100
gggtttttgct taatgcatct tggttcaact ccttcctcac acatgcactg aaatagttgt    2160
ggcaatgcta ctatttgcta tccatactgt ccaaaaaagt accttgtttc tactaataga    2220
agagcgatga                                                           2230
```

<210> SEQ ID NO 7
<211> LENGTH: 2339
<212> TYPE: DNA
<213> ORGANISM: influenza A virus

<400> SEQUENCE: 7

```
ttgaatggat gtcaatccga ccctactttt cctaaaagtt ccagcgcaaa atgccataag     60
caccacattc ccttatactg gagatcctcc atacagccat ggaacaggaa caggatacac    120
catggacaca gtcaacagaa cacatcaata ttcagaaaaa gggaagtgga cgacaaacac    180
tgagactggg gcaccccaac tcaatccaat tgatggacca ctacctgagg ataatgaacc    240
aagtgggtat gcacagacag actgtgttct agaggccatg gctttccttg aagaatccca    300
cccagggata tttgagaatt catgccttga aacaatggaa gttgttcaac aaacaagggt    360
ggataaacta actcaaggtc gccagactta tgattggaca ttaaacagaa atcaaccagc    420
agcaactgca ttggccaaca ccatagaagt ttttaggtcg aatagtctaa cagccaatga    480
gtcaggaaga ctaataaatt tcctaaagga tgtaatggaa tcaatggata gagaagaagt    540
ggagataaca acacactttc gaagaaaaag gagagtgaga gacaacatga ccaagaagat    600
ggtcacacaa agaacaatag gaaagaaaaa acaaagattg agtaagagaa gttatctaat    660
aagagcactt acattgaata cgatgaccaa agatgcagag agaggcaaat taaaaagaag    720
ggctatcgca acacccggga tgcaaattag agggttcgtg tactttgttg agactttagc    780
taggagcatt tgcgaaaagc ttgaacagtc tggactccca gtagggggaa atgaaaagaa    840
ggccaaattg gcaaatgttg tgagaaaaat gatgactaat tcacaagaca cagagctttc    900
tttcacaatc actggggaca atactaagtg gaatgaaaat caaaatcctc gaatgttcct    960
ggcgatgatt acatatatca cccgaaatca acccgagtgg ttcagaaaca tcctgagcat   1020
ggcacccata atgttttcaa acaaaatggc aagactagga aaagggtaca tgttcgagag   1080
taaaaggatg aagctccgaa cacaaatacc agcagaaatg ctagcaagca ttgatctgaa   1140
gtatttcaat gaatcaacaa ggaagaaaat tgagaaaata aggcctcttc taatagatgg   1200
cacagcatca ttgagccctg gaatgatgat gggcatgttc aacatgctaa gtacggtttt   1260
gggagtctcg atactgaatc ttggacaaaa gaaatacacc aggacaacat actggtggga   1320
tgggctccaa tcctccgacg attttgccct cattgtgaat gcaccaaatt atgagggaat   1380
acaagcagga gtgaatagat tctacaggac ctgcaagtta gtaggaataa acatgagcaa   1440
aaagaagtcc tatataaata aaacagggac atttgaattc acaagctttt tttatcgcta   1500
tgggtttgtg gctaatttta gcatggagct gcccagtttt ggagtgtctg gaataaatga   1560
atcagctgat atgagtattg gagtaacagt gataaagaac aatatgataa acaatgatct   1620
tggacctgca acagcccaga tggcccttca attgttcatc aaagactaca gatacacata   1680
taggtgccac agaggagaca cacaaattca gacgagaaga tcattcgagc taaagaagct   1740
atgggatcaa acccgatcaa atgcaggact attagtatct gatggaggac caaacttata   1800
caatatcagg aatcttcaca ttcctgaagt ctgcttaaaa tgggagctaa tggatgagga   1860
ttatcgggga aggctttgta atcccctgaa tccttttgtc agccataaag agattgattc   1920
tgtaaacaat gctgtggtga tgccagccca tggcccagcc aaaagcatgg aatatgatgc   1980
cgttgcaact acacactcct ggatccccaa gaggaatcgc tctattctca acacaagcca   2040
aaggggaatt cttgaggatg aacagatgta ccagaagtgc tgcaacctgt tcgagaaatt   2100
tttccctagt agttcataca ggagaccggt tggaatttct agcatggtgg aggccatggt   2160
```

-continued

| | |
|---|---|
| gtctagggcc cggattgatg ccagaatcga cttcgagtct ggacggatta agaaagaaga | 2220 |
| gttctctgag atcataagga tctgttccac cattgaagaa ctcagacggc aaacatgatg | 2280 |
| aatttggctt gtccttcatg aaaaaatgcc ttgtttctac taatacgaga cgatataaa | 2339 |

<210> SEQ ID NO 8
<211> LENGTH: 2299
<212> TYPE: DNA
<213> ORGANISM: influenza A virus

<400> SEQUENCE: 8

| | |
|---|---|
| tatattcaat atggagagaa taaaagaact aagagaccta atgtcgcagt cccgcactcg | 60 |
| cgaaatactc accaagacca ctgtggacca tatggccata atcaaaaagt acacatcggg | 120 |
| aaggcaagag aagaaccctg cactcagaat gaagtggatg atggcaatga agtacccaat | 180 |
| cacagcagac aagagaataa tggacatgat tccagagaga atgaacaag acaaacccct | 240 |
| ctggagcaaa acaaacgatg ctggatcgga ccgcgtgatg gtatcacccc tggctgtaac | 300 |
| atggtggaat aggaatggcc aacagcaag cacagttcac taccctaagg tatataaaac | 360 |
| ttatttcgaa aaagtcgaaa ggttaaaaca tggtaccttt ggccctgtcc acttcaggaa | 420 |
| tcaagttaaa ataagaagga gagttgacac aaaccctggt cacgcagatc tcagagccaa | 480 |
| ggaggcacag gatgtgatca tggaagttgt tttcccaaat gaagtggggg caagaatact | 540 |
| gacatcagag tcacagctga caataacaaa agagaagaaa gaagagctcc aggattgtaa | 600 |
| aattgctccc ttaatggtgg catacatgct agaaaaagag ttggtccgta aaacgaggtt | 660 |
| tctcccggtg gctggtggaa caggcagtgt ttatattgaa gtgctgcatt taactcaggg | 720 |
| gacatgctgg gagcaaatgt acactccagg aggagaagtg agaaatgatg atgttgacca | 780 |
| aagtttgatt attgctgcta gaaacatagt aagaagagca gcagtgtcag cagacccatt | 840 |
| agcatctctt ttggaaatgt gccacagcac acagattgga ggaataagga tggtggacat | 900 |
| ccttagacag aatccaacgg aggaacaagc cgtagacata tgcaaggcag caatgggct | 960 |
| gaggattagc tcctctttca gctttggtgg gttcactttc aaaagaacaa gtgggtcatc | 1020 |
| agttaagaga gaagaagaag tgctcacggg caaccttcaa acactgaaaa taagagtaca | 1080 |
| tgaaggatat gaagaattca caatggtcgg gagaagagca acagctattc tcagaaaagc | 1140 |
| aaccaggaga ttgatccagt tgatagtaag tgggagagac gagcagtcaa ttgctgaggc | 1200 |
| aataattgtg gccatggtat tttcacaaga ggactgcatg atcaaggcag ttaggggcga | 1260 |
| tctgaacttt gtcaataggg caaaccagcg actgaatccc atgcatcaac tcttgaggca | 1320 |
| tttccaaaaa gatgcaaaag tgcttttcca gaattgggga attgaaccca tcgacaatgt | 1380 |
| gatgggaatg atcgggatat gcccgatat gaccccaagc acgagatgt cgctgagagg | 1440 |
| gataagagtc agcaaaatgg gagtagatga atactccagc acggagagag tggtagtgag | 1500 |
| cattgacaga ttttttgagg gttcgggatca acgagggaac gtactattgt ctcctgaaga | 1560 |
| ggtcagtgag acacaaggga cggagaaatt ggcaataact tattcgtcat cgatgatgtg | 1620 |
| ggagatcagt ggccctgagt cagtgctggt caacacttat caatggatca taggaattg | 1680 |
| ggaaagtttg aaaattcaat ggtcacaaga tcccacgatg ttatacaaca aaatggaatt | 1740 |
| tgaaccattt cagtctcttg tccctaaagc aaccagaagt cgttacagtg ggttcgtgag | 1800 |
| gacactgttc cagcaaatgc gggatgtgat tggaacattt gacactgtcc aaataataaa | 1860 |
| acttctcccc tttgctgctg ctccaccaga acagagtagg atgcagtttt cctcactgac | 1920 |
| tgtgaatgtg agaggatcag ggttgaggat actggtaaga ggcaattctc cagtattcaa | 1980 |

-continued

```
ttacaataaa gcaaccaaaa ggcttacagt tcttggaaag gatgcaggtg aattgaccga    2040
agacccagat gaaggcacag ctggagtgga gtctgctgtc ctgagggat ttctcatttt     2100 gggcaaagaa gacaagagat atggtccagc attaagcatc aatgaactga gcaatcttgc    2160
aaaaggagag aaagctaatg tgctaattgg gcaaggagac gtagtgttgg taatgaaacg    2220
gaaacgggac tctagcatac ttactgacag ccagacagcg accaaaagaa ttcggatggc    2280
catcaattag tgtcgaatt                                                 2299
```

<210> SEQ ID NO 9
<211> LENGTH: 562
<212> TYPE: PRT
<213> ORGANISM: influenza A virus

<400> SEQUENCE: 9

```
Met Thr Ile Thr Phe Leu Ile Leu Leu Phe Thr Val Val Lys Gly Asp
  1               5                  10                  15

Gln Ile Cys Ile Gly Tyr His Ala Asn Asn Ser Thr Glu Lys Val Asp
             20                  25                  30

Thr Ile Leu Glu Arg Asn Val Thr Val Thr His Ala Lys Asn Ile Leu
         35                  40                  45

Glu Lys Thr His Asn Gly Lys Leu Cys Arg Leu Ser Gly Ile Pro Pro
     50                  55                  60

Leu Glu Leu Gly Asp Cys Ser Ile Ala Gly Trp Leu Leu Gly Asn Pro
 65                  70                  75                  80

Glu Cys Asp Arg Leu Leu Ser Val Pro Glu Trp Ser Tyr Ile Val Glu
                 85                  90                  95

Lys Glu Asn Pro Val Asn Gly Leu Cys Tyr Pro Gly Ser Phe Asn Asp
            100                 105                 110

Tyr Glu Glu Leu Lys His Leu Leu Thr Ser Val Thr His Phe Glu Lys
        115                 120                 125

Val Lys Ile Leu Pro Arg Asp Gln Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Ile Ala Lys Arg
                165                 170                 175

Ser Tyr Asn Asn Thr Ser Gly Glu Gln Met Leu Val Ile Trp Gly Ile
            180                 185                 190

His His Pro Asn Asp Asp Ala Glu Gln Arg Thr Leu Tyr Gln Asn Val
        195                 200                 205

Gly Thr Tyr Val Ser Val Gly Thr Ser Thr Leu Asn Lys Arg Ser Ile
    210                 215                 220

Pro Glu Ile Ala Thr Arg Pro Lys Val Asn Gly Leu Gly Gly Arg Met
225                 230                 235                 240

Glu Phe Ser Trp Thr Leu Leu Glu Thr Trp Asp Val Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Lys Ile Leu Glu Asn Cys
        275                 280                 285

Glu Thr Lys Cys Gln Thr Pro Leu Gly Ala Ile Asn Thr Thr Leu Pro
    290                 295                 300

Phe His Asn Ile His Pro Leu Thr Ile Gly Glu Cys Pro Lys Tyr Val
305                 310                 315                 320
```

```
Lys Ser Asp Arg Leu Ile Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Ile Asp Gly Ile Thr Asn Lys Val Asn Ser Val Ile Glu Lys Met Asn
385                 390                 395                 400

Thr Gln Phe Glu Ala Val Gly Lys Glu Phe Asn Asn Leu Glu Arg Arg
                405                 410                 415

Leu Glu Asn Leu Asn Lys Lys Met Glu Asp Gly Phe Ile Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Ala Lys Glu Ile Gly Asn Gly Cys Phe Glu Phe
465                 470                 475                 480

Tyr His Lys Cys Asp Asp Glu Cys Met Asn Ser Val Arg Asn Gly Thr
                485                 490                 495

Tyr Asp Tyr Ile Lys Tyr Glu Glu Ser Lys Leu Asn Arg Asn Glu
            500                 505                 510

Ile Lys Gly Val Lys Leu Ser Asn Met Gly Val Tyr Gln Ile Leu Ala
        515                 520                 525

Ile Tyr Ala Thr Val Ala Gly Ser Leu Ser Leu Ala Ile Met Ile Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 10
<211> LENGTH: 252
<212> TYPE: PRT
<213> ORGANISM: influenza A virus

<400> SEQUENCE: 10

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Thr Val Thr Thr Glu Val Ala Phe
```

-continued

```
            130                 135                 140
Gly Leu Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Ile Ala Ser Thr Ala Lys Ala Met Glu Gln Met
                180                 185                 190

Ala Gly Ser Ser Glu Gln Ala Ala Glu Ala Met Glu Val Ala Ser Gln
                195                 200                 205

Ala Arg Gln Met Val Gln Ala Met Arg Thr Ile Gly Thr His Pro Ser
                210                 215                 220

Ser Ser Thr Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 11
<211> LENGTH: 469
<212> TYPE: PRT
<213> ORGANISM: influenza A virus

<400> SEQUENCE: 11

Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Val Phe Asn
                20                  25                  30

Thr Val Ile His Glu Lys Ile Gly Asp His Gln Ile Val Thr Tyr Pro
                35                  40                  45

Ile Ile Thr Thr Pro Ala Val Pro Asn Cys Ser Asp Thr Ile Ile Thr
                50                  55                  60

Tyr Asn Asn Thr Val Ile Asn Asn Ile Thr Thr Thr Ile Ile Thr Glu
65                  70                  75                  80

Glu Glu Arg Pro Phe Lys Ser Pro Leu Pro Leu Cys Pro Phe Arg Gly
                85                  90                  95

Phe Phe Pro Phe His Lys Asp Asn Ala Ile Arg Leu Gly Glu Asn Lys
                100                 105                 110

Asp Val Ile Val Thr Arg Glu Pro Tyr Val Ser Cys Asp Asn Asp Asn
                115                 120                 125

Cys Trp Ser Phe Ala Leu Ala Gln Gly Ala Leu Leu Gly Thr Lys His
                130                 135                 140

Ser Asn Gly Thr Ile Lys Asp Arg Thr Pro Tyr Arg Ser Leu Ile Arg
145                 150                 155                 160

Phe Pro Ile Gly Thr Ala Pro Val Leu Gly Asn Tyr Lys Glu Ile Cys
                165                 170                 175

Ile Ala Trp Ser Ser Ser Ser Cys Phe Asp Gly Lys Glu Trp Met His
                180                 185                 190

Val Cys Met Thr Gly Asn Asp Asn Ala Ser Ala Gln Ile Ile Tyr
                195                 200                 205

Gly Gly Arg Met Thr Asp Ser Ile Lys Ser Trp Arg Lys Asp Ile Leu
                210                 215                 220

Arg Thr Gln Glu Ser Glu Cys Gln Cys Ile Asp Gly Thr Cys Val Val
225                 230                 235                 240

Ala Val Thr Asp Gly Pro Ala Ala Asn Ser Ala Asp Tyr Arg Val Tyr
                245                 250                 255

Trp Ile Arg Glu Gly Lys Ile Ile Lys Tyr Glu Asn Val Pro Lys Thr
```

```
              260                 265                 270
Lys Ile Gln His Leu Glu Glu Cys Ser Cys Tyr Val Asp Ile Asp Val
            275                 280                 285

Tyr Cys Ile Cys Arg Asp Asn Trp Lys Gly Ser Asn Arg Pro Trp Met
        290                 295                 300

Arg Ile Asn Asn Glu Thr Ile Leu Glu Thr Gly Tyr Val Cys Ser Lys
305                 310                 315                 320

Phe His Ser Asp Thr Pro Arg Pro Ala Asp Pro Ser Thr Met Ser Cys
                325                 330                 335

Asp Ser Pro Ser Asn Val Asn Gly Gly Pro Gly Val Lys Gly Phe Gly
            340                 345                 350

Phe Lys Ala Gly Asp Asp Val Trp Leu Gly Arg Thr Val Ser Thr Ser
        355                 360                 365

Gly Arg Ser Gly Phe Glu Ile Ile Lys Val Thr Glu Gly Trp Ile Asn
    370                 375                 380

Ser Pro Asn His Val Lys Ser Ile Thr Gln Thr Leu Val Ser Asn Asn
385                 390                 395                 400

Asp Trp Ser Gly Tyr Ser Gly Ser Phe Ile Val Lys Ala Lys Asp Cys
                405                 410                 415

Phe Gln Pro Cys Phe Tyr Val Glu Leu Ile Arg Gly Arg Pro Asn Lys
            420                 425                 430

Asn Asp Asp Val Ser Trp Thr Ser Asn Ser Ile Val Thr Phe Cys Gly
        435                 440                 445

Leu Asp Asn Glu Pro Gly Ser Gly Asn Trp Pro Asp Gly Ser Asn Ile
    450                 455                 460

Gly Phe Met Pro Lys
465

<210> SEQ ID NO 12
<211> LENGTH: 498
<212> TYPE: PRT
<213> ORGANISM: influenza A virus

<400> SEQUENCE: 12

Met Ala Ser Gln Gly Thr Lys Arg Ser Tyr Glu Gln Met Glu Thr Gly
1               5                   10                  15

Gly Glu Arg Gln Asp Ala Thr Glu Ile Arg Ala Ser Val Gly Arg Met
            20                  25                  30

Ile Gly Gly Ile Gly Lys Phe Tyr Ile Gln Met Cys Thr Glu Leu Lys
        35                  40                  45

Leu Ser Asp Tyr Glu Gly Arg Leu Ile Gln Asn Ser Met Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Ile Leu Tyr Asp
            100                 105                 110

Lys Glu Glu Ile Arg Arg Val Trp Arg Gln Ala Asn Asn Gly Glu Asp
        115                 120                 125

Ala Thr Ala Gly Leu Ala His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
```

```
                    165                 170                 175
Gly Ala Ala Gly Ala Ala Val Lys Gly Val Gly Thr Ile Ala Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
        210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
        290                 295                 300

Lys Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Lys Lys Val
            340                 345                 350

Ile Pro Arg Gly Arg Leu Ser Thr Arg Gly Val Gln Ile Ala Ser Asn
        355                 360                 365

Glu Asn Val Glu Ala Met Asp Ser Asn Thr Leu Glu Leu Arg Ser Arg
        370                 375                 380

Tyr Trp Ala Ile Arg Thr Arg Ser Gly Gly Asn Thr Asn Gln Gln Lys
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Val Met Ala Ala Phe Ser Gly Asn
            420                 425                 430

Asn Glu Gly Arg Thr Ser Asp Met Arg Thr Glu Val Ile Arg Met Met
        435                 440                 445

Glu Asn Ala Lys Pro Glu Asp Leu Ser Phe Gln Gly Arg Gly Val Phe
        450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Ser

<210> SEQ ID NO 13
<211> LENGTH: 219
<212> TYPE: PRT
<213> ORGANISM: influenza A virus

<400> SEQUENCE: 13

Met Asp Ser Thr Thr Val Ser Ser Phe Gln Val Asp Cys Phe Leu Trp
1               5                   10                  15

His Ile Arg Lys Arg Phe Ala Asp Asn Gly Leu Gly Asp Ala Pro Phe
            20                  25                  30

Leu Asp Arg Leu Arg Arg Asp Gln Lys Ser Leu Lys Gly Arg Gly Asn
        35                  40                  45
```

```
Thr Leu Gly Leu Asp Ile Glu Thr Ala Thr Leu Val Gly Lys Gln Ile
        50                  55                  60

Val Glu Trp Ile Leu Lys Glu Ser Ser Asp Thr Leu Lys Met Thr
 65                  70                  75                  80

Ile Ala Ser Val Pro Thr Ser Arg Tyr Leu Ala Asp Met Thr Leu Glu
                 85                  90                  95

Glu Met Ser Arg Asp Trp Leu Met Leu Met Pro Arg Gln Lys Ile Ile
            100                 105                 110

Gly Pro Leu Cys Val Arg Met Asp Gln Ala Ile Met Glu Lys Asn Ile
            115                 120                 125

Ile Leu Lys Ala Asn Phe Ser Val Ile Phe Asn Arg Leu Glu Thr Leu
130                 135                 140

Ile Leu Leu Arg Ala Phe Thr Glu Glu Gly Thr Ile Val Gly Glu Ile
145                 150                 155                 160

Ser Gln Leu Pro Ser Leu Pro Gly His Thr Asn Glu Asp Val Lys Asn
                165                 170                 175

Ala Ile Gly Val Leu Ile Gly Gly Leu Glu Trp Asn Gly Asn Thr Val
            180                 185                 190

Arg Gly Ser Glu Asn Leu Gln Arg Phe Ala Trp Arg Asn Arg Asn Glu
            195                 200                 205

Asp Gly Arg Pro Ser Leu Pro Pro Glu Lys Lys
210                 215

<210> SEQ ID NO 14
<211> LENGTH: 716
<212> TYPE: PRT
<213> ORGANISM: influenza A virus

<400> SEQUENCE: 14

Met Glu Asp Phe Val Arg Gln Cys Phe Asn Pro Met Ile Val Glu Leu
 1               5                  10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
 50                  55                  60

Ser Gly Asp Pro Asn Ala Leu Leu Lys His Arg Phe Glu Ile Ile Glu
 65                  70                  75                  80

Gly Arg Asp Arg Thr Met Ala Trp Thr Val Val Asn Ser Ile Cys Asn
                 85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Lys Thr His
130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
            195                 200                 205
```

```
Gly Thr Met Arg Arg Leu Ala Asp Gln Ser Leu Pro Pro Asn Phe Ser
    210                 215                 220
Ser Leu Glu Asn Phe Arg Ala Tyr Val Asp Gly Phe Glu Pro Asn Gly
225                 230                 235                 240
Cys Ile Glu Gly Lys Leu Ser Gln Met Ser Lys Glu Val Asn Ala Arg
                245                 250                 255
Ile Glu Pro Phe Leu Lys Thr Thr Pro Arg Pro Leu Lys Leu Pro Asp
            260                 265                 270
Gly Pro Pro Cys Ser Gln Arg Ser Lys Phe Leu Leu Met Asp Ala Leu
        275                 280                 285
Lys Leu Ser Ile Glu Asp Pro Ser His Glu Gly Glu Gly Ile Pro Leu
    290                 295                 300
Tyr Asp Ala Ile Lys Cys Met Lys Thr Phe Phe Gly Trp Lys Glu Pro
305                 310                 315                 320
Asn Ile Ile Lys Pro His Glu Lys Gly Ile Asn Pro Asn Tyr Phe Leu
                325                 330                 335
Ala Trp Lys Gln Val Leu Ala Glu Leu Gln Asp Leu Glu Asn Glu Glu
            340                 345                 350
Lys Ile Pro Lys Thr Lys Asn Met Lys Lys Thr Ser Gln Leu Lys Trp
        355                 360                 365
Ala Leu Gly Glu Asn Met Ala Pro Glu Lys Val Asp Phe Glu Asp Cys
    370                 375                 380
Lys Asp Ile Gly Asp Leu Lys Gln Tyr Asp Ser Asp Glu Pro Glu Pro
385                 390                 395                 400
Arg Ser Leu Ala Ser Trp Ile Gln Ser Glu Phe Asn Lys Ala Cys Glu
                405                 410                 415
Leu Thr Asp Ser Ser Trp Ile Glu Leu Asp Glu Ile Gly Glu Asp Val
            420                 425                 430
Ala Pro Ile Glu His Ile Ala Ser Met Arg Arg Asn Tyr Phe Thr Ala
        435                 440                 445
Glu Val Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Leu Glu Pro His Lys Trp Glu Lys Tyr Cys Val Leu Glu
    530                 535                 540
Ile Gly Asp Met Leu Leu Arg Thr Ala Ile Gly Gln Val Ser Arg Pro
545                 550                 555                 560
Met Phe Leu Tyr Ile Arg Thr Asn Gly Thr Ser Lys Ile Lys Met Lys
                565                 570                 575
Trp Gly Met Glu Met Arg Arg Cys Leu Leu Gln Ser Leu Gln Gln Ile
            580                 585                 590
Glu Ser Met Ile Glu Ala Glu Ser Ser Val Lys Glu Lys Asp Met Thr
        595                 600                 605
Lys Glu Phe Phe Glu Asn Lys Ser Glu Thr Trp Pro Ile Gly Glu Ser
    610                 615                 620
Pro Arg Gly Val Glu Glu Gly Ser Ile Gly Lys Val Cys Arg Thr Leu
```

```
                        625                 630                 635                 640
Leu Ala Lys Ser Val Phe Asn Ser Leu Tyr Ala Ser Pro Gln Leu Glu
                        645                 650                 655

Gly Phe Ser Ala Glu Ser Arg Lys Leu Leu Ile Val Gln Ala Leu
                    660                 665                 670

Arg Asp Asn Leu Glu Pro Gly Thr Phe Asp Leu Gly Gly Leu Tyr Glu
                    675                 680                 685

Ala Ile Glu Glu Cys Leu Ile Asn Asp Pro Trp Val Leu Leu Asn Ala
                    690                 695                 700

Ser Trp Phe Asn Ser Phe Leu Thr His Ala Leu Lys
705                 710                 715

<210> SEQ ID NO 15
<211> LENGTH: 757
<212> TYPE: PRT
<213> ORGANISM: influenza A virus

<400> SEQUENCE: 15

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Ser Leu Thr Ala Asn Glu Ser
145                 150                 155                 160

Gly Arg Leu Ile Asn Phe Leu Lys Asp Val Met Glu Ser Met Asp Arg
                165                 170                 175

Glu Glu Val Glu Ile Thr Thr His Phe Arg Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Ser Lys Arg Ser Tyr Leu Ile Arg Ala Leu Thr Leu
210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
```

-continued

```
            290                 295                 300
Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
                340                 345                 350

Lys Gly Tyr Met Phe Glu Ser Lys Arg Met Lys Leu Arg Thr Gln Ile
                355                 360                 365

Pro Ala Glu Met Leu Ala Ser Ile Asp Leu Lys Tyr Phe Asn Glu Ser
            370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                    405                 410                 415

Thr Val Leu Gly Val Ser Ile Leu Asn Leu Gly Gln Lys Lys Tyr Thr
                420                 425                 430

Arg Thr Thr Tyr Trp Trp Asp Gly Leu Gln Ser Ser Asp Asp Phe Ala
            435                 440                 445

Leu Ile Val Asn Ala Pro Asn Tyr Glu Gly Ile Gln Ala Gly Val Asn
        450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                    485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Arg Ser Asn Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Arg Gly Arg Leu
        610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
                    645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720
```

```
Arg Ala Arg Ile Asp Ala Arg Ile Asp Phe Glu Ser Gly Arg Ile Lys
                725                 730                 735

Lys Glu Glu Phe Ser Glu Ile Ile Arg Ile Cys Ser Thr Ile Glu Glu
            740                 745                 750

Leu Arg Arg Gln Thr
        755
```

<210> SEQ ID NO 16
<211> LENGTH: 759
<212> TYPE: PRT
<213> ORGANISM: influenza A virus

<400> SEQUENCE: 16

```
Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Asp Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Ala Ser Thr Val His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Thr Asn Pro Gly His Ala Asp Leu Arg Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Lys Glu Leu Val Arg Lys Thr Arg Phe Leu Pro Val Ala Gly Gly Thr
    210                 215                 220

Gly Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335
```

-continued

```
Ser Val Lys Arg Glu Glu Val Leu Thr Gly Asn Leu Gln Thr Leu
            340                 345                 350

Lys Ile Arg Val His Glu Gly Tyr Glu Glu Phe Thr Met Val Gly Arg
            355                 360                 365

Arg Ala Thr Ala Ile Leu Arg Lys Ala Thr Arg Leu Ile Gln Leu
            370                 375                 380

Ile Val Ser Gly Arg Asp Glu Gln Ser Ile Ala Glu Ala Ile Val
385                 390                 395                 400

Ala Met Val Phe Ser Gln Glu Asp Cys Met Ile Lys Ala Val Arg Gly
                    405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
            435                 440                 445

Trp Gly Ile Glu Pro Ile Asp Asn Val Met Gly Met Ile Gly Ile Leu
            450                 455                 460

Pro Asp Met Thr Pro Ser Thr Glu Met Ser Leu Arg Gly Ile Arg Val
465                 470                 475                 480

Ser Lys Met Gly Val Asp Glu Tyr Ser Ser Thr Glu Arg Val Val Val
                    485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Ala
            515                 520                 525

Ile Thr Tyr Ser Ser Ser Met Met Trp Glu Ile Ser Gly Pro Glu Ser
            530                 535                 540

Val Leu Val Asn Thr Tyr Gln Trp Ile Ile Arg Asn Trp Glu Ser Leu
545                 550                 555                 560

Lys Ile Gln Trp Ser Gln Asp Pro Thr Met Leu Tyr Asn Lys Met Glu
                    565                 570                 575

Phe Glu Pro Phe Gln Ser Leu Val Pro Lys Ala Thr Arg Ser Arg Tyr
            580                 585                 590

Ser Gly Phe Val Arg Thr Leu Phe Gln Gln Met Arg Asp Val Ile Gly
            595                 600                 605

Thr Phe Asp Thr Val Gln Ile Ile Lys Leu Leu Pro Phe Ala Ala Ala
610                 615                 620

Pro Pro Glu Gln Ser Arg Met Gln Phe Ser Ser Leu Thr Val Asn Val
625                 630                 635                 640

Arg Gly Ser Gly Leu Arg Ile Leu Val Arg Gly Asn Ser Pro Val Phe
                    645                 650                 655

Asn Tyr Asn Lys Ala Thr Lys Arg Leu Thr Val Leu Gly Lys Asp Ala
            660                 665                 670

Gly Glu Leu Thr Glu Asp Pro Asp Glu Gly Thr Ala Gly Val Glu Ser
            675                 680                 685

Ala Val Leu Arg Gly Phe Leu Ile Leu Gly Lys Glu Asp Lys Arg Tyr
            690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                    725                 730                 735

Arg Lys Arg Asp Ser Ser Ile Leu Thr Asp Ser Gln Thr Ala Thr Lys
            740                 745                 750

Arg Ile Arg Met Ala Ile Asn
            755
```

<210> SEQ ID NO 17
<211> LENGTH: 1780
<212> TYPE: DNA
<213> ORGANISM: influenza A virus

<400> SEQUENCE: 17

```
ttattcgtct tcaaggagca aaagcagggg ttataccata gacaaccgaa caaagacaat      60
gaccatcact tttctcatcc tcctgttcac agtagtgaaa ggggaccaaa tatgcatcgg     120
ataccatgcc aacaattcca cagaaaaagt tgacacaatc ttggaacgaa acgtcaccgt     180
gactcatgcc aagaacattc ttgaaaagac gcataatgga aagttgtgca gattgagtgg     240
aatccctcca ttggaactgg gggattgcag cattgcaggt tggctccttg gaaatccgga     300
atgtgaccgg ctcttaagtg tacctgaatg gtcctatata gtggaaaagg aaaacccggt     360
gaatggtctg tgctatccag gcagtttcaa tgattatgag gaattgaaac atcttctcac     420
cagtgtgaca cactttgaga aagttaagat tctgcccaga gatcaatgga cccagcacac     480
aacaactggt ggttctcggg cctgtgcagt atctggaaac ccgtcattct ttaggaacat     540
ggtttggctt acaaagaaag ggtcaaacta ctcaattgct aaaaggtcat acaacaacac     600
aagtggggag caaatgctgg taatatgggg gatacatcac cccaatgacg atgcggaaca     660
gaggacactg taccagaatg tgggaacata tgtttccgtt ggaacatcaa cactaaataa     720
gaggtcaatc cctgaaatag caacaaggcc caaagtcaat ggactgggag gaagaatgga     780
attctcttgg actctattgg agacatggga tgtcataaat tttgagagca ctggtaattt     840
aattgcacca gaatacggat tcaaaatatc aaagagagga agctcaggaa ttatgaagac     900
agagaaaata cttgaaaatt gtgaaaccaa atgtcagacc cccttggggg caataaatac     960
aacattgccc tttcacaaca ttcacccatt gacaataggt gagtgcccca agtatgtaaa    1020
gtcagataga ctgattttgg cgacaggagt aagaaatgtc ccccagattg aatcaagggg    1080
attgtttgga gcaatagctg ggtttataga aggcggatgg caagggatgg ttgatggctg    1140
gtatgggtac catcacagca atgatcaagg atcaggatat gcagcagaca aagaatccac    1200
tcaaaaggca attgatggga taactaacaa agtaaattct gtgattgaaa agatgaacac    1260
tcagtttgag gctgttggga aagagttcaa caacctagag agaaggctgg aaaacttaaa    1320
taaaaagatg gaagatggat ttattgatgt atggacatat aatgccgaac tcctagttct    1380
aatggaaaat gagaggacac ttgatttcca tgattctaat gtgaagaatc tgtacgataa    1440
ggtcagaatg caattgagag acaatgctaa ggaaataggg aacggatgct ttgagtttta    1500
tcataaatgt gatgatgaat gcatgaatag tgtcaggaat gggacatatg attatcccaa    1560
atatgaggaa gagtccaagc tgaacaggaa cgaaatcaaa ggagtgaaat tgagcaatat    1620
gggggtttat caaatacttg ctatatacgc tacagttgca ggctctttgt cactggcaat    1680
catgatagct gggatttctt tctggatgtg ttctaatggg tctctgcaat gcagaatttg    1740
catatgactg taagtcaatt tgtaattaaa aaaactcctt                          1780
```

<210> SEQ ID NO 18
<211> LENGTH: 991
<212> TYPE: DNA
<213> ORGANISM: influenza A virus

<400> SEQUENCE: 18

```
gtttaaagat gagtcttcta accgaggtcg aaacgtatgt tctctctatc gtcccgtcag      60
gccccctcaa agccgagata gcacagagac tcgaagacgt tttgcagggg aaaaacaccg     120
```

```
atcttgaggc tctcatggaa tggctaaaga caagaccaat cctgtcacct ctgactaagg      180
ggattttagg gtttgtgttc acgctcaccg tgcccagtga gcgaggactg cagcgtagac      240
gttttgttca gaatgccctc aatgggaatg gtgacccgaa caacatggac aaggcggtca      300
aactttacag gaaactaaaa agggaaataa cattccatgg ggccaaagaa gtagcgctca      360
gttactctgc tggtgcactt gccagttgca tgggcctcat atacaacaga tgggaactg       420
tcaccactga ggttgccttt ggtctggtat gcgcaacctg tgaacagatt gctgattctc      480
agcatcgatc ccatagacaa atggtgacaa caaccaatcc actaatcagg cacgagaaca      540
gaatggtgat agccagcaca acagctaaag caatggaaca aatggctgga tcaagcgaac      600
aagcagcaga ggctatggag gttgccagcc aggctagaca aatggtacag gcaatgagaa      660
caattgggac tcaccctagt tccagcactg gtctaaaaga tgatcttctt gaaaatttac      720
aggcctatca gaaacggatg ggagtgcaaa tgcaacgatt caaatgatcc tctcactgat      780
gctgcaagca tcattgggat tttgcacctg atattgtgga ttcttgatcg tctttttttc      840
aaatgcattt accgtcgctt taaatacggt ctgcaaagag ggccttctac ggaaggagtg      900
ccggagtcca tgagggaaga atatcgacag aaacagcaga gtgctgtgga tgttgacgat      960
ggtcattttg tcaacatagt gctagagtaa a                                    991
```

<210> SEQ ID NO 19
<211> LENGTH: 1438
<212> TYPE: DNA
<213> ORGANISM: influenza A virus

<400> SEQUENCE: 19

```
agatgaatcc gaatcagaag ataataacaa tcggggtagt gaataccact ctgtcaacaa       60
tagcccttct cattggagtg ggaaacttaa ttttcaacac agtcatacat gagaaaatag      120
gagaccatca aatagtgacc tatccaacaa taacgacccc tgcagtaccg aactgcagtg      180
acactataat aacatacaat aacactgtga taaacaacat aacaacaaca ataataactg      240
aagaagaaag gcctttcaag tctccactac cgctgtgccc cttcagagga ttcttccctt      300
ttcacaagga caatgcaata cgactgggtg aaaacaaaga cgtcatagtc acaagagagc      360
cttatgttag ctgcgataat gacaactgct ggtcctttgc tctcacacaa ggagcattgc      420
tagggaccaa acatagcaat gggaccatta agacaggac accatatagg tctctaattc      480
gtttcccaat aggaacagct ccagtactag gaaattataa agagatatgc attgcttggt      540
cgagcagcag ttgctttgac gggaaagagt ggatgcatgt gtgcatgaca gggaacgata      600
atgatgcaag tgcccagata atatatgag ggagaatgac agactccatt aaatcatgga      660
gaaaggacat actaagaact caggagtctg aatgccaatg cattgacggg acttgtgttg      720
ttgctgtcac agatgccct gctgctaata gtgcagatta cagggttac tggatacggg      780
agggaaaaat aataaagtat gaaaatgttc ccaaaacaaa gatacaacac ttagaagaat      840
gttcctgcta tgtggacatt gatgtttact gtatatgtag ggacaattgg aagggctcta      900
acaaccttg gatgagaatc aacaacgaga ctatactgga acagggtat gtatgtagta      960
aattccactc agacaccccc aggcccgctg acccttcaac aatgtcatgt gactccccaa     1020
gcaatgtcaa tggaggaccc ggagtgaagg ggtttggttt caaagctggc gatgatgtat     1080
ggttaggtag aacagtgtcg actagtggta gatcgggctt tgaaattatc aaagttacag     1140
aagggtggat caactctcct aaccatgtca aatcaattac acaaacacta gtgtcaaaca     1200
atgactggtc aggctattcc ggtagcttca ttgtcaaagc caaggactgt tttcagccct     1260
```

```
gtttttatgt tgagcttata cgagggaggc ccaacaagaa tgatgacgtc tcttggacaa    1320
gtaatagtat agttactttc tgtggactag acaatgaacc tggatcggga aattggccag    1380
atggttctaa cattgggttt atgcccaagt aatagaaaaa agcaccttgt ttctacta      1438

<210> SEQ ID NO 20
<211> LENGTH: 1536
<212> TYPE: DNA
<213> ORGANISM: influenza A virus

<400> SEQUENCE: 20
gataatcact caatgagtga catcgaagcc atggcgtctc aaggcaccaa acgatcatat      60
gaacaaatgg agactggtgg ggaacgccag gatgccacag aaatcagagc atctgtcgga    120
agaatgattg gtggaatcgg gaaattctac atccaaatgt gcactgaact caaactcagt    180
gactatgagg gacgactaat ccaaaatagc atgacaatag agagaatggt gctctctgct    240
tttgatgaga aagaaataa ataccctagaa gagcatccca gtgcagggaa ggatcctaag    300
aaaactggag acccatata tagaagagta gacggaaagt ggatgagaga actcattctt    360
tatgacaaag aagaataag gagagtttgg cgccaagcaa caatggtga agatgcaaca    420 gctggtcttg ctcatatcat gatttggcac tccaatctga atgatgccac gtaccagaga    480
acaagagcgc ttgttcgcac cggaatggat cccagaatgt gctctctaat gcaaggttca    540
acacttccca aaggtctggg ggccgcaggt gctgcagtga aggagttgg aacagtagca    600 atggaattaa tcagaatgat caaacgtggg atcaatgacc gaaacttctg gagaggtgaa    660
aatggacgaa agacaaggat tgcatatgaa agaatgtgca atattctcaa gggaaaattt    720
cagacagctg cccagagggc aatgatggat caagtgagag aaagtcggaa ccccggaaac    780
gctgagattg aagatctcat tttcctggca cggtcagcac ttattctaag aggatcagtt    840
gcacataagt cttgcctgcc tgcttgtgtg tatgggcttg cagtggcaag tgggcatgac    900
tttgaaaggg aagggtattc actggtcggg atagacccat taaattact ccaaaacagt    960 caagtgttca gcttgataag accaaatgaa aacccagctc acaagagtca attagtgtgg    1020
atggcatgcc actctgctgc atttgaggat ctgagggtat caagtttcat cagagggaag    1080
aaagtgattc aagaggaag gctctccaca agaggggttc agattgcttc aaatgagaat    1140
gtggaagcca tggattccaa taccttagag ctgagaagca gatactgggc cataaggacc    1200
agaagtggag gaaataccaa tcaacagaag gcatccgcgg gccagatcag tgtgcaaccc    1260
acattctcag tgcaacggaa tctccctttt gaaagagcaa ccattatggc agctttcagc    1320
gggaacaatg aaggacggac atccgatatg cgaacagaag ttataaggat gatggaaat    1380 gcaaagccag aagatttgtc cttccagggg cggggagtct tcgagctctc ggacgaaaaa    1440
gcaacgagcc cgatcgtgcc ttcctttgac atgagtaatg aaggatctta tttcttcgga    1500
gacaatgcag aggagtatga cagttgagga aaaata                             1536

<210> SEQ ID NO 21
<211> LENGTH: 855
<212> TYPE: DNA
<213> ORGANISM: influenza A virus

<400> SEQUENCE: 21
caacgacata atggactcca ccactgtgtc aagctttcag gtagactgtt tcctttggca      60
catccgcaaa cggtttgcag acaatggatt gggtgatgcc ccattccttg atcggctccg    120
ccgagatcaa aagtctctaa aaggaagagg caacacccct ggcctcgaca ttgaaacagc    180
```

| | |
|---|---|
| cactcttgtt gggaaacaaa ttgtggagtg gattttgaaa gaagaatcca gcgatacact | 240 |
| taagatgact attgcatccg tacctacttc gcgctattta gctgacatga ccctcgagga | 300 |
| aatatcacga gactggttaa tgctcatgcc taggcaaaag ataataggcc ctctttgtgt | 360 |
| gcgaatggac caggcgatca tggaaaagaa catcatactg aaagcgaact tcagtgtgat | 420 |
| ctttaaccga ttagagactt tgatactact aagggctttc actgaggagg gaacaatcgt | 480 |
| tggagaaatt tcacaattac cttctcttcc aggacatact aatgaggatg tcaaaaatgc | 540 |
| aattggggtc ctcatcggag gacttgaatg gaatggtaac acggttcgag gctctgaaaa | 600 |
| tctacagaga ttcgcttgga gaaaccgtaa tgaggatggg agaccttcac tacctccaga | 660 |
| gaagaaatga aaagtggcga gagcaattgg gacaaaaatt tgaggaaata aggtggttaa | 720 |
| ttgaagaagt gcggcacaga ttgaaaacga cagagaatag ttttgaacaa ataacattca | 780 |
| tgcaagcctt acaactactg cttgaagtag aacaagagat aaggactttc tcgtttcagc | 840 |
| ttatttaatg ataac | 855 |

<210> SEQ ID NO 22
<211> LENGTH: 2232
<212> TYPE: DNA
<213> ORGANISM: influenza A virus

<400> SEQUENCE: 22

| | |
|---|---|
| accaaaaaaa tggaagactt tgtgcgacaa tgcttcaatc caatgatcgt cgagcttgcg | 60 |
| gaaaaggcaa tgaaggaata tggggaagat ccaaaaatcg aaactaacaa attcgcagca | 120 |
| atatgcactc acttggaagt atgtttcatg tattcggatt ccacttcat tgatgagcga | 180 |
| ggcgaatcaa taattgtgga atctggtgat ccaaatgcat tactgaagca ccgatttgaa | 240 |
| ataattgaag gaagagacag aacaatggcc tggacagtgg tgaatagcat ctgcaacacc | 300 |
| acaggggtcg agaagcctaa atttcttccg gatctgtatg attacaagga gaaccgattc | 360 |
| attgaaattg gagtaacacg gagagaggtt catatatact acctagagaa agccaacaag | 420 |
| ataaaatctg agaagacaca cattcacatc ttttcattta ctggagaaga aatggccacc | 480 |
| aaagcagact acactcttga tgaagaaagc agggcaagaa tcaaaaccag gctattcact | 540 |
| ataagacaag aaatggccag caggggtcta tgggattcct ttcgtcagtc tgaaagaggc | 600 |
| gaagagacaa ttgaggaaag atttgaaatc acaggaacca tgcgtaggct tgccgaccaa | 660 |
| agtctcccac cgaatttctc cagccttgaa aactttagag cctatgtgga tggattcgaa | 720 |
| ccgaacggct gcattgaggg caagctttct caaatgtcaa agaagtgaa tgccaggatt | 780 |
| gagccattcc tgaagacaac accacgccct ctcaaattac ctgatgggcc ccttgctct | 840 |
| cagcggtcaa aattcttgct gatggatgcc ttgaaactaa gcatcgaaga cccgagtcac | 900 |
| gagggagagg gtataccact atacgatgca atcaaatgca tgaagacatt tttcggctgg | 960 |
| aaagagccca acataatcaa accacatgag aaaggcataa atcccaatta ctttctggct | 1020 |
| tggaagcaag tgctagcaga actccaggac cttgaaaatg aagagaagat cccaagaca | 1080 |
| aagaacatga gaaaacaag ccaattgaag tgggtgcttg gtgagaatat ggcaccagaa | 1140 |
| aaagtggact ttgaggattg caaggacatt ggcgatctaa agcagtatga tagtgatgag | 1200 |
| ccagagccta gatcgctggc aagctggatc cagagtgaat tcaataaggc atgtgaattg | 1260 |
| accgactcga gctggataga acttgatgaa ataggagaag atgttgctcc gattgaacac | 1320 |
| attgcaagta tgaggaggaa ctattttaca gcagaagtgt cccactgcag gccactgaa | 1380 |
| tacataatga aaggagtcta cataaataca gctctgctca atgcatcttg tgcagccatg | 1440 |

```
gatgacttcc agctgattcc aatgataagc aaatgtagaa caaaggaagg aagacggaaa      1500
acaaacctgt atgggttcat cataaaagga agatctcatt tgaggaatga tactgatgtg      1560
gtaaactttg tgagcatgga attttctctc actgacccga ggctagaacc acacaaatgg      1620
gagaagtatt gtgttcttga aataggagat atgctcctga ggactgcaat aggccaagtg      1680
tcaaggccca tgttcctgta cattagaacc aatgggacct ccaagatcaa gatgaaatgg      1740
ggtatggaaa tgaggcgctg cctccttcaa tctcttcaac agattgagag catgattgag      1800
gctgagtctt ctgtcaaaga aaaggacatg actaaggaat tctttgaaaa caagtcggaa      1860
acgtggccaa ttggagaatc ccccagagga gtagaggaag gctctattgg gaaagtatgc      1920
agaaccttac tggcaaagtc tgtattcaac agtctgtacg catctccaca acttgagggg      1980
ttttcagctg aatcgagaaa attgcttctc attgttcagg cacttaggga caacctggaa      2040
cctgggacct tcgatcttgg ggggctatac gaagcaattg aggagtgcct gattaatgat      2100
ccctgggttt tgcttaatgc atcttggttc aactccttcc tcacacatgc actgaaatag      2160
ttgtggcaat gctactattt gctatccata ctgtccaaaa aagtaccttg tttctactaa      2220
tagaagagcg at                                                           2232

<210> SEQ ID NO 23
<211> LENGTH: 2336
<212> TYPE: DNA
<213> ORGANISM: influenza A virus

<400> SEQUENCE: 23
gaatggatgt caatccgacc ctacttttcc taaaagttcc agcgcaaaat gccataagca        60
ccacattccc ttatactgga gatcctccat acagccatgg aacaggaaca ggatacacca       120
tggacacagt caacagaaca catcaatatt cagaaaaagg aagtggacg ataaacacag        180 agactggggc accccagctc aacccgattg atggaccact acctgaggat aatgaaccaa       240
gtggatatgc acaaacagaa tgtgttctgg aggccatggc tttccttgaa gagtcccacc       300
cagggatatt tgagaattca tgccttgaaa caatggaagt tgttcaacaa caagggtgg        360 ataaactaac tcaaggtcgc caaacttatg attggacatt aaacagaaat caaccagcag       420
caactgcatt ggccaacacc atagaagttt ttagatcgaa tagtctaaca gccaatgagt       480
caggaagact aatagatttc ctaaaggatg taatggaatc aatggataga gaagaaatgg       540
agataacaac acactttcaa agaaaaagga gagtgagaga caacatgacc aagaagatgg       600
tcacacaaag aacaatagga agaaaaaac aaagattgag taagagaagt tatctaataa        660
gagcacttac attgaatacg atgaccaaag atgcagagag aggcaaatta aaaagaaggg       720
ctatcgcaac acccgggatg caaattagag ggttcgtgta ctttgttgag actttagcta       780
ggagcatttg cgaaaagctt gaacagtctg gactcccagt aggggaaat gaaaagaagg        840 ccaaattggc aaatgttgtg agaaaaatga tgactaattc acaagacaca gagctttctt       900
tcacaatcac tggggacaat actaagtgga atgaaaatca aaatcctcga atgttcctgg       960
cgatgattac atatatcacc cgaaatcaac ccgagtggtt cagaaacatc ctgagcatgg      1020
cacccataat gttttcaaac aaaatggcaa gactaggaaa agggtacatg ttcgagagta       1080
aaaggatgaa gctccgaaca caaataccag cagaaatgct agcaagcatt gatctgaagt       1140
atttcaatga atcaacaagg aagaaaattg agaaaataag gcctcttcta atagatggca       1200
cagcatcatt gagccctgga atgatgatgg gcatgttcaa catgctaagt acggttttgg       1260
gagtctcgat actgaatctt ggacaaaaga atacaccag acaacatac tggtgggatg         1320
```

```
ggctccaatc ctccgacgat tttgccctca ttgtgaatgc accaaattat gagggaatac    1380
aagcaggagt gaatagattc tacaggacct gcaagttagt aggaataaac atgagcaaaa    1440
agaagtccta tataaataaa acagggacat ttgaattcac aagcttttt tatcgctatg     1500 ggtttgtggc taattttagc atggagctgc ccagttttgg agtgtctgga ataaatgaat    1560
cagctgatat gagtattgga gtaacagtga taaagaacaa tatgataaac aatgatcttg    1620
gacctgcaac agcccagatg gcccttcaat tgttcatcaa agactacaga tacacatata    1680
ggtgccacag aggagacaca caaattcaga cgagaagatc attcgagcta agaagctat     1740 gggatcaaac ccgatcaaat gcaggactat tagtatctga tggaggacca aacttataca    1800
atatcaggaa tcttcacatt cctgaagtct gcttaaaatg ggagctaatg gatgaggatt    1860
atcggggaag gctttgtaat cccctgaatc cttttgtcag ccataaagag attgattctg    1920
taaacaatgc tgtggtgatg ccagcccatg gcccagccaa aagcatggaa tatgatgccg    1980
ttgcaactac acactcctgg atccccaaga ggaatcgctc tattctcaac acaagccaaa    2040
ggggaattct tgaggatgaa cagatgtacc agaagtgctg caacctgttc gagaaatttt    2100
tccctagtag ttcatacagg agaccggttg gaatttctag catggtggag gccatggtgt    2160
ctagggcccg gattgatgcc agaatcgact tcgagtctgg acggattaag aaagaagagt    2220
tctctgagat cataaggatc tgttccacca ttgaagaact cagacggcaa acatgatgaa    2280
tttggcttgt ccttcatgaa aaaatgcctt gtttctacta ataccgagac gatata        2336

<210> SEQ ID NO 24
<211> LENGTH: 2297
<212> TYPE: DNA
<213> ORGANISM: influenza A virus

<400> SEQUENCE: 24
tatattcaat atggagagaa taaaagaact aagagatcta atgtcgcagt cccgcactcg    60
cgaaatcctc accaagacca ctgtggacca tatggccata atcaaaaagt acacatcagg    120
aaggcaagag aagaaccctg cactcagaat gaagtggatg atggcaatga agtacccaat    180
cacagcagac aagagaataa tggacatgat tccagagaga atgaacaag  acaaaccct    240 ctggagcaaa acaaacgatg ctggatcgga ccgcgtgatg gtatcacccc tggctgtaac    300
atggtggaat aggaatggcc aacagcaag cacagttcac taccctaagg tatataaaac    360
ttatttcgaa aaagtcgaaa ggttaaaaca tggtaccttt ggccctgtcc acttcaggaa    420
tcaagttaaa ataagaagga gagttgacac aaaccctggt cacgcagatc tcagtgccaa    480
ggaggcacag gatgtgatca tggaagttgt tttcccaaat gaggtggggg caagaatact    540
gacatcagag tcacagctga caataacaaa agagaagaaa gaagagctcc aggattgtaa    600
aattgctccc ttaatggtgg catacatgct agaaaaagag ttggtccgta aaacgaggtt    660
tctcccggtg gctggtggaa caggcagtgt ttatattgaa gtgctgcatt taactcaggg    720
gacatgctgg gagcaaatgt acactccagg aggagaagtg agaaatgatg atgttgacca    780
aagtttgatt attgctgcta gaaacatagt aagaagagca gcagtgtcag cagacccatt    840
agcatctctt ttggaaatgt gccacagcac acagattgga ggaataagga tggtggacat    900
ccttagacag aatccaacgg aggaacaagc cgtagcata tgcaaggcag caatgggggct    960 gaggattagc tcctctttca gctttggtgg gttcactttc aaaagaacaa gtgggtcatc    1020
agttaagaga gaagaagaag tgctcacggg caaccttcaa acactgaaaa taagagtaca    1080
tgaaggatat gaagaattca caatggtcgg agaagaagca cagctattc tcagaaagc    1140
```

```
aaccaggaga ttgatccagt taatagtaag tgggagagat gagcagtcaa ttgctgaggc   1200
aataattgtg gccatggtat tttcacaaga ggattgcatg atcaaggcag ttaggggcga   1260
tctgaacttt gtcaataggg caaaccagcg actgaatccc atgcatcaac tcttgaggca   1320
tttccaaaaa gatgcaaaag tgcttttcca gaattgggga attgaaccca tcgacaatgt   1380
gatgggaatg atcgggatat tgcccgatat gaccccaagc acggagatgt cgctgagagg   1440
gataagagtc agcaaaatgg gagtagatga atactccagc acagagagag tggtagtgag   1500
cattgacaga ttttttgaggg ttcgggatca acgagggaac gtactattgt ctcctgaaga   1560
ggtcagtgag acacaaggga cggagaaatt ggcaataact tattcgtcat cgatgatgtg   1620
ggagatcagt ggccctgagt cagtgctggt caacacttat caatggatca taaggaattg   1680
ggaaagtttg aaaattcaat ggtcacaaga tcccacgatg ttatacaaca aaatggaatt   1740
tgaaccattt cagtctcttg tccctaaagc aaccagaagt cgttacagtg ggttcgtgag   1800
gacactgttc cagcaaatgc gggatgtgat tggaacattt gacactgtcc aaataataaa   1860
acttctcccc tttgctgctg ctccaccaga acagagtagg atgcagtttt cctcactgac   1920
tgtgaatgtg agaggatcag ggttgaggat actggtaaga ggcaattctc cagtattcaa   1980
ttacaataaa gcaaccaaaa ggcttacagt tcttggaaag gatgcaggtg aattgaccga   2040
agacccagat gaaggcacag ctggagtgga gtctgctgtc ctgagggggat ttctcatttt   2100 gggcaaagaa gacaagagat atggtccagc attaagcatc aatgaactga gcaatcttgc   2160
aaaaggagag aaagctaatg tgctaattgg gcaaggagac gtagtgttgg taatgaaacg   2220
gaaacgggac tctagcatac ttactgacag ccagacagcg accaaaagaa ttcggacggc   2280
catcaattag tgtcgaa                                                 2297

<210> SEQ ID NO 25
<211> LENGTH: 562
<212> TYPE: PRT
<213> ORGANISM: influenza A virus

<400> SEQUENCE: 25

Met Thr Ile Thr Phe Leu Ile Leu Leu Phe Thr Val Val Lys Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asn Ile Leu
        35                  40                  45

Glu Lys Thr His Asn Gly Lys Leu Cys Arg Leu Ser Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Val Glu
                85                  90                  95

Lys Glu Asn Pro Val Asn Gly Leu Cys Tyr Pro Gly Ser Phe Asn Asp
            100                 105                 110

Tyr Glu Glu Leu Lys His Leu Leu Thr Ser Val Thr His Phe Glu Lys
        115                 120                 125

Val Lys Ile Leu Pro Arg Asp Gln Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Ser Ile Ala Lys Arg
```

```
                   165                 170                 175
Ser Tyr Asn Asn Thr Ser Gly Glu Gln Met Leu Val Ile Trp Gly Ile
            180                 185                 190
His His Pro Asn Asp Asp Ala Glu Gln Arg Thr Leu Tyr Gln Asn Val
        195                 200                 205
Gly Thr Tyr Val Ser Val Gly Thr Ser Thr Leu Asn Lys Arg Ser Ile
    210                 215                 220
Pro Glu Ile Ala Thr Arg Pro Lys Val Asn Gly Leu Gly Gly Arg Met
225                 230                 235                 240
Glu Phe Ser Trp Thr Leu Leu Glu Thr Trp Asp Val Ile Asn Phe Glu
                245                 250                 255
Ser Thr Gly Asn Leu Ile Ala Pro Glu Tyr Gly Phe Lys Ile Ser Lys
            260                 265                 270
Arg Gly Ser Ser Gly Ile Met Lys Thr Glu Lys Ile Leu Glu Asn Cys
        275                 280                 285
Glu Thr Lys Cys Gln Thr Pro Leu Gly Ala Ile Asn Thr Thr Leu Pro
    290                 295                 300
Phe His Asn Ile His Pro Leu Thr Ile Gly Glu Cys Pro Lys Tyr Val
305                 310                 315                 320
Lys Ser Asp Arg Leu Ile Leu Ala Thr Gly Val Arg Asn Val Pro Gln
                325                 330                 335
Ile Glu Ser Arg Gly Leu Phe Gly Ala Ile Ala Gly Phe Ile Glu Gly
            340                 345                 350
Gly Trp Gln Gly Met Val Asp Gly Trp Tyr Gly Tyr His His Ser Asn
        355                 360                 365
Asp Gln Gly Ser Gly Tyr Ala Ala Asp Lys Glu Ser Thr Gln Lys Ala
    370                 375                 380
Ile Asp Gly Ile Thr Asn Lys Val Asn Ser Val Ile Glu Lys Met Asn
385                 390                 395                 400
Thr Gln Phe Glu Ala Val Gly Lys Glu Phe Asn Asn Leu Glu Arg Arg
                405                 410                 415
Leu Glu Asn Leu Asn Lys Lys Met Glu Asp Gly Phe Ile Asp Val Trp
            420                 425                 430
Thr Tyr Asn Ala Glu Leu Leu Val Leu Met Glu Asn Glu Arg Thr Leu
        435                 440                 445
Asp Phe His Asp Ser Asn Val Lys Asn Leu Tyr Asp Lys Val Arg Met
    450                 455                 460
Gln Leu Arg Asp Asn Ala Lys Glu Ile Gly Asn Gly Cys Phe Glu Phe
465                 470                 475                 480
Tyr His Lys Cys Asp Asp Glu Cys Met Asn Ser Val Arg Asn Gly Thr
                485                 490                 495
Tyr Asp Tyr Pro Lys Tyr Glu Glu Ser Lys Leu Asn Arg Asn Glu
            500                 505                 510
Ile Lys Gly Val Lys Leu Ser Asn Met Gly Val Tyr Gln Ile Leu Ala
        515                 520                 525
Ile Tyr Ala Thr Val Ala Gly Ser Leu Ser Leu Ala Ile Met Ile Ala
    530                 535                 540
Gly Ile Ser Phe Trp Met Cys Ser Asn Gly Ser Leu Gln Cys Arg Ile
545                 550                 555                 560
Cys Ile

<210> SEQ ID NO 26
<211> LENGTH: 252
<212> TYPE: PRT
```

<213> ORGANISM: influenza A virus

<400> SEQUENCE: 26

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Ile Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Thr Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 27
<211> LENGTH: 469
<212> TYPE: PRT
<213> ORGANISM: influenza A virus

<400> SEQUENCE: 27

```
Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Ile Phe Asn
            20                  25                  30

Thr Val Ile His Glu Lys Ile Gly Asp His Gln Ile Val Thr Tyr Pro
        35                  40                  45

Thr Ile Thr Thr Pro Ala Val Pro Asn Cys Ser Asp Thr Ile Ile Thr
    50                  55                  60

Tyr Asn Asn Thr Val Ile Asn Asn Ile Thr Thr Thr Ile Ile Thr Glu
65                  70                  75                  80

Glu Glu Arg Pro Phe Lys Ser Pro Leu Pro Leu Cys Pro Phe Arg Gly
                85                  90                  95

Phe Phe Pro Phe His Lys Asp Asn Ala Ile Arg Leu Gly Glu Asn Lys
            100                 105                 110
```

```
Asp Val Ile Val Thr Arg Glu Pro Tyr Val Ser Cys Asp Asn Asp Asn
            115                 120                 125

Cys Trp Ser Phe Ala Leu Thr Gln Gly Ala Leu Leu Gly Thr Lys His
130                 135                 140

Ser Asn Gly Thr Ile Lys Asp Arg Thr Pro Tyr Arg Ser Leu Ile Arg
145                 150                 155                 160

Phe Pro Ile Gly Thr Ala Pro Val Leu Gly Asn Tyr Lys Glu Ile Cys
                165                 170                 175

Ile Ala Trp Ser Ser Ser Cys Phe Asp Gly Lys Glu Trp Met His
            180                 185                 190

Val Cys Met Thr Gly Asn Asp Asn Ala Ser Ala Gln Ile Ile Tyr
            195                 200                 205

Gly Gly Arg Met Thr Asp Ser Ile Lys Ser Trp Arg Lys Asp Ile Leu
            210                 215                 220

Arg Thr Gln Glu Ser Glu Cys Gln Cys Ile Asp Gly Thr Cys Val Val
225                 230                 235                 240

Ala Val Thr Asp Gly Pro Ala Ala Asn Ser Ala Asp Tyr Arg Val Tyr
                245                 250                 255

Trp Ile Arg Glu Gly Lys Ile Ile Lys Tyr Glu Asn Val Pro Lys Thr
            260                 265                 270

Lys Ile Gln His Leu Glu Glu Cys Ser Cys Tyr Val Asp Ile Asp Val
            275                 280                 285

Tyr Cys Ile Cys Arg Asp Asn Trp Lys Gly Ser Asn Arg Pro Trp Met
            290                 295                 300

Arg Ile Asn Asn Glu Thr Ile Leu Glu Thr Gly Tyr Val Cys Ser Lys
305                 310                 315                 320

Phe His Ser Asp Thr Pro Arg Pro Ala Asp Pro Ser Thr Met Ser Cys
                325                 330                 335

Asp Ser Pro Ser Asn Val Asn Gly Gly Pro Gly Val Lys Gly Phe Gly
            340                 345                 350

Phe Lys Ala Gly Asp Asp Val Trp Leu Gly Arg Thr Val Ser Thr Ser
            355                 360                 365

Gly Arg Ser Gly Phe Glu Ile Ile Lys Val Thr Glu Gly Trp Ile Asn
            370                 375                 380

Ser Pro Asn His Val Lys Ser Ile Thr Gln Thr Leu Val Ser Asn Asn
385                 390                 395                 400

Asp Trp Ser Gly Tyr Ser Gly Ser Phe Ile Val Lys Ala Lys Asp Cys
                405                 410                 415

Phe Gln Pro Cys Phe Tyr Val Glu Leu Ile Arg Gly Arg Pro Asn Lys
            420                 425                 430

Asn Asp Asp Val Ser Trp Thr Ser Asn Ser Ile Val Thr Phe Cys Gly
            435                 440                 445

Leu Asp Asn Glu Pro Gly Ser Gly Asn Trp Pro Asp Gly Ser Asn Ile
450                 455                 460

Gly Phe Met Pro Lys
465

<210> SEQ ID NO 28
<211> LENGTH: 498
<212> TYPE: PRT
<213> ORGANISM: influenza A virus

<400> SEQUENCE: 28

Met Ala Ser Gln Gly Thr Lys Arg Ser Tyr Glu Gln Met Glu Thr Gly
1               5                   10                  15
```

Gly Glu Arg Gln Asp Ala Thr Glu Ile Arg Ala Ser Val Gly Arg Met
            20                  25                  30

Ile Gly Gly Ile Gly Lys Phe Tyr Ile Gln Met Cys Thr Glu Leu Lys
        35                  40                  45

Leu Ser Asp Tyr Glu Gly Arg Leu Ile Gln Asn Ser Met Thr Ile Glu
50                  55                  60

Arg Met Val Leu Ser Ala Phe Asp Glu Arg Asn Lys Tyr Leu Glu
65                  70                  75                  80

Glu His Pro Ser Ala Gly Lys Asp Pro Lys Lys Thr Gly Pro Ile
                85                  90                  95

Tyr Arg Arg Val Asp Gly Lys Trp Met Arg Glu Leu Ile Leu Tyr Asp
                100                 105                 110

Lys Glu Glu Ile Arg Arg Val Trp Arg Gln Ala Asn Asn Gly Glu Asp
                115                 120                 125

Ala Thr Ala Gly Leu Ala His Ile Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Val Ala Met Glu
                180                 185                 190

Leu Ile Arg Met Ile Lys Arg Gly Ile Asn Asp Arg Asn Phe Trp Arg
                195                 200                 205

Gly Glu Asn Gly Arg Lys Thr Arg Ile Ala Tyr Glu Arg Met Cys Asn
                210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Leu Ala Val Ala Ser Gly
                275                 280                 285

His Asp Phe Glu Arg Glu Gly Tyr Ser Leu Val Gly Ile Asp Pro Phe
                290                 295                 300

Lys Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Lys Lys Val
                340                 345                 350

Ile Pro Arg Gly Arg Leu Ser Thr Arg Gly Val Gln Ile Ala Ser Asn
                355                 360                 365

Glu Asn Val Glu Ala Met Asp Ser Asn Thr Leu Glu Leu Arg Ser Arg
                370                 375                 380

Tyr Trp Ala Ile Arg Thr Arg Ser Gly Gly Asn Thr Asn Gln Gln Lys
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Ser Gly Asn
                420                 425                 430

Asn Glu Gly Arg Thr Ser Asp Met Arg Thr Glu Val Ile Arg Met Met

```
                    435                 440                 445
Glu Asn Ala Lys Pro Glu Asp Leu Ser Phe Gln Gly Arg Gly Val Phe
            450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Ser

<210> SEQ ID NO 29
<211> LENGTH: 219
<212> TYPE: PRT
<213> ORGANISM: influenza A virus

<400> SEQUENCE: 29

Met Asp Ser Thr Thr Val Ser Ser Phe Gln Val Asp Cys Phe Leu Trp
1               5                   10                  15

His Ile Arg Lys Arg Phe Ala Asp Asn Gly Leu Gly Asp Ala Pro Phe
                20                  25                  30

Leu Asp Arg Leu Arg Arg Asp Gln Lys Ser Leu Lys Gly Arg Gly Asn
            35                  40                  45

Thr Leu Gly Leu Asp Ile Glu Thr Ala Thr Leu Val Gly Lys Gln Ile
50                  55                  60

Val Glu Trp Ile Leu Lys Glu Ser Ser Asp Thr Leu Lys Met Thr
65                  70                  75                  80

Ile Ala Ser Val Pro Thr Ser Arg Tyr Leu Ala Asp Met Thr Leu Glu
                85                  90                  95

Glu Ile Ser Arg Asp Trp Leu Met Leu Met Pro Arg Gln Lys Ile Ile
            100                 105                 110

Gly Pro Leu Cys Val Arg Met Asp Gln Ala Ile Met Glu Lys Asn Ile
        115                 120                 125

Ile Leu Lys Ala Asn Phe Ser Val Ile Phe Asn Arg Leu Glu Thr Leu
130                 135                 140

Ile Leu Leu Arg Ala Phe Thr Glu Glu Gly Thr Ile Val Gly Glu Ile
145                 150                 155                 160

Ser Gln Leu Pro Ser Leu Pro Gly His Thr Asn Glu Asp Val Lys Asn
                165                 170                 175

Ala Ile Gly Val Leu Ile Gly Gly Leu Glu Trp Asn Gly Asn Thr Val
            180                 185                 190

Arg Gly Ser Glu Asn Leu Gln Arg Phe Ala Trp Arg Asn Arg Asn Glu
        195                 200                 205

Asp Gly Arg Pro Ser Leu Pro Pro Glu Lys Lys
    210                 215

<210> SEQ ID NO 30
<211> LENGTH: 716
<212> TYPE: PRT
<213> ORGANISM: influenza A virus

<400> SEQUENCE: 30

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
                20                  25                  30

Asn Lys Phe Ala Ala Ile Cys Thr His Leu Glu Val Cys Phe Met Tyr
            35                  40                  45
```

```
Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
                115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
                180                 185                 190

Gln Ser Glu Arg Gly Glu Glu Thr Ile Glu Arg Phe Glu Ile Thr
    195                 200                 205

Gly Thr Met Arg Arg Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Lys Leu Pro Asp
                260                 265                 270

Gly Pro Pro Cys Ser Gln Arg Ser Lys Phe Leu Leu Met Asp Ala Leu
            275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Ile Lys Pro His Glu Lys Gly Ile Asn Pro Asn Tyr Phe Leu
                325                 330                 335

Ala Trp Lys Gln Val Leu Ala Glu Leu Gln Asp Leu Glu Asn Glu Glu
                340                 345                 350

Lys Ile Pro Lys Thr Lys Asn Met Lys Lys Thr Ser Gln Leu Lys Trp
            355                 360                 365

Val Leu Gly Glu Asn Met Ala Pro Glu Lys Val Asp Phe Glu Asp Cys
    370                 375                 380

Lys Asp Ile Gly Asp Leu Lys Gln Tyr Asp Ser Asp Glu Pro Glu Pro
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
    435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480
```

```
Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
        530                 535                 540

Ile Gly Asp Met Leu Leu Arg Thr Ala Ile Gly Gln Val Ser Arg Pro
545                 550                 555                 560

Met Phe Leu Tyr Ile Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Val Lys Glu Lys Asp Met Thr
            595                 600                 605

Lys Glu Phe Phe Glu Asn Lys Ser Glu Thr Trp Pro Ile Gly Glu Ser
        610                 615                 620

Pro Arg Gly Val Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
        690                 695                 700

Ser Trp Phe Asn Ser Phe Leu Thr His Ala Leu Lys
705                 710                 715

<210> SEQ ID NO 31
<211> LENGTH: 757
<212> TYPE: PRT
<213> ORGANISM: influenza A virus

<400> SEQUENCE: 31

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Ile Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Glu Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
        130                 135                 140
```

-continued

```
Asn Thr Ile Glu Val Phe Arg Ser Asn Ser Leu Thr Ala Asn Glu Ser
145                 150                 155                 160

Gly Arg Leu Ile Asp Phe Leu Lys Asp Val Met Glu Ser Met Asp Arg
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
            195                 200                 205

Lys Gln Arg Leu Ser Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
                340                 345                 350

Lys Gly Tyr Met Phe Glu Ser Lys Arg Met Lys Leu Arg Thr Gln Ile
            355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
                420                 425                 430

Arg Thr Thr Tyr Trp Trp Asp Gly Leu Gln Ser Ser Asp Asp Phe Ala
            435                 440                 445

Leu Ile Val Asn Ala Pro Asn Tyr Glu Gly Ile Gln Ala Gly Val Asn
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
```

```
                    565                 570                 575
Lys Lys Leu Trp Asp Gln Thr Arg Ser Asn Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Arg Gly Arg Leu
    610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Ile Arg Ile Cys Ser Thr Ile Glu Glu
            740                 745                 750

Leu Arg Arg Gln Thr
        755

<210> SEQ ID NO 32
<211> LENGTH: 759
<212> TYPE: PRT
<213> ORGANISM: influenza A virus

<400> SEQUENCE: 32

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Met
        50                  55                  60

Asp Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Ala Ser Thr Val His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Thr Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
```

```
                      180                 185                 190
Leu Gln Asp Cys Lys Ile Ala Pro Leu Met Val Ala Tyr Met Leu Glu
                195                 200                 205
Lys Glu Leu Val Arg Lys Thr Arg Phe Leu Pro Val Ala Gly Gly Thr
            210                 215                 220
Gly Ser Val Tyr Ile Glu Val Leu His Leu Thr Gln Gly Thr Cys Trp
225                 230                 235                 240
Glu Gln Met Tyr Thr Pro Gly Gly Glu Val Arg Asn Asp Asp Val Asp
                245                 250                 255
Gln Ser Leu Ile Ile Ala Ala Arg Asn Ile Val Arg Arg Ala Ala Val
            260                 265                 270
Ser Ala Asp Pro Leu Ala Ser Leu Leu Glu Met Cys His Ser Thr Gln
        275                 280                 285
Ile Gly Gly Ile Arg Met Val Asp Ile Leu Arg Gln Asn Pro Thr Glu
        290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Arg Glu Glu Val Leu Thr Gly Asn Leu Gln Thr Leu
            340                 345                 350
Lys Ile Arg Val His Glu Gly Tyr Glu Glu Phe Thr Met Val Gly Arg
            355                 360                 365
Arg Ala Thr Ala Ile Leu Arg Lys Ala Thr Arg Leu Ile Gln Leu
        370                 375                 380
Ile Val Ser Gly Arg Asp Glu Gln Ser Ile Ala Glu Ala Ile Val
385                 390                 395                 400
Ala Met Val Phe Ser Gln Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
        435                 440                 445
Trp Gly Ile Glu Pro Ile Asp Asn Val Met Gly Met Ile Gly Ile Leu
        450                 455                 460
Pro Asp Met Thr Pro Ser Thr Glu Met Ser Leu Arg Gly Ile Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Val Leu
            500                 505                 510
Leu Ser Pro Glu Glu Val Ser Glu Thr Gln Gly Thr Glu Lys Leu Ala
        515                 520                 525
Ile Thr Tyr Ser Ser Ser Met Met Trp Glu Ile Ser Gly Pro Glu Ser
        530                 535                 540
Val Leu Val Asn Thr Tyr Gln Trp Ile Ile Arg Asn Trp Glu Ser Leu
545                 550                 555                 560
Lys Ile Gln Trp Ser Gln Asp Pro Thr Met Leu Tyr Asn Lys Met Glu
                565                 570                 575
Phe Glu Pro Phe Gln Ser Leu Val Pro Lys Ala Thr Arg Ser Arg Tyr
            580                 585                 590
Ser Gly Phe Val Arg Thr Leu Phe Gln Gln Met Arg Asp Val Ile Gly
        595                 600                 605
```

-continued

```
Thr Phe Asp Thr Val Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Leu Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Glu Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Thr Ala Ile Asn
        755
```

<210> SEQ ID NO 33
<211> LENGTH: 21
<212> TYPE: DNA
<213> ORGANISM: artificial
<220> FEATURE:
<223> OTHER INFORMATION: oligonucleotide primer

<400> SEQUENCE: 33
caggcagttt caatgattat g                                              21

<210> SEQ ID NO 34
<211> LENGTH: 20
<212> TYPE: DNA
<213> ORGANISM: artificial
<220> FEATURE:
<223> OTHER INFORMATION: oligonucleotide primer

<400> SEQUENCE: 34
ccatcaattg cctttttgagt                                               20

<210> SEQ ID NO 35
<211> LENGTH: 21
<212> TYPE: DNA
<213> ORGANISM: artificial
<220> FEATURE:
<223> OTHER INFORMATION: oligonucleotide primer

<400> SEQUENCE: 35
agcaaaagca ggtgcgagat g                                              21

<210> SEQ ID NO 36
<211> LENGTH: 24
<212> TYPE: DNA
<213> ORGANISM: artificial
<220> FEATURE:
<223> OTHER INFORMATION: oligonucleotide primer

<400> SEQUENCE: 36
agtagaaaca aggtgctttt ttct                                           24

<210> SEQ ID NO 37

<211> LENGTH: 1689
<212> TYPE: DNA
<213> ORGANISM: influenza A virus

<400> SEQUENCE: 37
atgaccatca cttttctcat cctcctgttc acagtagtga aaggggacca aatatgcatc 60
ggataccatg ccaacaattc cacagaaaaa gttgacacaa tcttggaacg aaacgtcacc 120
gtgactcatg ccaagaacat tcttgaaaag acgcataatg gaaagttgtg cagattgagc 180
gggatccctc cattggaact gggggattgc agcattgcag gttggctcct tggaaatccg 240
gaatgtgacc ggctcttaag tgtacctgaa tggtcctata tagtggaaaa ggaaaacccg 300
gtgaatggtc tgtgctatcc aggcagtttc aatgattatg aggaattgaa acatcttctc 360
accagtgtga cacactttga gaaagttaag attctgccca gagatcaatg gacccagcac 420
acaacaactg gtggttctcg ggcctgtgca gtatctggaa acccgtcatt ctttaggaac 480
atggtttggc ttacaaagaa agggtcaaac tacccaattg ctaaaaggtc atacaacaac 540
acaagtgggg agcaaatgct ggtaatatgg gggatacatc accccaatga cgatgcggaa 600
cagaggacac tgtaccagaa tgtgggaaca tatgtttccg ttggaacatc aacactaaat 660
aagaggtcaa tccctgaaat agcaacaagg cccaaagtca atggactggg aggaagaatg 720
gaattctctt ggactctatt ggagacatgg gatgtcataa attttgagag cactggtaat 780
ttaattgcac cagaatacgg attcaaaata tcaaagagag gaagctcagg aattatgaag 840
acagagaaaa tacttgaaaa ttgtgaaacc aaatgtcaga ccccccttggg ggcaataaat 900
acaacattgc cctttcacaa cattcaccca ttgacaatag gtgagtgccc caagtatgta 960
aagtcagata gactgatttt ggcgacagga ctaagaaatg tcccccagat tgaatcaagg 1020
ggattgtttg gagcaatagc tgggtttata gaaggcggat ggcaagggat ggttgatggc 1080
tggtatgggt accatcacag caatgatcaa ggatcaggat atgcagcaga caaagaatcc 1140
actcaaaagg caattgatgg gataactaac aaagtaaatt ctgtgattga aaagatgaac 1200
actcagtttg aggctgttgg gaaagagttc aacaacctag agagaagact ggaaaactta 1260
aataaaaaga tggaagatgg atttattgat gtatggacat ataatgccga actcctagtt 1320
ctaatggaaa atgagaggac acttgatttc catgattcta atgtgaagaa tctgtacgat 1380
aaggtcagaa tgcaattgag agacaatgct aaggaaatag ggaacggatg ctttgagttt 1440
tatcataaat gtgatgatga atgcatgaat agtgtcagga atgggacata tgattatatc 1500
aaatatgagg aagagtccaa gctgaacagg aacgaaatca aaggagtgaa attgagcaat 1560
atgggggttt atcaaatact tgctatatac gctacagttg caggctcttt gtcactggca 1620
atcatgatag ctgggatttc tttctggatg tgttctaatg ggtctctgca atgcagaatt 1680
tgcatatga 1689

<210> SEQ ID NO 38
<211> LENGTH: 1689
<212> TYPE: DNA
<213> ORGANISM: influenza A virus

<400> SEQUENCE: 38
atgaccatca cttttctcat cctcctgttc acagtagtga aaggggacca aatatgcatc 60
ggataccatg ccaacaattc cacagaaaaa gttgacacaa tcttggaacg aaacgtcacc 120
gtgactcatg ccaagaacat tcttgaaaag acgcataatg gaaagttgtg cagattgagt 180
ggaatccctc cattggaact gggggattgc agcattgcag gttggctcct tggaaatccg 240

```
gaatgtgacc ggctcttaag tgtacctgaa tggtcctata tagtggaaaa ggaaaacccg      300
gtgaatggtc tgtgctatcc aggcagtttc aatgattatg aggaattgaa acatcttctc      360
accagtgtga cacactttga gaaagttaag attctgccca gagatcaatg acccagcac       420 acaacaactg gtggttctcg ggcctgtgca gtatctggaa acccgtcatt ctttaggaac      480
atggtttggc ttacaaagaa agggtcaaac tactcaattg ctaaaaggtc atacaacaac      540
acaagtgggg agcaaatgct ggtaatatgg gggatacatc accccaatga cgatgcggaa      600
cagaggacac tgtaccagaa tgtgggaaca tatgtttccg ttggaacatc aacactaaat      660
aagaggtcaa tccctgaaat agcaacaagg cccaaagtca atggactggg aggaagaatg      720
gaattctctt ggactctatt ggagacatgg gatgtcataa attttgagag cactggtaat      780
ttaattgcac cagaatacgg attcaaaata tcaaagagag gaagctcagg aattatgaag      840
acagagaaaa tacttgaaaa ttgtgaaacc aaatgtcaga ccccctttggg ggcaataaat      900 acaacattgc cctttcacaa cattcaccca ttgacaatag gtgagtgccc caagtatgta      960
aagtcagata gactgattttt ggcgacagga gtaagaaatg tcccccagat tgaatcaagg     1020
ggattgtttg gagcaatagc tgggtttata gaaggcggat ggcaagggat ggttgatggc     1080
tggtatgggt accatcacag caatgatcaa ggatcaggat atgcagcaga caaagaatcc     1140
actcaaaagg caattgatgg gataactaac aaagtaaatt ctgtgattga aaagatgaac     1200
actcagtttg aggctgttgg aaagagttca acaacctag agagaaggct ggaaaactta      1260
aataaaaaga tggaagatgg atttattgat gtatggacat ataatgccga actcctagtt     1320
ctaatggaaa atgagaggac acttgatttc catgattcta atgtgaagaa tctgtacgat     1380
aaggtcagaa tgcaattgag agacaatgct aaggaaatag gaacggatg ctttgagttt      1440 tatcataaat gtgatgatga atgcatgaat agtgtcagga atgggacata tgattatccc     1500
aaatatgagg aagagtccaa gctgaacagg aacgaaatca aaggagtgaa attgagcaat     1560
atgggggttt atcaaatact tgctatatac gctacagttg caggctcttt gtcactggca      1620
atcatgatag ctgggatttc tttctggatg tgttctaatg ggtctctgca atgcagaatt     1680
tgcatatga                                                              1689

<210> SEQ ID NO 39
<211> LENGTH: 1410
<212> TYPE: DNA
<213> ORGANISM: influenza A virus

<400> SEQUENCE: 39
atgaatccga atcagaagat aataacaatc ggggtagtga ataccactct gtcaacaata       60
gcccttctca ttggagtggg aaacttagtt ttcaacacag tcatacatga gaaatagga      120 gaccatcaaa tagtgaccta tccaataata acgacccctg cagtaccgaa ctgcagtgac      180
actataataa catacaataa cactgtgata aacaacataa caacaacaat aataactgaa      240
gaagaaaggc ctttcaagtc tccactaccg ctgtgcccct tcagaggatt cttccctttt      300
cacaaggaca atgcaatacg actgggtgaa acaaagacg tcatagtcac aagagagcct      360
tatgttagct gcgataatga caactgctgg tcctttgctc tcgcacaagg agcattgcta      420
gggaccaaac atagcaatgg gaccattaaa gacaggacac catataggtc tctaattcgt      480
ttcccaatag gaacagctcc agtactagga aattataaag agatatgcat tgcttggtcg      540
agcagcagtt gctttgacgg gaaagagtgg atgcatgtgt gcatgacagg aacgataat      600 gatgcaagtg cccagataat atatggaggg agaatgacag actccattaa atcatggaga      660
```

```
aaggacatac taagaactca ggagtctgaa tgccaatgca ttgacgggac ttgtgttgtt      720
gctgtcacag atggccctgc tgctaatagt gcagattaca gggtttactg gatacgggag      780
ggaaaaataa taaagtatga aaatgttccc aaaacaaaga tacaacactt agaagaatgt      840
tcctgctatg tggacattga tgtttactgt atatgtaggg acaattggaa gggctctaac      900
agaccttgga tgagaatcaa caacgagact atactggaaa cagggtatgt atgtagtaaa      960
ttccactcag acacccccag gccagctgac ccttcaacaa tgtcatgtga ctccccaagc     1020
aatgtcaatg gaggacccgg agtgaagggg tttggtttca agctggcga tgatgtatgg      1080 ttaggtagaa cagtgtcgac tagtggtaga tcgggctttg aaattatcaa agttacagaa     1140
gggtggatca actctcctaa ccatgtcaaa tcaattacac aaacactagt gtccaacaat     1200
gactggtcag gctattccgg tagcttcatt gtcaaagcca aggactgttt tcagccctgt     1260 tttatgttg agcttatacg agggaggccc aacaagaatg atgacgtctc ttggacaagt      1320
aatagtatag ttactttctg tggactagac aatgaacctg gatcgggaaa ttggccagat     1380
ggttctaaca ttgggtttat gcccaagtaa                                      1410
```

<210> SEQ ID NO 40
<211> LENGTH: 1410
<212> TYPE: DNA
<213> ORGANISM: influenza A virus

<400> SEQUENCE: 40

```
atgaatccga atcagaagat aataacaatc ggggtagtga ataccactct gtcaacaata       60
gcccttctca ttggagtggg aaacttaatt ttcaacacag tcatacatga gaaaatagga      120
gaccatcaaa tagtgaccta tccaacaata acgaccctg cagtaccgaa ctgcagtgac       180
actataataa catacaataa cactgtgata aacaacataa caacaacaat aataactgaa      240 gaagaaggc ctttcaagtc tccactaccg ctgtgcccct tcagaggatt cttccctttt       300
cacaaggaca atgcaatacg actgggtgaa acaaagacg tcatagtcac aagagagcct      360
tatgttagct gcgataatga caactgctgg tcctttgctc tcacacaagg agcattgcta      420
gggaccaaac atagcaatgg gaccattaaa gacaggacac catataggtc tctaattcgt      480
ttcccaatag gaacagctcc agtactagga aattataaag agatatgcat tgcttggtcg      540
agcagcagtt gctttgacgg gaaagagtgg atgcatgtgt gcatgacagg gacgataat       600 gatgcaagtg cccagataat atatggaggg agaatgacag actccattaa atcatggaga      660
aaggacatac taagaactca ggagtctgaa tgccaatgca ttgacgggac ttgtgttgtt      720
gctgtcacag atggccctgc tgctaatagt gcagattaca gggtttactg gatacgggag      780
ggaaaaataa taaagtatga aaatgttccc aaaacaaaga tacaacactt agaagaatgt      840
tcctgctatg tggacattga tgtttactgt atatgtaggg acaattggaa gggctctaac      900
agaccttgga tgagaatcaa caacgagact atactggaaa cagggtatgt atgtagtaaa      960
ttccactcag acacccccag gccgctgac ccttcaacaa tgtcatgtga ctccccaagc      1020
aatgtcaatg gaggacccgg agtgaagggg tttggtttca agctggcga tgatgtatgg      1080 ttaggtagaa cagtgtcgac tagtggtaga tcgggctttg aaattatcaa agttacagaa     1140
gggtggatca actctcctaa ccatgtcaaa tcaattacac aaacactagt gtcaacaat     1200 gactggtcag gctattccgg tagcttcatt gtcaaagcca aggactgttt tcagccctgt     1260 tttatgttg agcttatacg agggaggccc aacaagaatg atgacgtctc ttggacaagt      1320
aatagtatag ttactttctg tggactagac aatgaacctg gatcgggaaa ttggccagat     1380
```

```
ggttctaaca ttgggtttat gcccaagtaa                                        1410
```

<210> SEQ ID NO 41
<211> LENGTH: 1772
<212> TYPE: DNA
<213> ORGANISM: influenza A virus

<400> SEQUENCE: 41

```
agcaaaagca ggggttatac catagacaac cgaacaaaga caatgaccat cactttctc         60
atcctcctgt tcacagtagt gaaaggggac caaatatgta tcggatacca tgccaacaat       120
tccacagaaa aagttgacac aatcttggaa cgaaacgtca ccgtgactca tgccaaggac       180
attcttgaaa aaacgcataa tggaaagttg tgcagattaa gcgggatccc tccactggaa       240
ctggggggatt gcagcattgc aggttggctc cttggaaatc cggaatgtga ccggctctta       300
agtgtacctg aatggtccta tatagtggaa aaggaaaacc cggtgaatgg tctgtgctac       360
ccaggcagtt tcaatgatta tgaggaattg aaacatctcc tcaccagtgt gacacacttt       420
gagaaagtta agattctgcc cagagatcaa tggactcagc acacaacaac tggtggttct       480
cgggcctgtg cagtgtctgg aaacccgtca ttctttagga acatggtttg cttacaaag        540
aagggtcaa actacccaat tgctaaaagg tcatacaaca acacaagtgg ggagcaaatg        600
ctggtaatct gggggataca tcatcccaat gacgatgcgg aacaaaggac actgtaccag       660
aatgtgggaa catatgtttc cgttgggaca tcaacactaa ataagaggtc aatccctgaa       720
atagcaacaa ggcccaaagt caatggacaa ggagggagaa tggaattctc ttggactcta       780
ttggagacat gggatgtcat aaattttgag agcactggta atttaattgc accagaatac       840
ggattcaaaa tatcaaagag aggaagctca ggaattatga gacacagaa aacacttgaa        900
aattgtgaaa ccaaatgtca ccccccttg ggggcaataa atacaacatt gcccttcac         960
aacattcacc cattgacaat aggtgagtgc cccaagtatg taaagtcaga cagactggtt      1020
ttggcaacag gactaagaaa tgtccctcag attgaatcaa ggggattgtt tggagcaata      1080
gctgggttta gaaaggcgg atggcaaggg atggttgatg gctggtatgg gtatcatcac      1140
agcaatgatc aaggatcagg atatgcagca gacaaagaat ccactcaaaa ggcaattgat      1200
gggataacta caaagtaaa ttctgtgatt gaaagatga acactcagtt tgaggctgtt       1260
gggaaagagt tcaacaatct agagagaaga ctagaaaact taaataaaaa gatggaagat      1320
ggatttcttg atgtatggac atataatgcc gaactcctag ttctaatgga gaatgagagg      1380
acacttgatt ccatgactc taatgtgaag aatctgtacg ataaggtcag aatgcaatta      1440
agagacaatg ctaaggaaat agggaacgga tgctttgagt tttatcataa atgtgatgat      1500
gaatgcatga atagtgtcag gaatggaaca tatgattatc ccaaatatga ggaagagtcc      1560
aagctgaaca ggaacgaaat aaaggactg aaattgagca atatgggggt ctatcaaata      1620
cttgctatat acgctacagt tgcaggctcc ttgtcactgg caatcatgat agctgggatt      1680
tctttctgga tgtgttctaa tgggtctctg caatgcagaa tttgcatatg actgtaagtc      1740
aatttgtaat taaaaacacc cttgtttcta ct                                    1772
```

<210> SEQ ID NO 42
<211> LENGTH: 562
<212> TYPE: PRT
<213> ORGANISM: influenza A virus

<400> SEQUENCE: 42

```
Met Thr Ile Thr Phe Leu Ile Leu Leu Phe Thr Val Val Lys Gly Asp
1               5                   10                  15
```

```
Gln Ile Cys Ile Gly Tyr His Ala Asn Asn Ser Thr Glu Lys Val Asp
             20                  25                  30

Thr Ile Leu Glu Arg Asn Val Thr Val Thr His Ala Lys Asp Ile Leu
         35                  40                  45

Glu Lys Thr His Asn Gly Lys Leu Cys Arg Leu Ser Gly Ile Pro Pro
 50                  55                  60

Leu Glu Leu Gly Asp Cys Ser Ile Ala Gly Trp Leu Leu Gly Asn Pro
 65                  70                  75                  80

Glu Cys Asp Arg Leu Leu Ser Val Pro Glu Trp Ser Tyr Ile Val Glu
                 85                  90                  95

Lys Glu Asn Pro Val Asn Gly Leu Cys Tyr Pro Gly Ser Phe Asn Asp
             100                 105                 110

Tyr Glu Glu Leu Lys His Leu Leu Thr Ser Val Thr His Phe Glu Lys
         115                 120                 125

Val Lys Ile Leu Pro Arg Asp Gln Trp Thr Gln His Thr Thr Thr Gly
 130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Ile Ala Lys Arg
                 165                 170                 175

Ser Tyr Asn Asn Thr Ser Gly Glu Gln Met Leu Val Ile Trp Gly Ile
             180                 185                 190

His His Pro Asn Asp Asp Ala Glu Gln Arg Thr Leu Tyr Gln Asn Val
         195                 200                 205

Gly Thr Tyr Val Ser Val Gly Thr Ser Thr Leu Asn Lys Arg Ser Ile
 210                 215                 220

Pro Glu Ile Ala Thr Arg Pro Lys Val Asn Gly Gln Gly Gly Arg Met
225                 230                 235                 240

Glu Phe Ser Trp Thr Leu Leu Glu Thr Trp Asp Val Ile Asn Phe Glu
                 245                 250                 255

Ser Thr Gly Asn Leu Ile Ala Pro Glu Tyr Gly Phe Lys Ile Ser Lys
             260                 265                 270

Arg Gly Ser Ser Gly Ile Met Lys Thr Glu Lys Thr Leu Glu Asn Cys
         275                 280                 285

Glu Thr Lys Cys Gln Thr Pro Leu Gly Ala Ile Asn Thr Thr Leu Pro
 290                 295                 300

Phe His Asn Ile His Pro Leu Thr Ile Gly Glu Cys Pro Lys Tyr Val
305                 310                 315                 320

Lys Ser Asp Arg Leu Val Leu Ala Thr Gly Leu Arg Asn Val Pro Gln
                 325                 330                 335

Ile Glu Ser Arg Gly Leu Phe Gly Ala Ile Ala Gly Phe Ile Glu Gly
             340                 345                 350

Gly Trp Gln Gly Met Val Asp Gly Trp Tyr Gly Tyr His His Ser Asn
         355                 360                 365

Asp Gln Gly Ser Gly Tyr Ala Ala Asp Lys Glu Ser Thr Gln Lys Ala
 370                 375                 380

Ile Asp Gly Ile Thr Asn Lys Val Asn Ser Val Ile Glu Lys Met Asn
385                 390                 395                 400

Thr Gln Phe Glu Ala Val Gly Lys Glu Phe Asn Asn Leu Glu Arg Arg
                 405                 410                 415

Leu Glu Asn Leu Asn Lys Lys Met Glu Asp Gly Phe Leu Asp Val Trp
             420                 425                 430

Thr Tyr Asn Ala Glu Leu Leu Val Leu Met Glu Asn Glu Arg Thr Leu
```

```
                435                 440                 445
Asp Phe His Asp Ser Asn Val Lys Asn Leu Tyr Asp Lys Val Arg Met
    450                 455                 460

Gln Leu Arg Asp Asn Ala Lys Glu Ile Gly Asn Gly Cys Phe Glu Phe
465                 470                 475                 480

Tyr His Lys Cys Asp Asp Glu Cys Met Asn Ser Val Arg Asn Gly Thr
                485                 490                 495

Tyr Asp Tyr Pro Lys Tyr Glu Glu Ser Lys Leu Asn Arg Asn Glu
                500                 505                 510

Ile Lys Gly Leu Lys Leu Ser Asn Met Gly Val Tyr Gln Ile Leu Ala
            515                 520                 525

Ile Tyr Ala Thr Val Ala Gly Ser Leu Ser Leu Ala Ile Met Ile Ala
            530                 535                 540

Gly Ile Ser Phe Trp Met Cys Ser Asn Gly Ser Leu Gln Cys Arg Ile
545                 550                 555                 560

Cys Ile

<210> SEQ ID NO 43
<211> LENGTH: 1428
<212> TYPE: DNA
<213> ORGANISM: influenza A virus

<400> SEQUENCE: 43
tgcgagatga atccgaatca gaagataata caatcgggg tagtgaatac cactctgtca      60
acaatagccc ttctcattgg agtgggaaac ttagttttca acacagtcat acatgagaaa    120
ataggagacc atcaaatagt gacccatcca acaataacga cccctgcagt accgaactgc    180
agtgacacta ataacata caataacact gtgataaaca acataacaac acaataata      240
actgaagcag aaaggccttt caagtctcca ctaccgctgt gccccttcaa aggattcttc    300
ccttttcaca aggacaatgc aatacgactg gtgagaaca aagacgtcat agtcacaagg    360
gagccttatg ttagctgcga taatgacaac tgctggtcct tgctctcgc acaaggagca    420
ttgctaggga ctaaacatag caatgggacc attaaagaca ggacaccata taggtctcta    480
attcgtttcc aataggaac agctccagta ctgggaaatt acaaagagat atgcattgct    540
tggtcgagca gcagttgctt tgacgggaaa gagtggatgc atgtgtgcat gacagggaac    600
gataatgatg caagtgccca gataatat ggagggagaa tgacagactc cattaaatca    660
tggagaaagg acatactaag aacccaggag tctgaatgtc aatgcattga cgggacttgt    720
gttgttgctg tcacagatgg gcctgctgct aatagtgcag accacaggt ttactggata    780
cgggagggaa gaataataaa gtatgaaaat gttcccaaaa caaagataca acacttagaa    840
gaatgttcct gctatgtgga cattgatgtt tactgtatat gtagggacaa ttggaagggc    900
tctaacagac cttggatgag aatcaacaac gagactatac tggaaacagg gtatgtatgt    960
agtaaattcc actcagacac ccccaggcca gctgacccct caacaatgtc atgtgactcc   1020
ccaagcaatg tcaatggagg acccggagtg aagggggtttg gttccaaagc tggcaatgat   1080
gtatggttag gtagaacagt gtcaactagt ggtagatcgg gctttgaaat atcaaagtt   1140
acagaagggt ggatcaactc tcctaaccat gtcaaatcaa ttacacaaac actagtgtcc   1200
aacaatgact ggtcaggcta ttcaggtagc ttcattgtca aagccaagga ctgtttttcag   1260
ccctgttttt atgttgagct tatacgaggg aggcccaaca agaatgatga cgtctcttgg   1320
acaagtaata gtatagttac ttttctgtgga ctagacaatg aacctggatc gggaggttgg   1380
ccggatggtt ctaacattgg gtttgtgccc aagtaataga aaaaagca                 1428
```

<210> SEQ ID NO 44
<211> LENGTH: 469
<212> TYPE: PRT
<213> ORGANISM: influenza A virus

<400> SEQUENCE: 44

```
Met Asn Pro Asn Gln Lys Ile Ile Thr Ile Gly Val Val Asn Thr Thr
1               5                   10                  15

Leu Ser Thr Ile Ala Leu Leu Ile Gly Val Gly Asn Leu Val Phe Asn
            20                  25                  30

Thr Val Ile His Glu Lys Ile Gly Asp His Gln Ile Val Thr His Pro
        35                  40                  45

Thr Ile Thr Thr Pro Ala Val Pro Asn Cys Ser Asp Thr Ile Ile Thr
    50                  55                  60

Tyr Asn Asn Thr Val Ile Asn Asn Ile Thr Thr Thr Ile Ile Thr Glu
65                  70                  75                  80

Ala Glu Arg Pro Phe Lys Ser Pro Leu Pro Leu Cys Pro Phe Lys Gly
                85                  90                  95

Phe Phe Pro Phe His Lys Asp Asn Ala Ile Arg Leu Gly Glu Asn Lys
            100                 105                 110

Asp Val Ile Val Thr Arg Glu Pro Tyr Val Ser Cys Asp Asn Asp Asn
        115                 120                 125

Cys Trp Ser Phe Ala Leu Ala Gln Gly Ala Leu Leu Gly Thr Lys His
    130                 135                 140

Ser Asn Gly Thr Ile Lys Asp Arg Thr Pro Tyr Arg Ser Leu Ile Arg
145                 150                 155                 160

Phe Pro Ile Gly Thr Ala Pro Val Leu Gly Asn Tyr Lys Glu Ile Cys
                165                 170                 175

Ile Ala Trp Ser Ser Ser Ser Cys Phe Asp Gly Lys Glu Trp Met His
            180                 185                 190

Val Cys Met Thr Gly Asn Asp Asn Asp Ala Ser Ala Gln Ile Ile Tyr
        195                 200                 205

Gly Gly Arg Met Thr Asp Ser Ile Lys Ser Trp Arg Lys Asp Ile Leu
    210                 215                 220

Arg Thr Gln Glu Ser Glu Cys Gln Cys Ile Asp Gly Thr Cys Val Val
225                 230                 235                 240

Ala Val Thr Asp Gly Pro Ala Ala Asn Ser Ala Asp His Arg Val Tyr
                245                 250                 255

Trp Ile Arg Glu Gly Arg Ile Ile Lys Tyr Glu Asn Val Pro Lys Thr
            260                 265                 270

Lys Ile Gln His Leu Glu Glu Cys Ser Cys Tyr Val Asp Ile Asp Val
        275                 280                 285

Tyr Cys Ile Cys Arg Asp Asn Trp Lys Gly Ser Asn Arg Pro Trp Met
    290                 295                 300

Arg Ile Asn Asn Glu Thr Ile Leu Glu Thr Gly Tyr Val Cys Ser Lys
305                 310                 315                 320

Phe His Ser Asp Thr Pro Arg Pro Ala Asp Pro Ser Thr Met Ser Cys
                325                 330                 335

Asp Ser Pro Ser Asn Val Asn Gly Gly Pro Gly Val Lys Gly Phe Gly
            340                 345                 350

Phe Lys Ala Gly Asn Asp Val Trp Leu Gly Arg Thr Val Ser Thr Ser
        355                 360                 365

Gly Arg Ser Gly Phe Glu Ile Ile Lys Val Thr Glu Gly Trp Ile Asn
    370                 375                 380
```

```
Ser Pro Asn His Val Lys Ser Ile Thr Gln Thr Leu Val Ser Asn Asn
385                 390                 395                 400

Asp Trp Ser Gly Tyr Ser Gly Ser Phe Ile Val Lys Ala Lys Asp Cys
                405                 410                 415

Phe Gln Pro Cys Phe Tyr Val Glu Leu Ile Arg Gly Arg Pro Asn Lys
            420                 425                 430

Asn Asp Asp Val Ser Trp Thr Ser Asn Ser Ile Val Thr Phe Cys Gly
        435                 440                 445

Leu Asp Asn Glu Pro Gly Ser Gly Gly Trp Pro Asp Gly Ser Asn Ile
    450                 455                 460

Gly Phe Val Pro Lys
465
```